(12) United States Patent
André et al.

(10) Patent No.: US 11,639,384 B2
(45) Date of Patent: May 2, 2023

(54) TREATMENT OF PEDIATRIC BCP-ALL PATIENTS WITH AN ANTI-KIR ANTIBODY

(71) Applicant: UNIVERSITY CHILDREN'S HOSPITAL TÜBINGEN, Princeton, NJ (US)

(72) Inventors: Maya Caroline André, Basel (CH); Ayline Kübler, Tübingen (DE)

(73) Assignee: University Children's Hospital Tübingen, Baden-Württemberg (DE)

( * ) Notice: Subject to any disclaimer, the term of this patent is extended or adjusted under 35 U.S.C. 154(b) by 0 days.

(21) Appl. No.: 15/522,239

(22) PCT Filed: Oct. 27, 2015

(86) PCT No.: PCT/US2015/057565
§ 371 (c)(1),
(2) Date: Apr. 26, 2017

(87) PCT Pub. No.: WO2016/069589
PCT Pub. Date: May 6, 2016

(65) Prior Publication Data
US 2017/0334993 A1 Nov. 23, 2017

Related U.S. Application Data

(60) Provisional application No. 62/069,478, filed on Oct. 28, 2014.

(51) Int. Cl.
| | | |
|---|---|---|
| *C07K 16/28* | (2006.01) | |
| *A61K 39/00* | (2006.01) | |
| *A61K 39/395* | (2006.01) | |
| *A61K 35/17* | (2015.01) | |

(52) U.S. Cl.
CPC .......... *C07K 16/2803* (2013.01); *A61K 35/17* (2013.01); *A61K 39/39541* (2013.01); *A61K 2039/505* (2013.01); *A61K 2300/00* (2013.01); *C07K 2317/21* (2013.01); *C07K 2317/33* (2013.01); *C07K 2317/565* (2013.01); *C07K 2317/73* (2013.01); *C07K 2317/76* (2013.01); *C07K 2317/92* (2013.01)

(58) Field of Classification Search
CPC ........ A61K 39/39541; A61K 2039/505; C07K 16/2803; C07K 2317/21; C07K 2317/565; C07K 2317/73; C07K 2317/76; C07K 2317/92
See application file for complete search history.

(56) References Cited

U.S. PATENT DOCUMENTS

| | | | | |
|---|---|---|---|---|
| 8,119,775 B2 * | 2/2012 | Moretta | .................. | C07K 16/28 530/388.73 |
| 2005/0222012 A1 * | 10/2005 | Hemenway | .......... | C07K 5/1024 530/328 |
| 2015/0290316 A1 * | 10/2015 | Graziano | ........... | C07K 16/2803 424/174.1 |

FOREIGN PATENT DOCUMENTS

| | | | |
|---|---|---|---|
| WO | WO 2005/003168 | | 1/2005 |
| WO | WO 2006/003179 | | 1/2006 |
| WO | WO 2008/084106 | | 7/2008 |
| WO | WO2014/055648 | * | 4/2014 |
| WO | WO 2014/066532 | | 5/2014 |

OTHER PUBLICATIONS

Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Portolano (The Journal of Immunology, vol. 150, No. 3, p. 880-887, 1993) (Year: 1993).*
Beiboer (J. Mol. Biol. (2000) 296:833-849) (Year: 2000).*
Rudikoff et al. (Proceedings of the National Academy of Sciences USA, vol. 79, p. 1979-1983, 1982) (Year: 1982).*
Spier (Blood, vol. 64, No. 5, p. 1064-1066, 1984) (Year: 1984).*
Chiaretti et al, T-cell acute lymphoblastic leukemia, Haematologica, 2009; 94(2), pp. 160-162 (Year: 2009).*
Hirzel et al (Precursor B-cell Acute lymphoblastic Leukemia/Lymphoma with L3 Morphology, Philadelphia Chromosome, MYC Gene Translocation, and Coexpression of TdT and Surface Light Chains: A Case Report, Case Reports in Pathology, vol. 2013, Article ID 679892, 4 pgs) (Year: 2013).*
Spier et al (Blood, vol. 64, No. 5, p. 1064-1066, 1984 (Year: 1984).*
Alves LG, et al. (2009) A novel real-time PCR method for KIR genotyping. Tissue Antigens 73(2):188-91.
André MC, et al. (2010) Long-term human CD34+ stem cell-engrafted nonobese diabetic/SCID/IL2Rγnull mice show impaired CD8+ T cell maintenance and a functional arrest of immature NK cells. J Immunol 185(5):2710-20.
Benson DM Jr., et al. (2012) A phase 1 trial of the anti-KIR antibody IPH2101 in patients with relapsed/refractory multiple myeloma. Blood 120(22):4324-33.
Campbell KS, et al. (2011) Structure/function of human killer cell immunoglobulin-like receptors: lessons from polymorphisms, evolution, crystal structures and mutations. Immunol 132(3):315-25.
Chan HW, et al. (2003) DNA methylation maintains allele-specific KIR gene expression in human natural killer cells. J Exp Med 197(2):245-55.

(Continued)

*Primary Examiner* — Mark Halvorson
*Assistant Examiner* — Dennis J Sullivan
(74) *Attorney, Agent, or Firm* — Ashton J. Delauney

(57) ABSTRACT

This disclosure provides a method for treating a pediatric subject afflicted with acute B cell precursor leukemia (BCP-ALL) comprising administering to the subject an anti-killer cell immunoglobulin-like receptor (KIR) antibody or an antigen-binding portion thereof that binds specifically to an inhibitory KIR and blocks inhibitory KIR activity, thereby potentiating NK cell lytic activity. An exemplary anti-KIR antibody for use in this method is lirilumab. The disclosure also provides a kit for treating a subject afflicted with pediatric BCP-ALL, the kit comprising a dosage ranging from 0.01 to 20 mg/kg body weight of an anti-KIR antibody or an antigen-binding portion thereof that specifically binds to an inhibitory KIR and blocks inhibitory KIR activity, and instructions for using the anti-KIR antibody or an antigen-binding portion thereof in any of the disclosed methods for treating pediatric BCP-ALL.

15 Claims, 40 Drawing Sheets
Specification includes a Sequence Listing.

(56) References Cited

OTHER PUBLICATIONS

Colucci F, et al. (2003) What does it take to make a natural killer cell? Nat Rev Immunol 3(5):413-25.
Colucci F, et al. (2001) Differential requirement for the transcription factor PU.1 in the generation of natural killer cells versus B and T cells. Blood 97(9):2625-32.
Cooley S, et al. (2010) Donor selection for natural killer cell receptor genes leads to superior survival after unrelated transplantation for acute myelogenous leukemia. Blood 116(14):2411-9.
Curik N, et al. (2012) 5-azacitidine in aggressive myelodysplastic syndromes regulates chromatin structure at PU.1 gene and cell differentiation capacity. Leukemia 26(8):1804-11.
De Lima M, et al. (2010) Maintenance therapy with low-dose azacitidine after allogeneic hematopoietic stem cell transplantation for recurrent acute myelogenous leukemia or myelodysplastic syndrome: a dose and schedule finding study. Cancer 116(23):5420-31.
Farag SS, et al. (2002) Natural killer cell receptors: new biology and insights into the graft-versus-leukemia effect. Blood 100(6):1935-47.
Fernandez NC, et al. (2005) A subset of natural killer cells achieves self-tolerance without expressing inhibitory receptors specific for self-MHC molecules. Blood 105(11):4416-23.
Feuchtinger T, et al. (2009) Cytolytic activity of NK cell clones against acute childhood precursor-B-cell leukaemia is influenced by HLA class I expression on blasts and the differential KIR phenotype of NK clones. Bone Marrow Transplant 43(11):875-81.
Freud AG, et al. (2006) Evidence for discrete stages of human natural killer cell differentiation in vivo. J Exp Med 203(4):1033-43.
Frikeche J, et al. (2011) Impact of the hypomethylating agent 5-azacytidine on dendritic cells function. Exp Hematol 39(11):1056-63.
Fujisaki H, et al. (2009) Expansion of highly cytotoxic human natural killer cells for cancer cell therapy. Cancer Res 69(9):4010-7.
Gao XN, et al. (2009) Demethylating treatment suppresses natural killer cell cytolytic activity. Mol Immunol 46(10):2064-70.
Hagemann S, et al. (2011) Azacytidine and decitabine induce gene-specific and non-random DNA demethylation in human cancer cell lines. PLoS One 6(3):e17388.
Kübler A, et al. (2014). Both mature KIR+ and immature KIR-NK cells control pediatric acute B cell precursor leukemia in NOD.Cg-Prkdcscid IL2rgtmWjl/Sz mice. Blood 124(26):3914-23.
Leung W, et al. (2004) Determinants of antileukemia effects of allogeneic NK cells. J Immunol 172(1):644-50.
Lübbert M, et al. (2010) Efficacy of a 3-day, low-dose treatment with 5-azacytidine followed by donor lymphocyte infusions in older patients with acute myeloid leukemia or chronic myelomonocytic leukemia relapsed after allografting. Bone Marrow Transplant 45(4):627-32.
Mengarelli A, et al. (2001) Adhesion molecule expression, clinical features and therapy outcome in childhood acute lymphoblastic leukemia. Leuk Lymphoma 40(5-6):625-30.
Miller JS, et al. (2005) Successful adoptive transfer and in vivo expansion of human haploidentical NK cells in patients with cancer. Blood 105(8):3051-7.
Moretta L, et al. (2011) Killer Ig-like receptor-mediated control of natural killer cell alloreactivity in haploidentical hematopoietic stem cell transplantation. Blood 117(3):764-71.
Nguyen S, et al. (2005) NK-cell reconstitution after haploidentical hematopoietic stem-cell transplantations: immaturity of NK cells and inhibitory effect of NKG2A override GvL effect. Blood 105(10):4135-42.
Orr MT, et al (2011) Unlicensed natural killer cells dominate the response to cytomegalovirus infection. Nat Immunol 11(4):321-7.
Pende D, et al. (2009) Anti-leukemia activity of alloreactive NK cells in KIR ligand-mismatched haploidentical HSCT for pediatric patients: evaluation of the functional role of activating KIR and redefinition of inhibitory KIR specificity. Blood 113(13):3119-29.
Pende D, et al. (2005) Analysis of the receptor-ligand interactions in the natural killer-mediated lysis of freshly isolated myeloid or lymphoblastic leukemias: evidence for the involvement of the Poliovirus receptor (CD155) and Nectin-2 (CD112). Blood 105(5):2066-73.
Pfeiffer M, et al. (2007) Intensity of HLA class I expression and KIR-mismatch determine NK-cell mediated lysis of leukaemic blasts from children with acute lymphatic leukaemia. Br J Haematol 138:97-100.
Pfeiffer MM, et al. (2012) IL-15-stimulated CD3/CD19-depleted stem-cell boosts in relapsed pediatric patients after haploidentical SCT. Leukemia 26(11):2435-9.
Romagne F et al. (2009) Preclinical characterization of 1-7F9, a novel human anti-KIR receptor therapeutic antibody that augments natural killer-mediated killing of tumor cells. Hematology 114(13): pp. 2667-2677.
Rubnitz JE, et al. (2010) NKAML: a pilot study to determine the safety and feasibility of haploidentical natural killer cell transplantation in childhood acute myeloid leukemia. J Clin Oncol 28(6):955-9.
Ruggeri L, et al. (1999) Role of natural killer cell alloreactivity in HLA-mismatched hematopoietic stem cell transplantation. Blood 94(1):333-9.
Ruggeri L, et al. (2002) Effectiveness of donor natural killer cell alloreactivity in mismatched hematopoietic transplants. Science 295(5562):2097-100.
Santourlidis S, et al. (2002) Crucial role of DNA methylation in determination of clonally distributed killer cell Ig-like receptor expression patterns in NK cells. J Immunol 169(8):4253-61.
Schmiedel BJ, et al. (2011) Azacytidine impairs NK cell reactivity while decitabine augments NK cell responsiveness toward stimulation. Int J Cancer 128(12):2911-22.
Strowig T, et al. (2010) Human NK cells of mice with reconstituted human immune system components require pre-activation to acquire functional competence. Blood 116(20):4158-67.
Vago L, et al. (2008) Temporal, quantitative, and functional characteristics of single-KIR-positive alloreactive natural killer cell recovery account for impaired graft-versus-leukemia activity after haploidentical hematopoietic stem cell transplantation. Blood 112(8):3488-99.
Vey N, et al. (2012) A phase 1 trial of the anti-inhibitory KIR mAb IPH2101 for AML in complete remission. Blood 120(22):4317-23.
Woiterski J, et al. (2013) Engraftment of low numbers of pediatric acute lymphoid and myeloid leukemias into NOD/SCID/IL2Rγnull mice reflects individual leukemogenecity and highly correlates with clinical outcome. Int J Cancer 133(7):1547-56.
Benson DM et al. (2013) Anti-KIR strategy in cancer treatment. Drugs Fut 38(2):99-105.

* cited by examiner

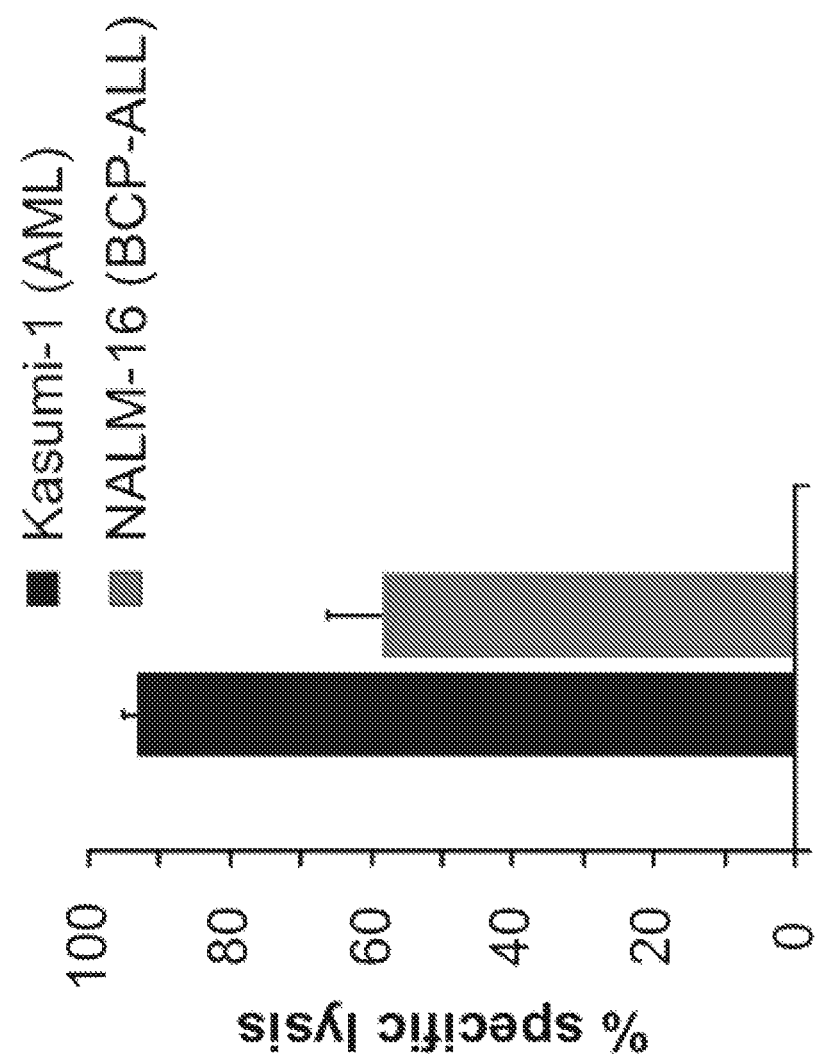

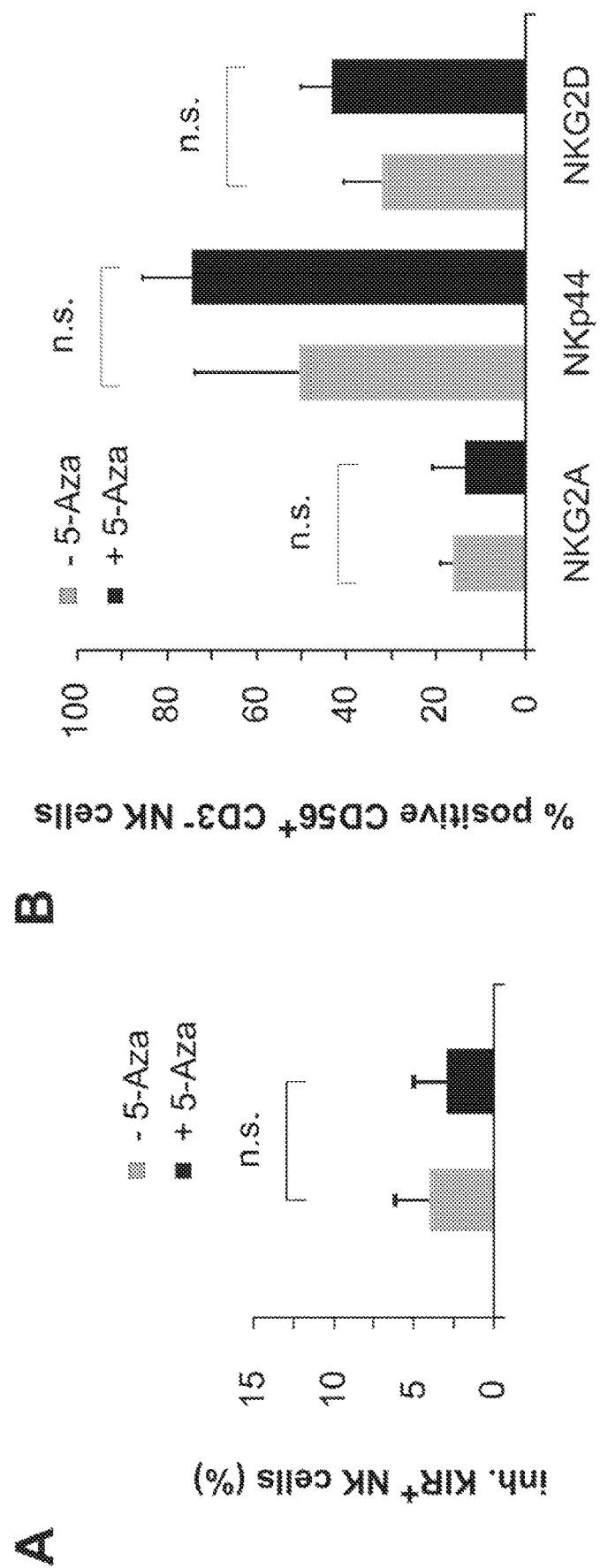
FIGS. 11A and B

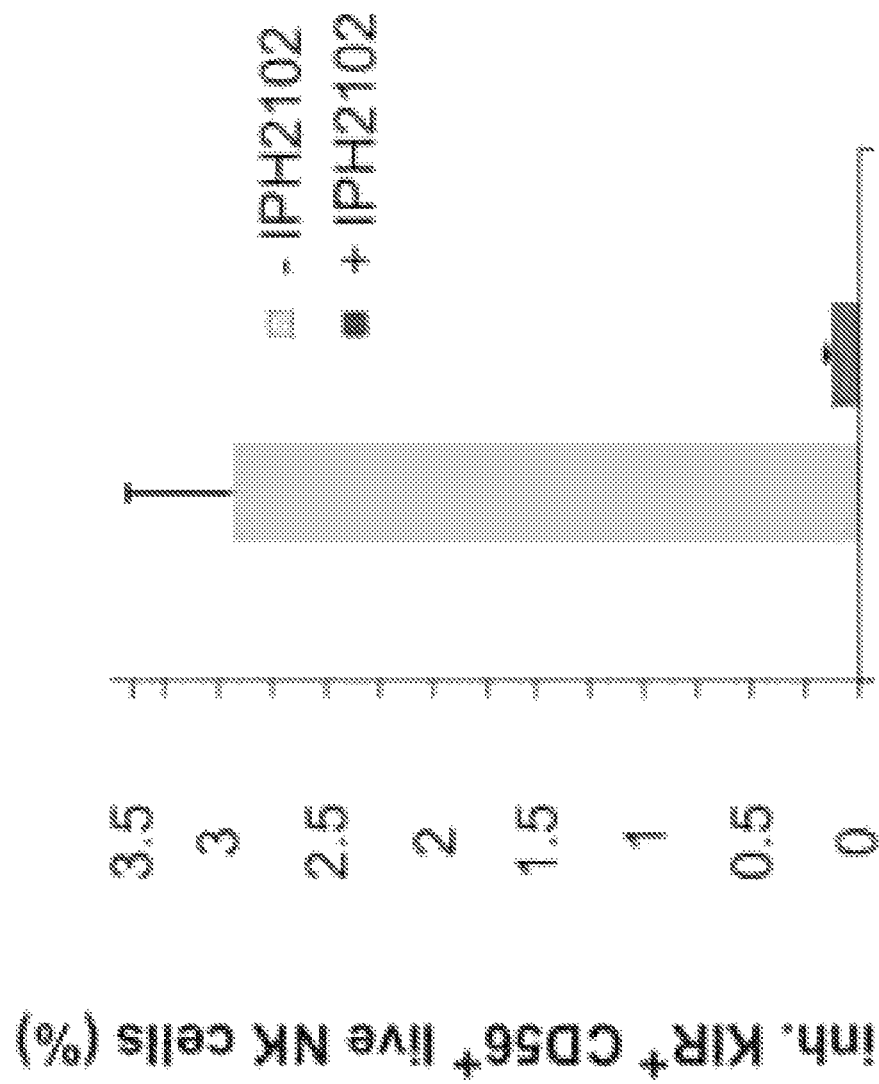

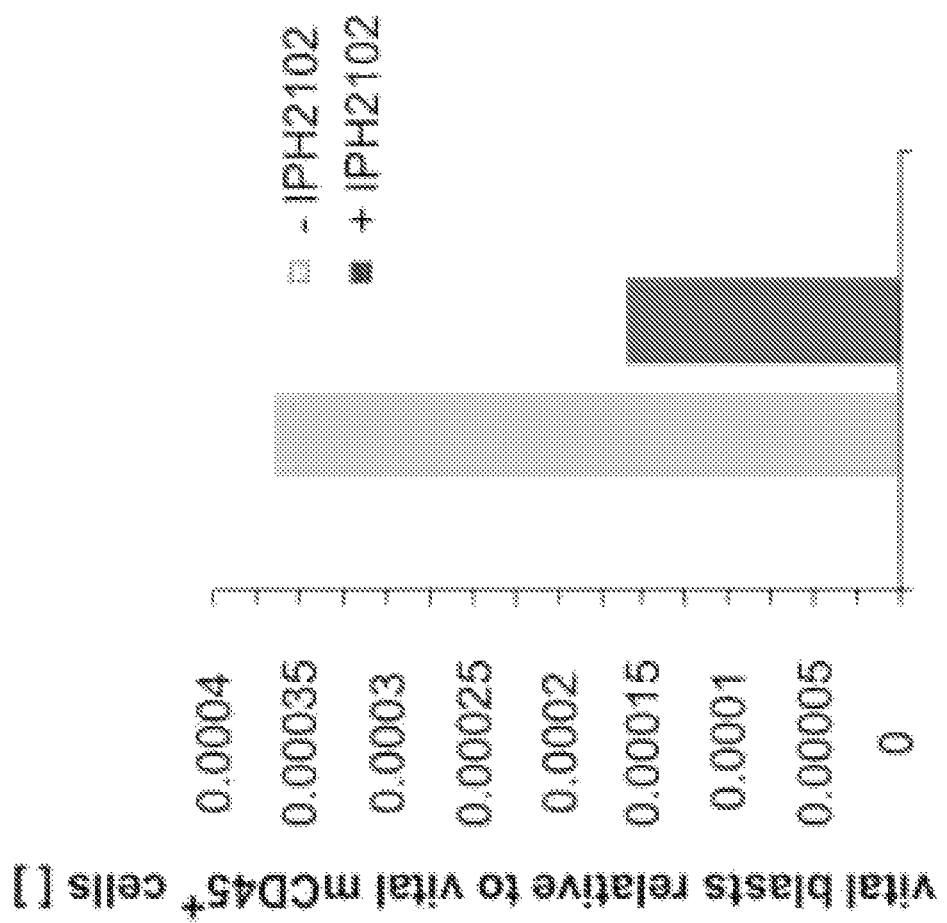

TREATMENT OF PEDIATRIC BCP-ALL PATIENTS WITH AN ANTI-KIR ANTIBODY

CROSS REFERENCE TO RELATED APPLICATIONS

This application is a U.S. national phase application under 35 U.S.C. § 371 of International Patent Application No. PCT/US2015/057565, filed Oct. 27, 2015, which claims the benefit of U.S. Provisional Application 62/069,478, filed Oct. 28, 2014, the contents of each of which are hereby incorporated herein by reference in their entirety.

Throughout this application, various publications are referenced in parentheses by author name and date, or by Patent No. or Patent Publication No. Full citations for these publications may be found at the end of the specification immediately preceding the claims. The disclosures of these publications are hereby incorporated in their entireties by reference into this application in order to more fully describe the state of the art as known to those skilled therein as of the filing date of the application. However, the citation of a reference herein should not be construed as an acknowledgement that such reference is prior art to the disclosed invention.

FIELD OF THE INVENTION

The invention disclosed herein relates to methods for treating B-Cell Precursor Acute Lymphoblastic Leukemia (BCP-ALL) in a pediatric patient comprising administering to the patient an anti-Killer cell Immunoglobulin-like Receptor (anti-KIR) antibody.

BACKGROUND OF THE INVENTION

Natural killer (NK) cells are a sub-population of mononuclear lymphocytes, involved in immunity and in the host immune surveillance system. Their biological properties include the ability to bind to and kill target cells that fail to express "self" major histocompatibility complex (MHC)/ human leukocyte antigen (HLA) proteins, and the ability to kill tumor cells or other diseased cells that express ligands for activating NK receptors. Thus, NK cells are characterized by their ability to bind to and kill several types of tumor cell lines without the need for prior immunization or activation.

Various therapeutic and vaccine strategies have been proposed based on a modulation of NK cell activity. However, NK cell activity is regulated by complex mechanisms that involve both stimulating and inhibitory signals. An important set of regulatory receptors is the HLA class I-restricted, killer cell immunoglobulin-like receptor (KIR) family which comprises both inhibitory and activating family members that recognize allotypic variants of HLA class I alleles as KIR ligands (KIRL). The NK cells of a single individual typically express different combinations of KIRs, providing a repertoire of NK cells with different specificities for HLA class I molecules.

In the setting of haplo-identical hematopoietic stem cell transplantation (HSCT), NK cells maturing in a HLA-disparate recipient will be shaped in the predominantly donor-type-like hematopoietic niche and will thus be donor-tolerant and recipient-"alloreactive," at least during the first months after reconstitution (Leung et al., 2004; Moretta et al., 2011; Pende et al., 2009). In this regard, the beneficial effects of promoting a certain degree of donor-recipient HLA-disparity was initially described by the Perugia group (Ruggeri et al., 1999; 2002) which provided evidence that allogeneic HSCTs performed with grafts from KIR-KIRL-mismatched donors promoted NK cell alloreactivity, mediating potent, life-saving anti-tumor responses and enhanced survival rates in adult patients with acute myeloid leukemia (AML). The underlying mechanism is believed to be that HLA-mismatched HSCT leads to the expansion of donor-derived NK cells expressing KIRs which do not recognize any HLA ligands in the recipient, and thus are not inhibited via KIR. One way of reproducing this effect by pharmacological treatment of a patient would be to administer reagents that block the KIR-HLA interaction to activate the patient's endogenous NK cells. Monoclonal antibodies (mAbs) that are cross-reactive with, and block the inhibitory activities of, the inhibitory KIR2DL1, 2DL2 and 2DL3 receptors have been developed (see, e.g., PCT Publication Nos. WO 2006/003179; WO 2008/084106) and have been undergoing clinical trials for treating various disseminated as well as solid tumors (Benson et al., 2012; Vey et al., 2012; see also clinicaltrials.gov/ct2/results?term=iph2101&Search=Search; clinicaltrials.gov/ct2/results?term=lirilumab&Search=Search).

B-cell precursor acute lymphoblastic leukemia (BCP-ALL) is the most common form of cancer in children and adolescents, accounting for ~20% of cancers in patients younger than 20 years of age (Howlader et al., 2015). Despite remarkable progress made in treatment of this disease over the past two decades, during which 5-year overall survival (OS) rates reached greater than 90%, the prognosis for infants less than 1 year of age at diagnosis and patients who suffer a relapse remains poor (Pui et al., 2009; Hunger et al., 2012). The strong anti-tumor response seen in AML patients treated with KIR-KIRL-mismatched haplo-identical transplants was not observed in BCP-ALL patients. As a result of this apparent resistance of adult BCP-ALL to NK cell-mediated lysis, the utility of NK cell immune-responses in treating BCP-ALL has been doubted and research in this field has largely been neglected. However, recent data indicate that the disease entity of pediatric BCP-ALL might yet be a target of "alloreactive" NK cells (Leung et al., 2004; Moretta et al., 2011; Feuchtinger et al., 2009; Pfeiffer et al., 2007; 2012). Considering the various potential facets of NK cell immune therapy such as adoptive transfer of mature NK cells, co-transfer of mature NK cells during graft manipulation, emergence of immature NK cells early post transplantation, administration of drugs that block inhibitory KIRs and thereby stimulate NK cell activity, and the currently existing limited number of clinical studies in BCP-ALL-bearing children, the present disclosure illuminates conditions under which NK cell-mediated alloreactivity can be exploited to treat poor-prognosis, pediatric BCP-ALL patients (see, also, Kübler et al., 2014). The problem to be solved is the provision of an alternative treatment for BCP-ALL that is effective in pediatric patients including, especially, patients under 1 year of age. This disclosure teaches that treatment with an Ab that inhibits the activity of inhibitory KIR receptors is effective in treating pediatric patients afflicted with BCP-ALL.

SUMMARY OF THE INVENTION

The present disclosure provides a method for treating a pediatric subject afflicted with BCP-ALL comprising administering to the subject an anti-KIR Ab or an antigen-binding portion thereof that binds specifically to an inhibitory KIR and blocks inhibitory KIR activity, thereby potentiating NK cell lytic activity. In certain preferred embodiments of any of the therapeutic methods disclosed herein, the anti-KIR Ab or antigen-binding portion thereof is cross-reactive with, and blocks the activity of the inhibitory KIRs, KIR2DL1 and KIR2DL2/3. In certain other preferred embodiments, the anti-KIR Ab or antigen-binding portion thereof does not bind to KIR2DS4. In further embodiments, the anti-KIR Ab or antigen-binding portion thereof further does not bind to KIR2DS3. In certain embodiments, the anti-KIR Ab or antigen-binding portion thereof cross-competes with lirilumab or an antigen-binding portion thereof for binding to human KIR2DL1 and/or KIR2DL2/3. In other embodiments, the anti-KIR Ab or antigen-binding portion thereof is lirilumab or an antigen-binding portion thereof.

The disclosure also provides a kit for treating a subject afflicted with acute pediatric BCP-ALL, the kit comprising: (a) a dosage ranging from 0.001 to 20 mg/kg body weight of an anti-KIR antibody or an antigen-binding portion thereof that specifically binds to an inhibitory KIR and blocks inhibitory KIR activity; and (b) instructions for using the anti-KIR antibody or an antigen-binding portion thereof in the method of any one of the preceding claims.

Other features and advantages of the instant invention will be apparent from the following detailed description and examples which should not be construed as limiting. The contents of all cited references, including scientific articles, newspaper reports, GenBank entries, patents and patent applications cited throughout this application are expressly incorporated herein by reference.

DETAILED DESCRIPTION OF THE INVENTION

Figure 1A:
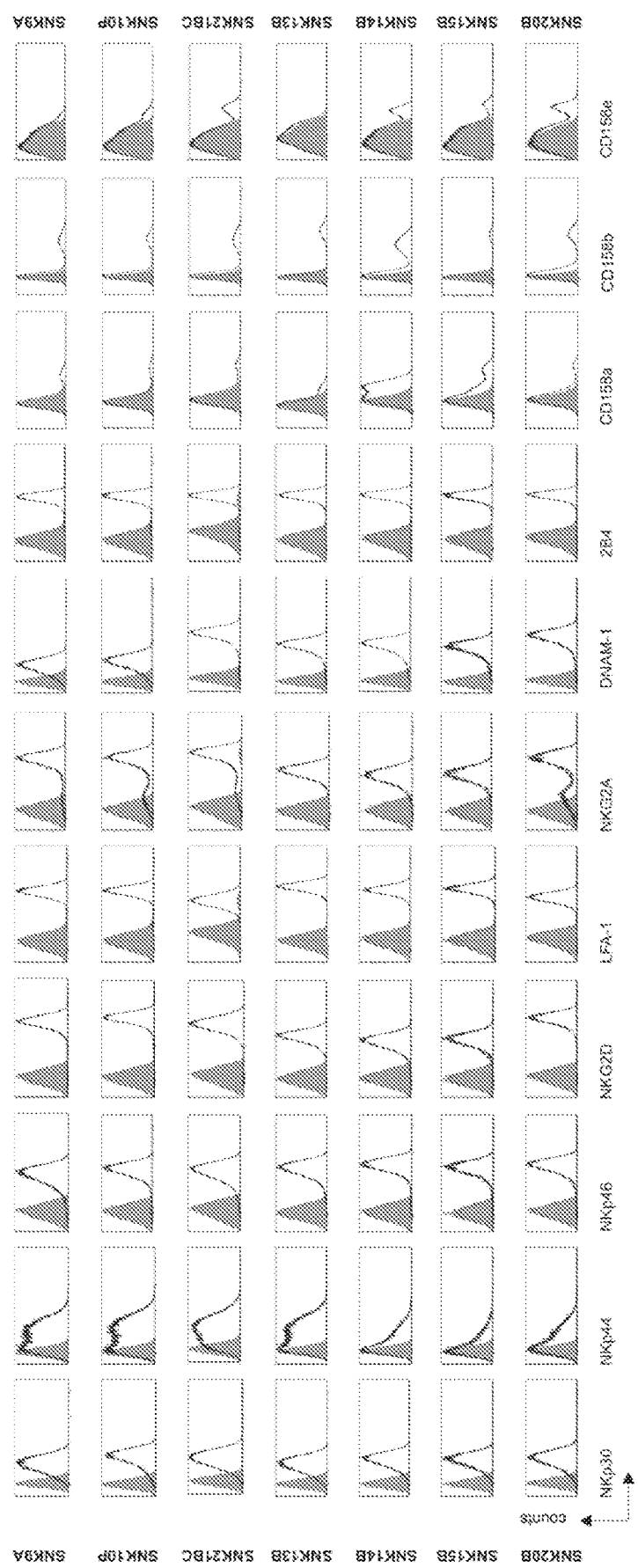
FIG. 1. Phenotypic characterization of donor NK cell receptor and patient NK cell receptor ligand repertoires. A: Receptor expression of selected important activating (NKp30, 44, 46, NKG2D, 2B4) and inhibitory (NKG2A, CD158a, b and e) NK cell receptors or adhesion molecules (LFA-1, DNAM-1), respectively, on NKAES cells of the studied donors. B: Flow-cytometric characterization of the expression of HLA class I, ICAM-1, NKG2D ligands (NKG2DL) or DNAM-1 ligands (CD112, CD155) on various BCP-ALL cell lines or primary specimen. For comparison, K562 cells and one pediatric AML cell line (Kasumi-1) are included. Pan-NKG2DL indicates staining with a cocktail of anti-MICA, -MICB and -ULBP1-3 antibodies. Data show staining with the indicated antigen-specific antibody (Ab) (open) or the corresponding isotype controls (filled).

Disclosed herein are methods for treating a pediatric patient afflicted with BCP-ALL comprising administering to the patient an anti-inhibitory KIR Ab.

Terms

In order that the present disclosure may be more readily understood, certain terms are first defined. As used in this application, except as otherwise expressly provided herein, each of the following terms shall have the meaning set forth below. Additional definitions are set forth throughout the application.

"Administering" refers to the physical introduction of a therapeutic agent to a subject using any of the various methods and delivery systems known to those skilled in the art. Preferred routes of administration for an anti-KIR Ab include intravenous, intramuscular, subcutaneous, intraperitoneal, spinal, via implant, or other parenteral routes of administration, for example by injection or infusion. The phrase "parenteral administration" as used herein means modes of administration other than enteral and topical administration, usually by injection.

An "antibody" (Ab) shall include, without limitation, a glycoprotein immunoglobulin (Ig) which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and an H chain constant region. The H chain constant region comprises three constant domains, $C_{H1}$, $C_{H2}$ and $C_{H3}$. Each L chain comprises a light chain variable region (abbreviated herein as $V_L$) and an L chain constant region. The L chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the H and L chains contain a binding domain that interacts with an antigen. The constant regions of the Abs may mediate the binding of the Ig to host tissues or factors, including various cells of the immune system (e.g., effector cells) and the first component (Clq) of the classical complement system.

An Ig may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the H chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or antigen-binding portion of any of the aforementioned Ig's, and includes a monovalent and a divalent fragment or portion, and a single chain Ab.

An "isolated antibody" refers to an Ab that is substantially free of other Abs having different antigenic specificities (e.g., an isolated Ab that binds specifically to KIR2DL1 is substantially free of Abs that bind specifically to antigens other than KIR2DL1). An isolated Ab that binds specifically to KIR2DL1 may, however, have cross-reactivity to other antigens, such as KIR2DL2/3 polypeptides. For example, DF200 and lirilumab are murine and human mAbs, respectively, that are cross-reactive with KIR2DL1, -2, and -3. Moreover, an "isolated" Ab may be an Ab that is substantially free of other cellular material and/or chemicals.

The term "monoclonal antibody" (mAb) refers to a non-naturally occurring preparation of Ab molecules of single molecular composition, i.e., Ab molecules whose primary sequences are essentially identical, and which exhibit a single binding specificity and affinity for a particular epitope. A mAb is an example of an isolated Ab. MAbs may be produced by hybridoma, recombinant, transgenic or other techniques known to those skilled in the art.

A "human" monoclonal antibody (HuMAb) refers to an Ab having variable regions in which both the framework and CDR regions are derived from human germline Ig sequences. Furthermore, if the Ab contains a constant region, the constant region also is derived from human germline Ig sequences. The human Abs of the invention may include amino acid residues not encoded by human germline Ig sequences (e.g., mutations introduced by random or site-specific mutagenesis in vitro or by somatic mutation in vivo). However, the term "human antibody," as used herein, is not intended to include Abs in which CDR sequences derived from the germline of another mammalian species, such as a mouse, have been grafted onto human framework sequences. The terms "human" Abs and "fully human" Abs and are used synonymously.

A "humanized" antibody refers to an Ab in which some, most or all of the amino acids outside the CDR domains of a non-human Ab are replaced with corresponding amino acids derived from human Ig's. In one embodiment of a humanized form of an Ab, some, most or all of the amino acids outside the CDR domains have been replaced with amino acids from human Ig's, whereas some, most or all amino acids within one or more CDR regions are unchanged. Small additions, deletions, insertions, substitutions or modifications of amino acids are permissible as long as they do not abrogate the ability of the Ab to bind to a particular antigen. A humanized Ab retains an antigenic specificity similar to that of the original Ab.

A "chimeric" antibody refers to an Ab in which the variable regions are derived from one species and the constant regions are derived from another species, for example, an Ab in which the variable regions are derived from a mouse Ab and the constant regions are derived from a human Ab.

An "anti-antigen" Ab refers to an Ab that binds to the antigen with high specificity and/or affinity. For example, an anti-KIR2DL1 Ab binds specifically to KIR2DL1 and an anti-KIR2DL2/3 Ab binds specifically to KIR2DL2/3. A single Ab may be cross-reactive with more than one antigen. A "cross-reactive" Ab refers to an Ab that binds to more than one antigen with high specificity and/or affinity. For example, lirilumab is a cross-reactive anti-KIR Ab that binds specifically and with high affinity to both KIR2DL1 and KIR2DL2/3.

An "antigen-binding portion" of an Ab (also called an "antigen-binding fragment") refers to one or more fragments of an Ab that retain the ability to bind specifically to the antigen bound by the whole Ab. An antigen-binding Ab portion typically exhibits the same functional properties of the whole or full-length Ab where these functional properties depend on the binding specificity of the Ab.

The ability of an anti-KIR Ab to "block" the binding of a KIR receptor and its cognate HLA ligand means that the Ab, in an assay using soluble or cell-surface associated KIR and HLA molecules, can detectably reduce the binding of the KIR to the HLA molecule in a dose-dependent fashion, where the KIR detectably binds to the HLA ligand in the absence of the Ab. In certain embodiments, the Ab reduces the binding of the KIR to the HLA molecule by more than about 10%. In preferred embodiments, the Ab reduces the binding of the KIR to the HLA molecule by at least about 20%, or at least about 50%. In more preferred embodiments, the Ab reduces binding by at least about 75%, at least about 90%, or essentially about 100% relative to the binding of the KIR to the HLA molecule in the absence of the Ab.

A "cancer" refers a broad group of various diseases characterized by the uncontrolled growth of abnormal cells in the body. Unregulated cell division and growth result in the formation of malignant tumors that invade neighboring tissues and may also metastasize to distant parts of the body through the lymphatic system or bloodstream.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

A "KIR" (Killer cell Immunoglobulin-like Receptor or, more simply, Killer Inhibitory Receptor) refers to a protein or polypeptide receptor encoded by a gene or cDNA that is a member of the KIR gene family (see Campbell and Purdy, 2011), which inhibits NK cell activation on binding to their ligands, principally HLA-C molecules (Farag et al., 2002). The sequences of human KIR genes and cDNAs, as well as their protein products, are available in public databases, including GenBank. Non-limiting examples of human KIRs include: KIR2DL1, GenBank Accession No. U24076, NM_014218, AAR16197, or L41267; KIR2DL2, GenBank Accession No. U24075 or L76669; KIR2DL3, GenBank Accession No. U24074 or L41268; KIR2DL4, GenBank Accession No. X97229; KIR2DS1: GenBank Accession No. X89892; KIR2DS2, GenBank Accession No. L76667; KIR2DS3, GenBank Accession No. NM_012312 or L76670 (splice variant); KIR2DS4, GenBank Accession No. AAR26325; and KIR3DL1, GenBank Accession No. L41269. A KIR may comprise from 1 to 3 extracellular domains, and may have a long (i.e., more than 40 amino acids) or short (i.e., less than 40 amino acids) cytoplasmic tail. The nomenclature for KIRs is based upon the number of extracellular domains (KIR2D and KIR3D having two and three extracellular Ig-domains, respectively) and whether the cytoplasmic tail is long (KIR2DL or KIR3DL) or short (KIR2DS or KIR3DS). The known inhibitory KIRs include members of the KIR2DL and KIR3DL subfamilies. Inhibitory KIRs having two Ig domains (KIR2DL) recognize HLA-C allotypes: KIR2DL2 (formerly designated p58.2) and the closely related, allelic gene product KIR2DL3 both recognize "group 1" HLA-C allotypes (including HLA-Cw1, -3, -7, and -8), whereas KIR2DL1 (p58.1) recognizes "group 2" HLA-C allotypes (such as HLA-Cw2, -4, -5, and -6).

A "KIR2DL" receptor(s) refers to any one, two or all of the inhibitory KIR2DL1, KIR2DL2 and KIR2DL3 receptors.

The term "KIR2DL2/3" refers to either or both of the KIR2DL2 and KIR2DL3 receptors. These two receptors have a very high homology, are allelic forms of the same gene, and have identical ligand binding specificity, and are therefore considered in the art and herein to be functionally similar variants of the same receptor.

A "neutralizing" anti-KIR Ab or an anti-KIR Ab that "reduces, neutralizes or reverses the inhibitory activity of a KIR," "reduces, neutralizes or reverses inhibition of NK cell cytotoxicity," "potentiates NK cell activity," or "potentiates NK cell cytotoxicity" means an anti-KIR Ab that enhances the ability of an NK cell expressing a KIR receptor to lyse target cells expressing on their surface a particular MHC or HLA molecule that is a ligand for the KIR. Potentiation of NK cytotoxicity means any substantial potentiation, or at least about 10%, at least about 25%, at least about 50% potentiation of NK cytotoxicity, to more than about 100%, more than about 500%, more than about 1000% increase in cytotoxicity.

A "subject" includes any human or nonhuman animal such as a primate (e.g., a monkey), mouse, rat, guinea pig or rabbit. In preferred embodiments, the subject is a human. The terms "subject," "patient" and "individual" are used interchangeably herein.

A "therapeutically effective amount" or "therapeutically effective dosage" of a drug or therapeutic agent means an amount sufficient to treat a subject afflicted with a disorder or a complication associated with a disorder, wherein the drug or therapeutic agent is administered alone or in combination with another drug or anti-cancer therapy. The therapeutically effective amount can be determined using a variety of methods known to the skilled practitioner, such as in human subjects during clinical trials, in animal model systems predictive of efficacy in humans, or by assaying the activity of the agent in in vitro assays. The terms "effective" and "effectiveness" with regard to a treatment includes both pharmacological effectiveness and physiological safety. Pharmacological effectiveness in the context of the therapeutic methods described herein refers to the ability of the drug to promote cancer regression in a patient. Physiological safety refers to the level of toxicity or other adverse physiological effects at the cellular, organ and/or organism level (adverse effects) resulting from administration of the drug.

By way of example for the treatment of tumors, a therapeutically effective amount of a drug or anti-cancer agent preferably inhibits tumor growth by at least about 20%, more preferably by at least about 40%, even more preferably by at least about 60%, and still more preferably by at least about 80% relative to untreated subjects. In other preferred embodiments, a therapeutically effective amount of the drug essentially completely inhibits tumor growth. In certain embodiments, tumor regression may be observed and continue for a period of at least about 20 days, at least about 40 days, or at least about 60 days. In preferred embodiments, tumor regression continues for at least about 3 months, at least about 6 months, or at least about a year. In more preferred embodiments, tumor regression continues for many years, for example, at least about 2 years, at least about 5 years, or at least about 10 years. Notwithstanding these ultimate measurements of therapeutic effectiveness, evaluation of immunotherapeutic drugs must also make allowance for "immune-related" response patterns.

An "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents may require long-term monitoring of the effects of these agents on the target disease.

A therapeutically effective amount of a drug includes a "prophylactically effective amount," which is any amount of the drug that, when administered alone or in combination with another anti-neoplastic treatment to a subject at risk of developing a cancer (e.g., a subject having a pre-malignant condition) or of suffering a recurrence of cancer, inhibits the development or recurrence of the cancer. In preferred embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

The use of the alternative (e.g., "or") should be understood to mean either one, both, or any combination thereof of the alternatives. As used herein, the indefinite articles "a" or "an" should be understood to refer to "one or more" of any recited or enumerated component.

The term "about," "essentially" or "comprising essentially of" refers to a value or composition that is within an acceptable error range for the particular value or composition as determined by one of ordinary skill in the art, which will depend in part on how the value or composition is measured or determined, i.e., the limitations of the measurement system. For example, "about," "essentially" or "comprising essentially of" can mean within 1 or within more than 1 standard deviation per the practice in the art. Alternatively, "about," "essentially" or "comprising essentially of" can mean a range of plus or minus 20%, more usually a range of plus or minus 10%. Furthermore, particularly with respect to biological systems or processes, the terms can mean up to an order of magnitude or up to 5-fold of a value. When particular values or compositions are provided in the application and claims, unless otherwise stated, the meaning of "about," "essentially" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the invention are described in further detail in the following subsections.

Anti-Inhibitory KIR Antibodies

The NK cell-mediated anti-tumor responses observed in AML patients treated with allogeneic HSCT grafts from KIR-KIRL-mismatched donors can, in principle, be reproduced by treating the patient with an agent that blocks the KIR-HLA interaction to thereby potentiate endogenous NK cell lytic activity. MAb EB6 has been shown to bind specifically to KIR2DL1 (p58.1) and block the interaction of KIR2DL1 with "group 2" HLA-C allotypes, such as HLA-Cw4, and to promote NK-mediated lysis of target cells that express those HLA-C allotypes (Moretta et al., 1990). MAb GL83, which is specific for KIR2DL2/3 and blocks the interaction of KIR2DL2/3 with HLA-Cw3 or similar "group 1" allotypes has also been described (Moretta et al., 1990). MAb HP-3E4 (Melero et al., 1994), which specifically binds to KIR2DL1 and KIR2DS2, and mAb CH-L (Ferrini et al., 1994), which specifically binds to KIR2DL2/3 and KIR2DS2, also block inhibitory KIR signaling. These four mAbs are murine Abs that are unsuitable for therapeutic use in human because they could provoke a human anti-mouse Ab (HAMA) response. Such Abs have the added disadvantage in clinical situations that they would be therapeutically effective only in a subset of patients who express group 1 or group 2 HLA-C allotypes.

The latter disadvantage can be circumvented by using Abs that are cross-reactive with both KIR2DL1 and KIR2DL2/3. Cross-reactive Abs have been described in the art. For example, Watzl et al. (2000) produced a cross-reactive murine Ab, Lig1, that recognizes KIR2DL1 and KIR2DL2/3 as well as MIR2DS1-5, but this Ab did not potentiate the lytic activity of NK cells. Spaggiari et al. (2002a; b) identified a murine Ab, NKVSF1 (also known as Pan2D; commercially available from, e.g., AbD Serotec, Catalog No. MCA2243), which was reported to recognize a common epitope of KIR2DL1 (CD158a), KIR2DL2 (CD158b) and KIR2DS4 (p50.3). Similarly, Shin et al. (1999) reported the production of two mAbs, A210 and A803g, each capable of binding to KIR2DL1, KIR2DL3, and KIR2DS4. However, none of these Abs that was cross-reactive with both KIR2DL1 and KIR2DL2/3 was shown to potentiate NK cell lytic activity. The above-described anti-KIR2DL mAbs therefore appeared to fall into two categories: (1) Abs that cross-react with different KIR2DL polypeptides but do not block inhibitory KIR signaling, and (2) Abs that increase NK cell cytotoxicity but do not cross-react with different KIR2DL polypeptides. The properties of these Abs suggested that a "cross-reactive KIR2DL" epitope would not be a site involved in inhibitory signaling and, conversely, no epitope that was involved in inhibitory signaling would be common to KIR2DL1 and KIR2DL2/3.

The previously known anti-KIR2DL Abs also suffered the disadvantage that they often bound to multiple activating KIR2DS receptors. For therapeutic use of an Ab in blocking the inhibitory KIRs of a patient's NK cells, it is desirable that the Ab also bind to few activating KIR receptors since blockade of activating receptors could impair the stimulation of NK cells. Thus, an Ab having the antigen-binding characteristics of NKVSF1, A210 or A803g would not be optimal in a clinical setting for the additional reason that they all bind to the activating KIR2DS4 receptor.

Notwithstanding the implications from characterization of the initially isolated anti-KIR2DL Abs that cross-reactivity may be incompatible with potentiation of NK cell cytotoxicity, mAbs that both cross-react with KIR2DL1 and KIR2DL2/3 and potentiate NK cell lytic activity have subsequently been isolated and characterized.

KIR2DL1- and KIR2DL2/3-Cross-Reactive Abs that Increase NK Cell Cytotoxicity

Novel Abs that cross-react with at least the KIR2DL1 and KIR2DL2/3 receptors and neutralize their inhibitory signals, resulting in potentiation of NK cell cytotoxicity in NK cells expressing these inhibitory KIR receptors, are disclosed in PCT Publication No. WO 2005/003168. Because at least one of KIR2DL1 or KID2DL2/3 is present in about 90% or more of the human population, the KIR2DL1- and KIR2DL2/3-cross-reactive mAbs disclosed in WO 2005/003168 are capable of stimulating NK cell activity against most of the HLA-C allotype-associated cells, respectively group 1 and group 2 HLA-C allotypes. Thus, compositions comprising the Ab may be used to effectively activate or potentiate NK cell activity in most human individuals. Cross-reactive Abs exemplified in WO 2005/003168 that strongly potentiate NK cell cytolytic activity on HLA-Cw3$^+$ and HLA-Cw4$^+$ targets include the murine mAb, DF200 (hybridoma deposited at the CNCM culture collection, under Registration No. CNCM I-3224, registered Jun. 10, 2004, Collection Nationale de Cultures de Microorganismes, Institut Pasteur, 25 Rue du Docteur Roux, F-75724 Paris Cedex 15, France) or a Fab or F(ab')$_2$ fragment thereof, and the human Ab, 1-7F9 (also known as IPH2101). Other exemplified human Abs that recognize both KIR2DL1 and KID2DL2/3, including 1-4F1, 1-6F5 and 1-6F1, exhibit lower levels of NK cell activation. WO 2005/003168 discloses in Example 4 that these Abs were not able to "reconstitute cell lysis" by NK cells against Cw4-positive targets, in contrast to 1-7F9 which almost completely reconstitutes lysis of HLA-ligand expressing targets to the level seen in a positive control YTS-Eco target that has no HLA ligand for the KIRs. Notably, however, FIG. 5 in WO 2005/003168 actually shows that 1-4F1, 1-6F5 and 1-6F1 exhibited a level of NK-mediated lytic activity that was significantly above that of a negative control and was, in fact, comparable to that of reference murine mAb, EB6, which is used in the scientific literature as a blocking Ab for KIR2DL1. Additional analysis (data not shown) has demonstrated that mAb 1-4F1 induced a level of cytolytic activity against target cells expressing HLA-Cw3 comparable to the level induced by mAb DF200.

The method described in WO 2005/003168 for isolating Abs that bind to KIR2DL1- and KIR2DL2/3, but not to stimulatory KIR2DS4, and increase NK cell cytotoxicity is reproducible. Thus, in a subsequent immunization experiment to that described in WO 2005/003168, the disclosed protocol was followed comprising (a) immunizing RBF-mice with recombinant KIR2DL1 polypeptides followed by a boost with KIR2DL3 polypeptide, (b) screening supernatants by fluorometric microvolume assay technology (FMAT) for binding to KIR2DL1$^+$ YTS cells, (c) screening supernatants by fluorescence-activated cell sorting (FACS) for staining on BWZ-KIR2DL1, BWZ-KIR2DL3, BWZ-KIR2DS1, BWZ-KIR2DS2 and BWZ-KIR2DS4 cells; (d) testing supernatants for binding to immobilized KIR2DL1, KIR2DL3, KIR2DS1, KIR2DS2 and KIR2DS4 by enzyme-linked immunosorbent assay (ELISA) assay; and (e) performing $^{51}$Cr-release NK-cytotoxicity assays using YTS-2DL1 as effector cells and LCL 721.221-Cw4 as target cells, with wells having more than 10% specific killing of target cells being considered positive. The FMAT screen yielded approximately 400 supernatants. These supernatants were then evaluated for binding to KIR2D proteins and for induction of cytotoxicity. Most supernatants that were positive for binding to KIR2DL1 in the FMAT screen showed little binding to KIR2DL3. A subset of supernatants were identified that showed >10% cell killing in the cytotoxicity assay. Overall, 5 Abs, 26F16, 26F107, 26F117, 26F198 and 26F201 were identified as binding to both KIR2DL1, KIR2DL2/3 but not to KIR2DS4, and exhibiting >10% cell killing in the cytotoxicity assay.

Rescreening of the known mouse mAb, NKVSF1, also revealed that it was a KIR2DL1- and KIR2DL2/3-cross-reactive, neutralizing Ab.

HuMAbs 1-7F9 and Lirilumab 1-7F9 was further characterized in PCT Publication No. WO 2006/003179, including determination of its amino acid sequence. 1-7F9 is a KIR2DL-cross-reactive HuMAb, i.e., it is a fully human mAb that binds specifically to both KIR2DL1 and KIR2DL2/3. Further, unlike the murine KIR2DL-cross-reactive mAb NKVSF1, this HuMAb does not bind to the stimulatory KIR, KIR2DS4. Similar to NKVSF1, it also does not bind to the stimulatory KIR, KIR2DS3. 1-7F9 blocks the binding of at least one of KIR2DL1, KIR2DL2, and KIR2DL3 to an HLA-C class I molecule. Specifically, it blocks the binding of an HLA-Cw4 molecule to KIR2DL1, and the binding of an HLA-Cw3 molecule to at least one of KIR2DL2 or KIR2DL3. The Ab also potentiates the lytic activity of an NK cell against a human target cell expressing an HLA-C class I molecule. 1-7F9 was demonstrated to potentiate NK cell lytic activity to a greater extent than several other KIR2DL-cross-reactive mAbs including NKVSF1, DF200 and 1-4F1. The amino acid sequences of the V$_H$ and V$_L$ regions of 1-7F9 are shown as SEQ ID NOs.1 and 2, respectively. The amino acid sequence of the 1-7F9 H chain, which is of the IgG4 isotype, is shown as SEQ ID NO:3, whereas the amino acid sequence of the 1-7F9 L chain, which is a kappa L chain, is shown as SEQ ID NO:5.

1-7F9 (designated IPH2101) is undergoing clinical trials for the treatment of AML (see, e.g., Vey et al., 2012) and multiple myeloma (Benson et al., 2012). It has been shown that administration of 1-7F9 to cancer patients using a low dosage/frequency regimen, e.g., a single monthly or bimonthly administration of 1 and 3 mg/kg of the Ab, achieves greater than 90% receptor occupancy for 2 weeks and at least 4 weeks, respectively. This prolonged KIR blockade significantly potentiates the cytotoxic activity of NK cells, resulting in enhanced NK-cell mediated killing of cancer cells. Preliminary Phase 1 data revealed that 6 AML patients treated with 1-7F9 at dosages of 1 and 3 mg/kg showed a significantly improved OS rates of about an additional 18 months compared to the 16 patients treated with <0.3 mg/kg: 29.7 months compared with 11.8 months, respectively (P=0.034 by log-rank test) (Vey et al., 2012).

A variant of 1-7F9(S241P), in which the serine at position 241 (according to the Kabat numbering system; residue 231 in SEQ ID NO: 4) of the IgG4 H chain has been changed to proline, is described in PCT Publication No. WO 2008/084106. This 1-7F9(S241P) variant has also been variously designated as IPH2102, BMS-986015, and the United States Adopted Names Council (USANC) nonproprietary name, lirilumab. The amino acid sequence of the H chain of lirilumab, which comprises the same V$_H$ and V$_L$ regions as 1-7F9, is shown as SEQ ID NO:4 and the kappa L chain amino acid sequence of lirilumab and 1-7F9 is shown as SEQ ID NO:5. The sequences of the H and L chains of lirilumab are also shown in the lirilumab Statement on Nonproprietary Name Adopted by the USAN Council. Incorporation of the S241P mutation into 1-7F9 may be expected to reduce the formation of IgG4 "half-antibodies," comprising a single H chain/L chain pair, notwithstanding that biophysical studies of 1-7F9 did not reveal half-molecule formation (WO 2006/003179). IgG4 half-Ab by-products are thought to form due to heterogeneity of inter-heavy chain disulphide bridges in the hinge region in a proportion of secreted human IgG4 (see Angal et al., 1993).

More significantly, it has been demonstrated that the S241P mutation in lirilumab equalizes the affinity for KIR2DL1 and KIR2DL2/3. 1-7F9 hinds to each of KIR2DL1 and KIR2DL2/3 with a dissociation constant of 0.43 nM and 0.025 nM, respectively. Consequently, a higher dose of 1-7F9 may need to be administered to KIR2DL$^+$ patients, compared to KIR2DL2/3$^+$ patients, in order to achieve adequate receptor saturation. The S241P mutation in lirilumab has the unexpected superior effect of improving KIR2DL1 receptor binding. KIR receptor occupancy was measured on cells from KIR2DL2/3$^+$ and KIR2DL1$^+$ patients treated with 1-7F9 at concentrations of 0.2. or 2 mg/kg, or with lirilumab at 1 mg/kg. It was found that lirilumab at 1 mg/kg achieved full receptor occupancy (effectively 100%) over a 28-day period for both KIR2DL1$^+$ and KIR2DL2/3$^+$ patients. In contrast, although 1-7F9 provides good receptor occupancy throughout the 28-day period at both doses tested (0.2 mg/kg and 2 mg/kg) in KIR2DL2/3+ patients, receptor occupancy in KIR2DL1+ patients dropped significantly to about 45% and about 85% when the Ab was administered at 0.22 mg/kg and 2 mg/kg, respectively. Thus, a low dose of lirilumab achieves KIR receptor saturation in both KIR2DL1+ and KIR2DL2/3+ patients, such that a single dosage regimen, typically comprising a lower dosage and/or lower frequency of dosing compared to 1-7F9, is needed to treat patients by a KIR blockade-mediated mechanism.

The specificity and affinity with which lirilumab binds to KIR targets is the same as that exhibited by 1-7F9 since the two Abs have identical CDRs and variable regions.

Cross-Competing Anti-KIR mAbs

The ability of a pair of Abs to "cross-compete" for binding to an antigen indicates that a first Ab binds to substantially the same epitope region of the antigen as, and reduces the binding of, a second Ab to that particular epitope region and, conversely, the second Ab binds to substantially the same epitope region of the antigen as, and reduces the binding of, the first Ab to that epitope region. Thus, the ability of a test Ab to competitively inhibit the binding of, for example, lirilumab or DF200 to KIR2DL1 and/or KIR2DL2/3 demonstrates that the test Ab binds to substantially the same epitope region of KIR2DL1 and/or KIR2DL2/3 as lirilumab or DF200, respectively.

A first Ab is considered to bind to "substantially the same epitope" or "substantially the same determinant" as a second Ab if the first Ab reduces the binding of the second Ab to an antigen by at least about 20%, at least about 40%, at least about 50%, or at least about 70%. Preferably, the first Ab reduces the binding of the second Ab to the antigen by more than about 50% (e.g., at least about 60% or at least about 70%). In more preferred embodiments, the first Ab reduces the binding of the second Ab to the antigen by more than about 70% (e.g., at least about 80%, at least about 90%, or about 100%). The order of the first and second Abs can be reversed, i.e. the "second" Ab can be first bound to the surface and the "first" is thereafter brought into contact with the surface in the presence of the "second" Ab. The Abs are considered to "cross-compete" if a competitive reduction in binding to the antigen is observed irrespective of the order in which the Abs are added to the immobilized antigen.

Cross-competing Abs are expected to have similar functional properties by virtue of their binding to substantially the same epitope region of an antigen such as a KIR receptor. The higher the degree of cross-competition, the more similar will the functional properties be. This similarity in function is expected to be even closer if the cross-competing Abs exhibit similar affinities for binding to the epitope as measured by the dissociation constant ($K_D$).

Cross-competing anti-KIR Abs can be readily identified based on their ability to detectably compete in standard antigen binding assays, including surface plasmon resonance (BIAcore®) analysis, ELISA assays or flow cytometry, using either recombinant KIR molecules or cell-surface expressed KIR molecules. For example, a simple competition assay may involve: (1) measuring the binding of a first anti-KIR Ab (e.g., DF200 or NKVSF1), applied at saturating concentration, to a BIAcore chip (or other suitable medium for surface plasmon resonance analysis) onto which KIR2DL1 is immobilized, and (2) measuring the binding of the first Ab to a KIR2DL1-coated BIAcore chip (or other medium suitable) in the presence of a second Ab (e.g., lirilumab or 1-4F1). The binding of the first Ab to the KIR2DL1-coated surface in the presence and absence of the second Ab is compared. A significant (e.g., more than about 20%) reduction in binding of the first Ab in the presence of the second Ab indicates that both Abs recognize substantially the same epitope such that they compete for binding to the KIR2DL1 target. The percentage by which the binding of a first Ab to an antigen is inhibited by a second Ab can be calculated as: [1-(detected binding of first Ab in presence of second Ab)/(detected binding of first Ab in absence of second Ab)]×100. Examples of competitive binding assays are provided in, e.g., WO 2006/003179.

Unless otherwise specified, an Ab that cross-competes with, for example, lirilumab, 1-7F9 or 1-4F1 may cross-compete with these Abs for binding to human KIR2DL1, human KIR2DL2/3, or both human KIR2DL1 and KIR2DL2/3. Epitope maps have been constructed from cross-competition binding experiments obtained by BIAcore analysis with various anti-KIR Abs binding to KIR2DL and KIR2DS polypeptides (see, e.g., WO 2006/003179). For example, 1-7F9 is competitive with EB6 and 1-4F1, but not with NKVSF1 and DF200, for binding to KIR2DL1. MAb 1-4F1 in turn is competitive with EB6, DF200, NKVSF1 and 1-7F9 for binding to KIR2DL1. NKVSF1 competes with DF200, 1-4F1, and EB6, but not 1-7F9, on KIR2DL1. DF200 competes with NKVSF1, 1-4F1, and EB6, but not 1-7F9, on KIR2DL1. Regarding competitive binding to KIR2DL3, 1-7F9 competes with DF200, GL183 and 1-4F1, but not with NKVSF1. 1-4F1 competes with NKVSF1, DF200, GL183, and 1-7F9. NKVSF1 competes with DF200, 1-4F1, and GL183, but not 1-7F9, and DF200 competes with NKVSF1, 1-4F1, and 1-7F9, but not with GL183, for binding to KIR2DL3.

Anti-KIR mAbs for Use in the Disclosed Methods or Kits

This disclosure provides NK cell-mediated methods for treating pediatric BCP-ALL patients, including adoptive NK cell transfer of ex vivo activated mature donor-specific NK cells, "bridging" therapy with low dose 5-Aza-cytidine, and treatment comprising administering to the patient an anti-KIR Ab or an antigen-binding portion thereof that binds specifically to an inhibitory KIR and blocks inhibitory KIR activity, thereby potentiating NK cell lytic activity. An anti-KIR mAb suitable for use in these therapeutic methods, as well as the therapeutic kits disclosed herein, exhibits one or more, preferably at least two, and more preferably all, of the following characteristics: (a) binds specifically to human KIR2DL1 and/or KIR2DL2/3 with a $K_D$ of $1\times10^{-8}$ M or lower, as determined by surface plasmon resonance using a BIAcore biosensor system; (b) inhibits the binding of KIR2DL1 and/or KIR2DL2/3 on the surface of NK cells to their cognate HLA-C ligands on target cells; (c) blocks inhibitory KIR signaling from KIR2DL1 and/or KIR2DL2/3; (d) potentiates NK cell lytic activity; and (e) inhibits tumor cell growth in vivo. Abs that exhibit these properties are exemplified in, among others, PCT Publication Nos. WO 2006/003179 and WO 2008/084106, the entire disclosures of which are incorporated by reference herein.

Abs typically bind specifically to their cognate antigen with high affinity, reflected by a $K_D$ of $10^{-5}$ to $10^{-11}$ $M^{-1}$ or lower. Any $K_D$ greater than about $10^{-4}$ $M^{-1}$ is generally considered to indicate nonspecific binding. As used herein, an Ab that "binds specifically" to an antigen refers to an Ab that binds to the antigen with high affinity, which means having a $K_D$ of about $10^{-7}$ M or lower, preferably about $10^{-8}$ M or lower, more preferably about $5\times10^{-9}$ M or lower, even more preferably about $10^{-9}$ M or lower, still more preferably about $5\times10^{-10}$ M or lower, and most preferably between about $10^{-9}$ M and about $10^{-11}$ M or lower, but does not bind with high affinity to different antigens except where an Ab may be cross-reactive with a common epitope in different antigens.

By way of example, as disclosed in WO 2006/003179, DF200 binds to KIR2DL1 with a $K_D$ of about $1.1 \times 10^{-8}$ M, and to KIR2DL3 with a $K_D$ of about $2 \times 10^{-9}$ M, whereas 1-7F9 binds to KIR2DL1 with a $K_D$ of about $4.3 \times 10^{-10}$ M, and to KIR2DL3 with a $K_D$ of about $2.5 \times 10^{-11}$ M. Accordingly, in certain embodiments of the disclosed methods, the anti-KIR Ab or antigen-binding portion thereof binds to human KIR2DL1 with a $K_D$ of about of $2 \times 10^{-8}$ M, preferably about $10^{-8}$ M or lower, more preferably about $5 \times 10^{-9}$ M or lower, about $10^{-9}$ M or lower, about $4.5 \times 10^{-10}$ M or lower, or between about $10^{-8}$ M to about $10^{-10}$ M or lower. In other embodiments, the anti-KIR Ab or antigen-binding portion thereof binds to human KIR2DL2/3 with a $K_D$ of about of $10^{-8}$ M, preferably about $5 \times 10^{-9}$ M or lower, more preferably about $2 \times 10^{-9}$ M or lower, about $10^{-10}$ M or lower, about $2.5 \times 10^{-11}$ M or lower, or between about $10^{-9}$ M to about $10^{-11}$ M or lower. In certain embodiments, the anti-KIR Ab or antigen-binding portion thereof binds to human KIR2DL1 and/or KIR2DL2/3 with a $K_D$ of about of $10^{-8}$ to $10^{-9}$ M. In other embodiments, the anti-KIR Ab or antigen-binding portion thereof binds to human KIR2DL1 and/or KIR2DL2/3 with a $K_D$ of about of $10^{-9}$ to $10^{-11}$ M. In preferred embodiments, the Abs or antigen-binding portions thereof are cross-reactive with both KIR2DL1 and KIR2DL2/3. In other embodiments, these cross-reactive Abs bind to KIR2DL antigens with about the same $K_D$ values as does DF200, lirilumab or 1-4F1, or lower $K_D$ values.

In certain embodiments, the anti-KIR Ab or antigen-binding portion thereof binds specifically to, and blocks the inhibitory activity of, KIR2DL1. In other embodiments, the anti-KIR Ab or antigen-binding portion thereof binds specifically to, and blocks the inhibitory activity of, KIR2DL2/3. Blocking the activity of an inhibitor KIR receptor results in potentiation of NK cell cytotoxicity. Since at least one of KIR2DL1 or KID2DL2/3 is present in about 90% or more of the human population, Abs preferred for use in the disclosed methods are cross-reactive with both KIR2DL1 or KID2DL2/3, and are capable of potentiating the activity of NK cells expressing either or both of these KIRs. Therefore, compositions comprising such cross-reactive anti-KIR Abs may be used to effectively potentiate the lytic activity of NK cells in most human individuals, typically in at least about 90% of human individuals or more. Accordingly, a single Ab composition may be used to treat most human subjects, obviating in most cases the need to determine KIR- or HLA-allelic group status or to use mixtures or cocktails of two or more anti-KIR mAbs.

A therapeutic anti-KIR that is suitable for use in the disclosed methods and kits should preferably not bind to stimulatory KIR2DS receptors, thus avoiding the reduction in stimulatory potential that would be associated with neutralization of the activating KIR2DS receptors. In certain embodiments, the anti-KIR Ab or antigen-binding portion thereof does not bind KIR2DS4. In contrast to the murine mAbs NKVSF1 (Pan2D), A210, and A208g, none of 1-7F9, lirilumab and 1-4F1 binds to KIR2DS4, making them better suited for therapeutic purposes. Similar to the murine NKVSF1 and DF200 mAbs, the human Abs, 1-7F9, lirilumab and 1-4F1, also bind to KIR2DS1 and KIR2DS2, but KIR2DS1 and KIR2DS2 are not believed to be important in anti-leukemia efficacy. Thus, Abs preferred for use in the disclosed methods bind to a common determinant present on at least two different KIR2DL gene products, but not on KIR2DS4, and cause potentiation of NK cells expressing at least one of those KIR2DL receptors. In certain embodiments, the anti-KIR Ab or antigen-binding portion thereof binds to both KIR2DL1 and KIR2DL2/3, but not to KIR2DS4. In further embodiments, the anti-KIR Ab or antigen-binding portion thereof also does not bind to KIR2DS3, i.e., the Ab binds to both KIR2DL1 and KIR2DL2/3, but not to KIR2DS3 or to KIR2DS4. In preferred embodiments, the anti-KIR Ab binds specifically to substantially the same epitope recognized by lirilumab or the human mAb, 1-4F1, which epitopes are present on KIR2DL1, -2 and -3, but not on KIR2DS4 or KIR2DS3.

In certain embodiments of the disclosed methods and kits, the anti-KIR Ab or antigen-binding portion thereof cross-competes for binding to at least one of KIR2DL1 and KIR2DL2/3 with a reference Ab or antigen-binding portion thereof which comprises a human $V_H$ region comprising consecutively linked amino acids having the sequence set forth in SEQ ID NO:1 and a human $V_L$ region comprising consecutively linked amino acids having the sequence set forth in SEQ ID NO:2. In other embodiments, the anti-KIR Ab or antigen-binding portion thereof cross-competes with a reference Ab or antigen-binding portion thereof for binding to each of KIR2DL1 and KIR2DL2/3, wherein the reference Ab comprises a human $V_H$ region comprising consecutively linked amino acids having the sequence set forth in SEQ ID NO:1 and a human $V_L$ region comprising consecutively linked amino acids having the sequence set forth in SEQ ID NO:2. In certain preferred embodiments of these methods, the reference Ab or antigen-binding portion thereof is lirilumab, the H chain sequence of which is set forth in SEQ ID NO:4 and the L chain sequence of which is set forth in SEQ ID NO:5, or an antigen-binding portion thereof.

Murine anti-KIR Abs are unsuitable for therapeutic use in human patients because they could provoke a HAMA response, thus compromising the efficacy of the treatment. This problem can be obviated by using chimeric, humanized or human Abs or antigen-binding portions thereof. Methods for the preparation and isolation of chimeric, humanized or human Abs are well known in the art. Accordingly, in certain embodiments, the anti-KIR Ab used in any of the disclosed methods is a chimeric Ab or a humanized Ab, or an antigen-binding portion thereof. In preferred embodiments, the anti-KIR Ab is a human Ab or an antigen-binding portion thereof. The anti-KIR Abs used in any of the disclosed methods are also preferably monoclonal Abs.

The Abs can be of any isotype, including IgG1, IgG2, IgG3, or IgG4. In particular embodiments, the Ab is a human IgG1 Ab. In other embodiments, the Ab is a human IgG4 Ab, preferably modified to contain the hinge-stabilizing S241P mutation (see WO 2008/084106).

In certain embodiments of the disclosed methods and kits, the anti-KIR Ab or antigen-binding portion thereof comprises the CDR1, CDR2 and CDR3 domains in a $V_H$ region comprising consecutively linked amino acids having the sequence set forth in SEQ ID NO:1, and/or the CDR1, CDR2 and CDR3 domains in a $V_L$ region comprising consecutively linked amino acids having the sequence set forth in SEQ ID NO:2.

In other embodiments, the anti-KIR Ab or antigen-binding portion thereof comprises a H chain CDR1 domain comprising consecutively linked amino acids having the sequence set forth in SEQ ID NO:6, a H chain CDR2 domain comprising consecutively linked amino acids having the sequence set forth in SEQ ID NO:7, a H chain CDR3 domain comprising consecutively linked amino acids having the sequence set forth in SEQ ID NO:8, a L chain CDR1 domain comprising consecutively linked amino acids having the sequence set forth in SEQ ID NO:9, a L chain CDR2 domain comprising consecutively linked amino acids having the sequence set forth in SEQ ID NO:10, and a L chain CDR3 domain comprising consecutively linked amino acids having the sequence set forth in SEQ ID NO:11.

In certain preferred embodiments, the anti-KIR Ab or antigen-binding portion thereof comprises a human $V_H$ region comprising consecutively linked amino acids having the sequence set forth in SEQ ID NO:1 and a human $V_L$ region comprising consecutively linked amino acids having the sequence set forth in SEQ ID NO:2. In other preferred embodiments, the anti-KIR Ab or antigen-binding portion thereof comprises a human H chain comprising consecutively linked amino acids having the sequence set forth in SEQ ID NO:3 or SEQ ID NO:4 and a human $V_L$ region comprising consecutively linked amino acids having the sequence set forth in SEQ ID NO:2. In yet other preferred embodiments, the anti-KIR Ab or antigen-binding portion thereof is lirilumab, the H and L chain sequences of which are set forth in SEQ ID NOs. 4 and 5, respectively, or an antigen-binding portion thereof. In other embodiments, the anti-KIR Ab or antigen-binding portion thereof is 1-7F9, 1-4F1, 1-6F5 or 1-6F1, or an antigen-binding portion of any of these Abs. In further embodiments, the anti-KIR Ab or antigen-binding portion thereof comprises a human H chain comprising consecutively linked amino acids having the sequence set forth in SEQ ID NO:4 and a human $V_L$ region comprising consecutively linked amino acids having the sequence set forth in SEQ ID NO:2.

In yet other embodiments, the instant anti-KIR Abs suitable for use in the disclosed methods comprise $V_H$ and $V_L$ regions having amino acid sequences that are highly similar or homologous to the amino acid sequences of the KIR2DL-cross-reactive mAbs exemplified in WO 2006/003179, including 1-7F9 (which comprises the same $V_H$ and $V_L$ regions as lirilumab), 1-4F1, 1-6F5 and 1-6F1, wherein the instant anti-KIR Abs retain the functional properties of the aforementioned exemplified cross-reactive Abs. For example, the instant anti-KIR Abs comprise a $V_H$ and $V_L$ region, each of which comprises consecutively linked amino acids having a sequence that is at least 80% identical to the amino acid sequences of the $V_H$ and/or $V_L$ regions, respectively, of 1-7F9, 1-4F1, 1-6F5 or 1-6F1. In other embodiments, the $V_H$ and/or $V_L$ amino acid sequences may exhibit at least 85%, 90%, 95%, 96%, 97%, 98% or 99% identity to the sequences of the $V_H$ and/or $V_L$ regions, respectively, of 1-7F9, 1-4F1, 1-6F5 or 1-6F1.

As used herein, the percent sequence identity (also referred to as the percent sequence homology) between two amino acid sequences is a function of the number of identical positions shared by the sequences relative to the length of the sequences compared (i.e., % identity=[number of identical positions/total number of positions being compared]×100), taking into account the number of any gaps, and the length of each such gap, introduced to maximize the degree of sequence identity between the two sequences. The comparison of sequences and determination of percent identity between two sequences can be accomplished using mathematical algorithms and sequence analysis software that are well know to those of ordinary skill in the art. Protein analysis software matches similar sequences using measures of similarity assigned to various substitutions, deletions and other modifications, including conservative amino acid substitutions. For instance, the publicly available GCG software contains programs such as GAP and BESTFIT which can be used with default parameters to determine sequence homology or sequence identity between closely related polypeptides. Polypeptide sequences can also be compared using FASTA, applying default or recommended parameters. An algorithm for comparing a sequence to a database containing a large number of sequences from various organisms is the computer program BLAST, especially blastp, using default parameters (see, e.g., Altschul et al., 1990; 1997).

In preferred embodiments, the Ab comprises $V_H$, $V_L$ or both $V_H$ and $V_H$ regions that are substantially identical to the $V_H$ and/or $V_H$ regions of lirilumab, 1-4F1, 1-6F5 or 1-6F1. The term "substantially identical" in the context of two amino acid sequences means that the sequences, when optimally aligned, such as by the programs GAP or BESTFIT using default gap weights, share at least about 70% or at least about 80%, preferably at least about 90% or at least about 95%, more preferably at least about 98% or at least about 99% sequence identity. In certain embodiments, residue positions that are not identical differ by conservative amino acid substitutions.

Abs having very similar amino acid sequences are likely to have essentially the same functional properties, especially where the sequence differences are conservative modifications. As used herein, "conservative sequence modifications" or "conservative modifications" refer to amino acid modifications that do not significantly affect the binding and functional characteristics of the Ab containing the amino acid sequence. Such conservative modifications include amino acid substitutions, additions and deletions. Conservative amino acid substitutions are substitutions in which the amino acid residue is replaced with an amino acid residue having a similar side chain. Thus, for example, one or more amino acid residues within the CDR regions of an Ab can be replaced with other amino acid residues from the same side chain family (e.g., the acidic side chain family consisting of aspartate and glutamate, or the basic side chain family consisting of arginine, lysine and histidine) and the altered Ab can be tested for retained function using functional assays that are well known in the art. Accordingly, in certain embodiments, the anti-KIR Abs used in the disclosed therapeutic methods comprise $V_H$ and/or $V_L$ regions each comprising CDR1, CDR2 and CDR3 domains, wherein one or more of these CDR domains comprise consecutively linked amino acids having sequences that are the same as the CDR sequences of 1-7F9, 1-4F1, 1-6F5 or 1-6F1 or conservative modifications thereof. MAbs comprising CDRs containing such conservative substitutions retain the desired functional properties of the anti-KIR Abs since it is well known that the variable regions and even the CDRs of an Ab can tolerate multiple sequence modifications without affecting the binding characteristics of an Ab (Rudikoff et al., 1982).

Rudikoff et al. make clear that in some situations, involving non-conservative sequence modifications, even a single change in the amino acid sequence of a CDR, e.g., a change from glutamic acid (an amino acid with an acidic, negatively-charged, 5-carbon side chain) to alanine (an amino acid with a small 1-carbon hydrophobic side chain), may dramatically affect antigen-binding function. However, such alteration in antigen binding is the exception, and it was shown that as many as 8 or 9 amino acid substitutions in the CDRs of two different antigen-binding proteins may be tolerated without affecting antigen binding (Rudikoff et al., 1982).

In certain embodiments, the sequence of the $V_H$ or $V_L$ region of an anti-KIR Ab used in the disclosed methods contains no more than 5, 10 or 15 conservative modifications from the amino acid sequence of the $V_H$ or $V_L$ region of lirilumab, 1-4F1, 1-6F5 or 1-6F1. In certain preferred embodiments, the sequence of the $V_H$ or $V_L$ region of the anti-KIR Ab contains no more than 1, 2, 3 or 4 conservative amino acid modifications from the lirilumab, 1-4F1, 1-6F5 or 1-6F1 sequences. Preferably, these conservative modifications are conservative amino acid substitutions.

In certain other embodiments, the sequence of each CDR of a therapeutic anti-KIR Ab used in the disclosed methods contains no more than 1, 2, 3, or 4 conservative modifications from the amino acid sequence of the corresponding CDRs of lirilumab, 1-4F1, 1-6F5 or 1-6F1. In preferred embodiments, the sequence of each CDR of the anti-KIR Ab contains no more than 2 conservative amino acid modifications from the lirilumab, 1-4F1, 1-6F5 or 1-6F1 sequences. In more preferred embodiments, the sequence of each CDR contains no more than 1 conservative amino acid modification. Preferably, these conservative CDR modifications are conservative amino acid substitutions.

Further, it is well known in the art that the $V_H$ CDR3 is the primary determinant of binding specificity and affinity of an Ab, and that multiple Abs can predictably be generated having the same binding characteristics based on a common $V_H$ CDR3 sequence. For example, Beiboer et al. (2000) generated a recombinant human Ab to epithelial glycoprotein-2 (EGP-2) by humanization of a murine mAb, MOC-31, using guided selection. This human anti-EGP2 Ab was produced by sequentially replacing the murine variable $V_H$ and $V_L$ genes of murine MOC-31 Ab with human V gene repertoires, while retaining only the $V_H$ CDR3 domain of the murine MOC-31 Ab. Consistent with the $V_H$ CDR3 being the primary determinant of antigen binding, the newly created Ab was found to bind the same epitope and have a similar binding affinity as the parental murine Ab. Another example is Ditzel et al. (1996), which describes grafting studies showing that transfer of a H chain CDR3 of a first Ab to the H chain of a second Ab permits retention of the binding specificity of the first Ab. Specifically, the H chain CDR3 sequence of the polyspecific Fab LNA3 was grafted onto the H chain of the monospecific IgG tetanus toxoid-binding Fab p313, thereby replacing the existing heavy chain CDR3. The binding specificity of the LNA3 H chain CDR3-grafted Fab (LNA3/p313) was shown by ELISA to be the same as the original LNA3 Fab. Many other publications demonstrate that the binding specificity and affinity of an Ab can be defined by specifying the sequence of the H chain CDR3 domain and, in general, once the H chain CDR3 sequence Ab is defined, variability in the other five CDR sequences does not greatly affect the binding specificity of that Ab. Accordingly, in certain embodiments, anti-KIR Abs or antigen-binding portions thereof for use in the disclosed methods comprise 6 CDRs, the sequence of the $V_H$ CDR3 being the same as the sequence of the $V_H$ CDR3 of lirilumab, 1-4F1, 1-6F5 or 1-6F1, and the sequences of 1, 2, 3 4, or all 5 of the other CDRs containing conservative sequence modifications.

Anti-KIR Abs usable in the disclosed therapeutic methods and kits also include antigen-binding portions of these Abs. It has been amply demonstrated that the antigen-binding function of an Ab can be performed by fragments of a full-length Ab. Examples of binding fragments encompassed within the term "antigen-binding portion" of an Ab include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an Ab. Additional antigen-binding portions of Abs include scFv, di-scFv or bi-scFv, and scFv-Fc fragments, diabodies, triabodies, tetrabodies, and isolated CDRs (see Hollinger and Hudson, 2005; Olafsen and Wu, 2010, for further details).

Pharmaceutical Compositions and Dosages

Therapeutic agents for use in the disclosed methods and kits may be constituted in a composition, e.g., a pharmaceutical composition containing an anti-KIR Ab and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier for a composition containing an anti-KIR Ab is suitable for intravenous, intramuscular, subcutaneous, parenteral, spinal or epidermal administration (e.g., by injection or infusion). A pharmaceutical composition of the invention may include one or more pharmaceutically acceptable salts, anti-oxidant, aqueous and non-aqueous carriers, and/or adjuvants such as preservatives, wetting agents, emulsifying agents and dispersing agents.

Dosage regimens are adjusted to provide the optimum desired response, e.g., a maximal therapeutic response and/or minimal adverse effects. For administration of an anti-KIR Ab, the dosage may range from about 0.001 to about 20 mg/kg, preferably from about 0.01 to about 10 mg/kg, more preferably from about 0.1 to about 3 mg/kg, of the subject's body weight. For example, dosages can be 0.01, 0.05, 0.1, 0.3, 0.5, 1, 2, 3, 5 or 10 mg/kg body weight, and more preferably, 0.1, 0.3, 1, 2, 3, or 5 mg/kg body weight. The dosing schedule is typically designed to achieve exposures that result in sustained receptor occupancy (RO) based on typical pharmacokinetic properties of an Ab. Considering that an IgG4 Ab typically has a half-life of 2-3 weeks, a typical dosage regimen for an IgG Ab comprises 0.1-10 mg/kg body weight via intravenous administration once every 14-21 days in up to 6-week or 12-week cycles until complete response or confirmed progressive disease. For 1-7F9 specifically, it has been shown that low dosages achieve full (>90%) KIR receptor occupancy for prolonged periods (Vey et al., 2012). For example, a dosage of 0.075 mg/kg resulted in full occupancy for 1 week, 1 mg/kg resulted in full occupancy for 2 weeks, and 3 mg/kg resulted in full occupancy for at least 4 weeks. At 3 mg/kg, KIR saturation (>30% KIR occupancy) persisted for 24-32 weeks (Vey et al., 2012).

Accordingly, in certain embodiments of the therapeutic methods comprising administration of an anti-KIR Ab, the Ab or antigen-binding portion thereof is administered at a dose ranging from 0.001 to 20 mg/kg body weight once every 2, 3 or 4 weeks. In other embodiments, the anti-KIR Ab or antigen-binding portion thereof is administered less frequently at a dose ranging from 0.001 to 20 mg/kg body weight, preferably 0.1, 0.3, 1, 2, 3, or 5 mg/kg body weight, more preferably 1 or 3 mg/kg body weight, once every month to once every two months. Considering the ability of the S241P mutation in lirilumab to equalize the affinity for KIR2DL1 and KIR2DL2/3, an even lower dosage regimen may suffice for treatment with lirilumab. For example, in certain embodiments of the present methods comprising administration of lirilumab or similar mAb containing a S241P mutation, the anti-KIR Ab or antigen-binding portion thereof is administered to the patient at a dose of 0.01, 0.05, 0.1, 0.3, 0.5, 1 or 2 mg/kg body weight about once every 2 or 3 weeks, or about once a month to once every two months.

NK Cell-Mediated Immunotherapeutic Methods

The difference in the susceptibility of adult and childhood BCP-ALL to NK cell-mediated lysis has been mainly ascribed to differing expression of cell adhesion molecules of the β1 and β2 integrin and the Ig superfamily, respectively, that essentially results in reduced NK cell-target conjugate formation and activation in the case of adult BCP-ALL (Pende et al., 2009; Mengarelli et al., 2001). In addition, the surface density of HLA class I ligands is greater, and the expression of ligands to major activating NK cell receptors such as NKG2D is lower, in pediatric BCP-ALL as compared to AML (Pende et al., 2005). Consistent with these expression patterns, it has been demonstrated that the in vitro catalytic activity of NK cells against BCP-ALL in part correlated with the extent of MHC expression on the respective specimens (Feuchtinger et al., 2009; Pfeiffer et al., 2007).

Given the disparity in the availability of effective treatments for adult and pediatric acute lymphoid leukemia, NK cell-based immune responses to pediatric BCP-ALL have been investigated herein. The disclosed data reveal that not only mature KIR$^+$, but interestingly also immature KIR$^-$ NK cells, control pediatric BCP-ALL in vivo. These data strongly suggest that NK cell-mediated immune-responses may be exploited for treating poor-prognosis pediatric BCP-ALL patients.

Treatment of Pediatric BCP-ALL with an Anti-Inhibitory KIR Ab

Following previous work that demonstrated that the injection of patient-specific leukemia into NSG mice results in the constitution of a model that reflects individual leukemogenecity (Woiterski et al., 2013), analysis disclosed herein of the leukemic burden in BCP-ALL-bearing mice upon adoptive NK cell transfer demonstrates that KIR-KIRL-mismatched NK cells targeted but did not eliminate pediatric BCP-ALL (Example 1). Mechanistically, the interaction of NK cells with BCP-ALL was accompanied by a heightened functionality of educated, alloreactive KIR$^+$ NK cells of KIR-KIRL-mismatched donors, particularly in terms of their ability for degranulation (Example 2).

Further, it was shown herein that the inhibitory KIR-blocking mAb, lirilumab, distinctly enhanced the cytotoxicity of matched but not mismatched KIR$^+$ NK cells (Example 2), leading to the conclusion that the KIR-KIRL axis indeed controls NK cell alloreactivity. Lirilumab has also been shown herein to reduce expression of inhibitory KIRs to very low levels in huNSG mice (Example 7). The effects of lirilumab on tumor burden in huNSG mice (Example 7) and adoptive transfer of NK cells into huNSG mice (Example 8) are under investigation. Thus far, the available data from in vitro experiments and mouse in vivo models provide compelling evidence to suggest that an anti-inhibitory KIR Ab, preferably an Ab that blocks both KIR2DL1 and KIR2DL2/3 activity and potentiates NK cell cytotoxicity, would be clinically effective in treating selected young BCP-ALL patients. A possible explanation for the variable effectiveness of inhibitory KIR blockade is the "licensing" hypothesis which implies that the KIR2DL2/3$^+$ NK cell subset in the selected KIR-KIRL-mismatched, HLA-C2 homozygous donors has remained uneducated whereas the same subset in our KIR-KIRL-matched, HLA-C1 homozygous donors has been subject to education and will therefore exert full functionality upon KIR2DL2/3 blockade (Example 3).

Accordingly, this disclosure provides a method for treating a pediatric subject afflicted with BCP-ALL comprising administering to the subject an anti-KIR Ab or an antigen-binding portion thereof that binds specifically to an inhibitory KIR and blocks inhibitory KIR activity, thereby potentiating NK cell lytic activity. In certain embodiments, the subject is a pediatric patient who lacks a KIR-KIRL-mismatched donor. In other embodiments, the pediatric subject is under about 20 years of age. In further embodiments, the patient is about 1 year old or younger. In certain embodiments, the anti-KIR antibody or antigen-binding portion thereof binds to and blocks the activity of KIR2DL1. In other embodiments, the anti-KIR antibody or antigen-binding portion thereof binds to and blocks the activity of KIR2DL2/3. In certain preferred embodiments, the anti-inhibitory KIR Ab or antigen-binding portion thereof is cross-reactive with, and blocks the activity of, both KIR2DL1 and KIR2DL2/3. In further embodiments, the anti-inhibitory KIR Ab or antigen-binding portion thereof does not bind to the stimulatory receptor, KIR2DS4. In yet other embodiments, the anti-inhibitory KIR Ab or antigen-binding portion thereof does not bind to the stimulatory receptor, KIR2DS3.

In certain embodiments of the present methods and kits, the anti-KIR antibody or antigen-binding portion thereof binds to KIR2DL1 with a dissociation constant ($K_D$) of about $4.5 \times 10^{-10}$ M or lower. In other embodiments, the anti-KIR antibody or antigen-binding portion thereof binds to KIR2DL2/3 with a dissociation constant ($K_D$) of about $2.5 \times 10^{-11}$ M or lower.

In further embodiments, the anti-KIR Ab or antigen-binding portion thereof comprises an H chain constant region which is of a human IgG1, IgG2, IgG3 or IgG4 isotype. In certain preferred embodiments, the anti-KIR Ab or antigen-binding portion thereof is of a human IgG1 or human IgG4 isotype. In certain other embodiments, the sequence of the IgG4 H chain constant region of the anti-KIR Ab or antigen-binding portion thereof contains an S241P mutation which replaces a serine residue in the hinge region with the proline residue normally found at the corresponding position in IgG1 isotype antibodies. In yet other embodiments, the Ab comprises an L chain constant region which is a human kappa or lambda constant region. In preferred embodiments, the anti-KIR Ab or antigen-binding portion thereof is a mAb or an antigen-binding portion thereof. The anti-KIR Ab or antigen-binding portion thereof may be a chimeric, humanized or a human Ab or a fragment thereof. Exemplary HuMAbs for use in this method include lirilumab, 1-7F9, 1-4F1, 1-6F5 and 1-6F1. In certain embodiments, the dosing regimen of the anti-KIR Ab or antigen-binding portion thereof comprises a dose ranging from 0.01 to 20 mg/kg body weight, preferably 0.1 to 3 mg/kg, administered about once every 2, 3 or 4 weeks until a complete response, confirmed progressive disease or unmanageable toxicity occurs. In other embodiments, a low dosage/frequency regimen is used comprising administration of 0.01 to 3 mg/kg body weight about once a month or about once every 2 months. In certain preferred embodiments, the anti-KIR Ab or antigen-binding portion thereof is formulated for intravenous administration.

In certain embodiments, the anti-KIR Ab or antigen-binding portion thereof is administered to the subject in conjunction with adoptive NK cell transfer.

Irrespective of the individual KIR-KIRL constellation, the KIR$^-$ NK cell subset interestingly enough displayed substantial functionality. In line with the previously published observation that the attenuated function of KIR$^-$ NK cells can be overcome by exposure to cytokines (Kim et al., 2005), this observation is attributed to the cytokine-rich expansion protocol.

Role of Adoptive NK Cell Transfer in the Treatment of Pediatric BCP-ALL

The data published to date on adoptive NK cell transfer in children is restricted to feasibility studies performed mostly in AML patients (Rubnitz et al., 2010). It was recently demonstrated that the infusion of IL15-stimulated, CD3$^-$/CD19$^-$-depleted HSC grafts (containing high numbers of NK cells) is safe even in the haplo-identical setting (Pfeiffer et al., 2012). Given that NK cells can persist and expand in HLA-mismatched hosts (Miller et al., 2005) and that the transfer of mature NK cells obviously does not promote graft-versus-host-disease (GvHD) (Pfeiffer et al., 2012; Rubnitz et al., 2010), the data disclosed herein support the concept that the adoptive transfer of KIR$^+$ NK cells of KIR-KIRL-mismatched donors might indeed play a role in the treatment of relapsing BCP-ALL disease as an adjunct to haplo-identical HSCT.

Two clinical studies have so far evaluated the feasibility of KIR-KIRL-mismatched haplo-identical HSCTs in children with BCP-ALL. In the first, it was demonstrated that the graft-versus-leukemia (GvL) effect best correlated with the number of KIR-KIRL mismatches (Leung et al., 2004). The second study was performed with the aim of better defining the specificity and clonal distribution of "alloreactive" NK cells (Pende et al., 2009). Collectively, these two preliminary studies show that the incorporation of theoretical assumptions on KIR-KIRL interactions in haplo-identical HSCTs of children with BCP-ALL is feasible, that such a mode of donor selection does not heighten the risk of GvHD and that the analysis of receptor-ligand constellations may have prognostic implications.

It has been systematically demonstrated herein that emerging KIR$^-$ NK cells in huNSG mice exert a considerable cytotoxicity towards BCP-ALL (Example 4), thus extending earlier data that a substantial number of phenotypically healthy appearing NK cells exist in mouse and man that obviously lack the expression of any inhibitory receptor for "self"-HLA class I (Fernandez et al., 2005; Yawata et al., 2008) but nevertheless display a certain degree of functionality. In line with previously published data that "unlicensed" NK cells may exert a profound immune response in the context of murine cytomegalovirus infection (Orr et al., 2011), the data disclosed herein indicate that the anti-tumor properties of immature KIR$^-$ NK cells are substantial and might just as well have been previously underestimated. As inhibitory KIR expression in huNSG mice was negligible despite the administration of IL15/IL15Rα complex, the NK cell activation that occurred is not at this point ascribed to the lack of KIR-KIRL-mediated inhibition; rather, it appears that receptor-ligand interactions other than the one analyzed herein may have contributed to this phenomenon.

Using a humanized xenotransplantation model to analyze GvL potency after haplo-identical HSCT is undoubtedly technically challenging and has apparently so far not been attempted. The application of minimal residual disease (MRD) analysis based on multi (8-11) parameter flow-cytometry enabled the distinction of immunophenotypic features of one (or two) patient-specific malignantly transformed B cell specimen from early-arising donor-type-like B cell-lineage precursors. This approach has allowed the characterization of GvL effects in a dynamic and largely functional hematopoietic system that incorporates complex effector-target cell interactions in the presence of "human-like" bystander cells and supportive cytokines.

Figure 12:
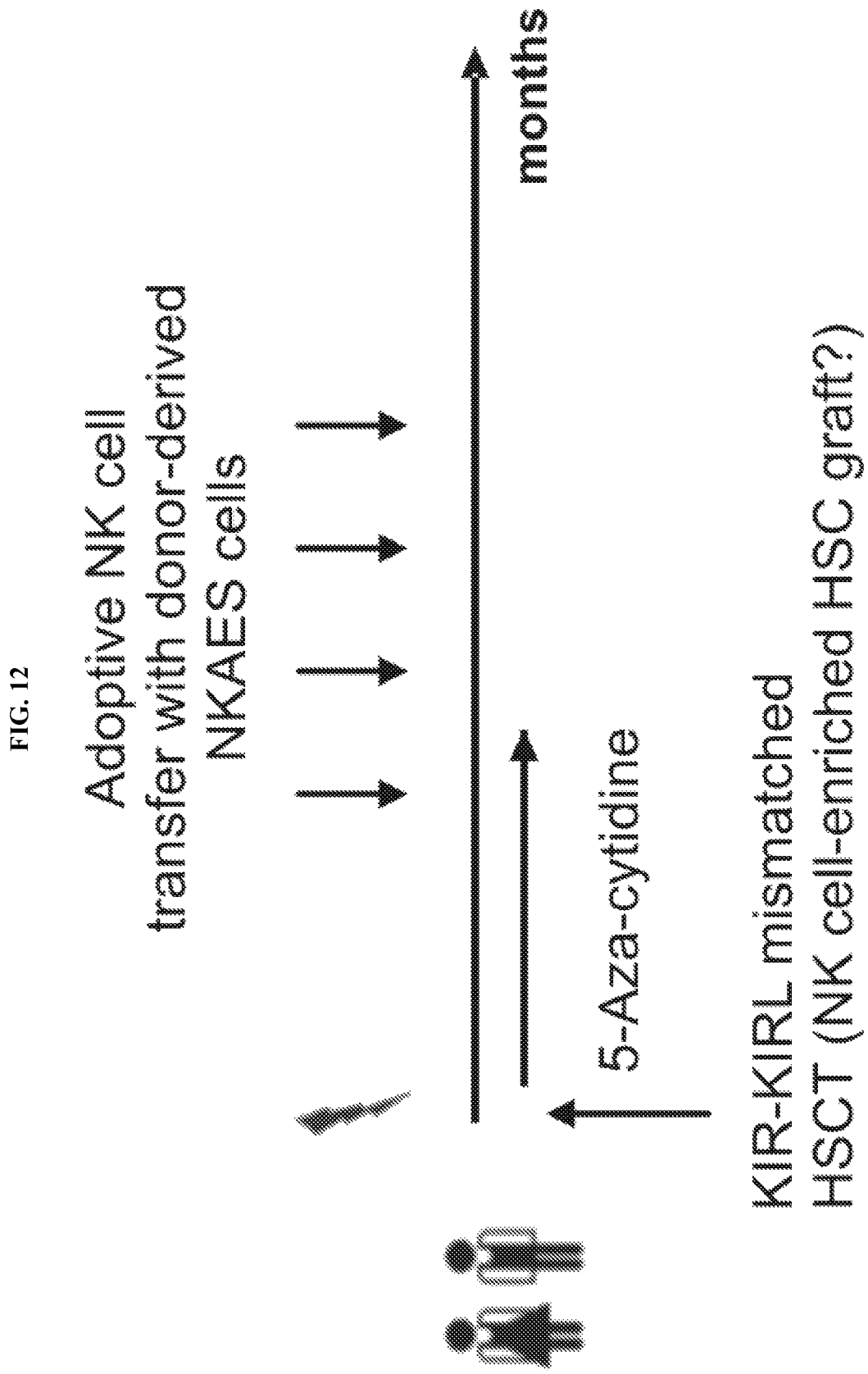
FIG. 12. Chaperoning the NK cell-deficient phase of haplo-identical hematopoietic stem cell transplantation. Delineation of a hypothetical study design in relapsing pediatric BCP-ALL patients ideally exploits NK cell-mediated anti-tumor responses.

The data disclosed herein suggest that not only KIR$^+$, but also immature KIR$^-$, NK cells may exert clinically relevant GvL effects towards pediatric BCP-ALL. Substantial evidence is, thus, provided to support a rationale for adoptive NK cell transfer of ex vivo activated mature donor-specific NK cells that would chaperone the early, NK cell-deficient phase of ideally KIR-KIRL-mismatched haplo-identical HSCTs in children with relapsing BCP-ALL (see FIG. 12).

Role of 5-aza-cytidine Administration in the Treatment of Pediatric BCP-ALL

As recent data indicate that DNA demethylating agents may not only affect the growth of malignant cells but might also modulate inhibitory KIR expression on NK cells, 5-aza-cytidine was tested in a huNSG model. Interestingly, a significantly reduced BCP-ALL burden was observed in huNSG mice that could not be solely attributed to drug-induced, direct cytotoxic effects (Example 5). This observation is in contrast to previously published in vitro data reporting a 5-aza-cytidine-induced functional inhibition of NK cells (Schmiedel et al., 2011; Gao et al., 2009); however, careful analysis of these data reveals that the knowledge of 5-aza-cytidine-mediated, immune modulation of NK cells is basically restricted to studies of mature NK cells of healthy volunteer donors. Analysis of bone marrow (BM)-residing NK cell subsets in huNSG mice demonstrated that 5-aza-cytidine-treated mice harbored distinctly higher numbers of both immature and mature NK cell subsets. It has been speculated that beneficial anti-tumor effects of 5-aza-cytidine should probably be attributed to the induction of HLA class I expression and cancer testis antigens on malignant or pre-malignant cell clones (Lübbert et al., 2010). In line with this tumor-focussed concept, 5-aza-cytidine is used to "bridge" the early post transplantation period in high risk AML and chronic myelomonocytic leukemia (CMML) patients (Jabbour et al., 2009; de Lima et al., 2010). However, based on the results disclosed herein, it is proposed that 5-aza-cytidine therapy might induce a re-modelling in developing NK cell precursors that—presumably together with an altered DC functionality and a fine-tuned NK cell-promoting cytokine milieu (Frikeche et al., 2011) —leads to increased NK cell numbers and improved functionality.

Consistent with the observation that 5-aza-cytidine may promote differentiation of malignantly transformed cells by inducing the re-expression of epigenetically down-regulated PU.1 (Curik et al., 2012), and considering the crucial role that PU.1 plays in the regulation of NK cell differentiation and homeostasis (Colucci et al., 2001), it is believed that the re-expression of PU.1 might have promoted NK cell differentiation in the present model. In addition, it has been shown that low-dose, but not high-dose, 5-aza-cytidine therapy may increase the number of cells in the S phase and may, thus, promote cell cycle progression (Hagemann et al., 2011). In view of data that 5-aza-cytidine therapy does not evoke a broad and unspecific passive demethylation of the genome but, rather, induces a highly specific non-random demethylation pattern (Hagemann et al., 2011), it is proposed that low dose 5-aza-cytidine might have selectively re-shaped factors important for NK cell transcription and cell cycle control. Therefore, the application of a low-dose 5-aza-cytidine "bridging" therapy, potentially under supportive cytokine administration, might additionally promote NK cell differentiation and functionality and would, thus, constitute an optional treatment for those patients lacking a suitable KIR-KIRL-mismatched donor.

Kits

Also within the scope of the present invention are kits comprising an anti-KIR Ab for therapeutic uses. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with pediatric BCP-ALL, the kit comprising: (a) a dosage ranging from 0.001 to 20 mg/kg body weight of an anti-KIR Ab or an antigen-binding portion thereof that specifically binds to an inhibitory KIR receptor, preferably to the human KIR2DL1 and/or KIR2DL2/3 receptor(s), and suppresses inhibitory KIR activity; and (b) instructions for using the anti-KIR Ab in any of the therapeutic methods disclosed herein. In certain embodiments, the anti-inhibitory KIR Ab is co-packaged in unit dosage form. In certain preferred embodiments for treating human patients, the kit comprises an anti-human KIR2DL1- and KIR2DL2/3-cross-reactive Ab, e.g., lirilumab, 1-7F9, 1-4F1, 1-6F5 and 1-6F1.

The present invention is further illustrated by the following examples which should not be construed as further limiting. The contents of all references cited throughout this application are expressly incorporated herein by reference.

EXAMPLE 1

KIR-KIRL Mismatch Constellations Promote the Alloreactivity of Cytokine-Matured NK Cells Towards Pediatric BCP-ALL In Vitro and In Vivo Materials and Methods Mice NOD.Cg-Prkdc$^{scid}$ IL2rg$^{tmWjl}$/Sz (NSG) mice were purchased at The Jackson Laboratory (Bar Harbor, Me.) and maintained under specified pathogen-free conditions in the research animal facility of the University of Tuebingen, Germany. All experimental animal procedures were conducted according to German federal and state regulations.

Induction of Leukemia in NSG Mice

Patient-specific leukemia was induced in NSG mice as described before (Woiterski et al., 2013). The study was approved by the local ethics committee and written informed consent was obtained from the parents of the pediatric patients. Upon engraftment, mice were sacrificed and bone marrow (BM) or spleen specimens of leukemia-bearing mice were stored at −80° C. for de novo generation of patient-specific leukemia at later time points.

NK Cell Activation and Expansion System (NKAES)

Peripheral blood mononuclear cells (PBMCs) from HLA-typed donors (sequence-based typing with 4-digit resolution) (Table 1) were used with informed consent to expand NK cells in a medium containing 100 IU/ml IL2 (Novartis, Switzerland) using irradiated, membrane bound (mb) IL15-41BBL-expressing K562 cells generously provided by D. Campana (University Children's Hospital, Singapore) at a ratio of 1:1.5 (Fujisaki et al., 2009). To expand NK cells in a GMP-guided fashion, pooled human fresh frozen plasma instead of FCS was used. Expanded cells were harvested after 14 days and frozen in the presence of 10% DMSO at −80° C. Prior to experiments, NKAES cells were thawed and cultured overnight in the presence of 100 IU/ml IL2 for in vitro cytotoxicity assays or adoptive transfer experiments and 200 IU/ml IL2 for functional NK cell response staining or alloreactive NK cell subset analysis.

Adoptive NK Cell Transfer

Donor-patient-pairs were selected that provided a mismatch or match in their KIR-KIRL repertoire (Tables 1-3). $1\times10^6$ blasts were intravenously injected into unirradiated NSG mice on Day 0, followed by intravenous injection of $10\times10^6$ NKAES cells at the indicated time points. To monitor engraftment of leukemia, PBMCs of NSG mice were subjected to flow-cytometric analysis using formerly defined patient-specific leukemia surface markers.

Humanization of NSG Mice

Humanization of NSG mice was performed as described (André et al., 2010). Following approval by the local ethics committee, parents donated <5% of the hematopoietic stem cells (HSCs) for humanization of NSG mice. HLA-typed HSCs were purchased from Key Biologics (Memphis, Tenn.). To induce maturation of NK cells, huNSG mice were treated at 12 weeks post-transplantation with a complex of IL15/IL15Rα (Huntington et al., 2009). In addition, huNSG mice were injected once on Day 15 post-initiation of IL15 stimulation by intraperitoneal administration of 100 µpoly I:C (Sigma Aldrich, Taufkirchen, Germany) (Strowig et al., 2010).

Flow-Cytometric Analyses

Antibodies and their corresponding isotype controls were purchased from BD Pharmingen (Germany), Biolegend (Germany), Beckman Coulter (Germany), DAKO (Denmark), ExBio Praha (Czech Republic), R&D (Germany), Miltenyi Biotec (Germany) and One Lambda (Canoga Park, Calif.). In any flow-cytometric analysis, live, vital cells were selected and doublets excluded based on scatter characteristics and low (auto-)fluorescence intensities after incubation with 39.4 µM amine-reactive dye (ARD-)Ax350 (Invitrogen, Germany). The monoclonal anti-MICA, anti-MICB and anti-ULBP1-3 antibodies were generated as described before (Welte et al., 2003) and kindly provided by Alexander Steinle, Frankfurt, Germany.

KIR-Typing

DNA was isolated using the QIAamp DNA Blood Mini Kit (Qiagen), and RNA using the RNeasy Mini Kit (Qiagen), according to the manufacturer's instructions. 0.5 µg of total RNA was transcribed using the Quantitect Reverse Transcription Kit (Qiagen) including a 10-min genomic DNA (gDNA) wipe-out step and reverse transcription for 30 min. The presence of DNA and mRNA, respectively, for selected inhibitory and activating KIRs was investigated as previously described (Alves et al., 2009; Vilches et al., 2007). In brief, KIR-typing was performed in 10 µl reactions using the 2×SYBR Green master mix from Peqlab (KAPA SYBR FAST) and a concentration of 0.25 µM of each primer. The PCR protocol consisted of a first denaturation cycle of 20 s at 95° C., followed by 40 alternating cycles of 95° C. for 3 s and 64° C. for 20 s each. Melting curves from 76° C. to 90° C. were assessed to check for product specificity and presence of the KIRs or positive controls, respectively. H$_2$O was used as negative control and Necdin and GalC were used as internal controls. To exclude erroneous detection of genomic DNA, a reverse transcriptase minus (RT$^-$) control was included that contained all components for reverse transcription with the exception of total RNA. The B content score and the haplotype group assignment were assessed as previously described (Cooley et al., 2010).

Determination of in Vitro Cytotoxicity

Target cells or cell lines were labeled with 0.5 µM CFSE (Vybrant CFDA SE Cell Tracer Kit®, Invitrogen, Germany) 1 day prior to use. NKAES cells were thawed, cultivated overnight and subsequently sorted into KIR$^+$ and KIR$^-$ subsets following labeling with anti-CD158a (clone HP3E4 recognizing KIR2DL1/S1/S4), anti-CD158b (clone GL183 recognizing KIR2DL2/S2/L3) and anti-CD158e (clone DX9 recognizing 3DL1). KIR$^+$ and KIR$^-$ NK cells were used as effector cells and cultured overnight in the presence of 100 IU/ml IL2. Co-incubation with NALM-16 cells was performed in triplicates at ratios between 10:1 and 2:1 for 5 h. Following staining with ARD-Ax350, cells were washed and analyzed. To correct for spontaneously occurring cell death, target cell monoculture controls were included in every experiment. The percentage of specific cytotoxicity was calculated as follows: (% CFSE$^+$ARD$^+$ dead targets–% CFSE$^+$ARD$^+$ spontaneously dead targets)/(100–% CFSE$^+$ ARD$^+$ spontaneously dead targets)×100%.

Determination of In Vivo Cytotoxicity

Figure 9A:
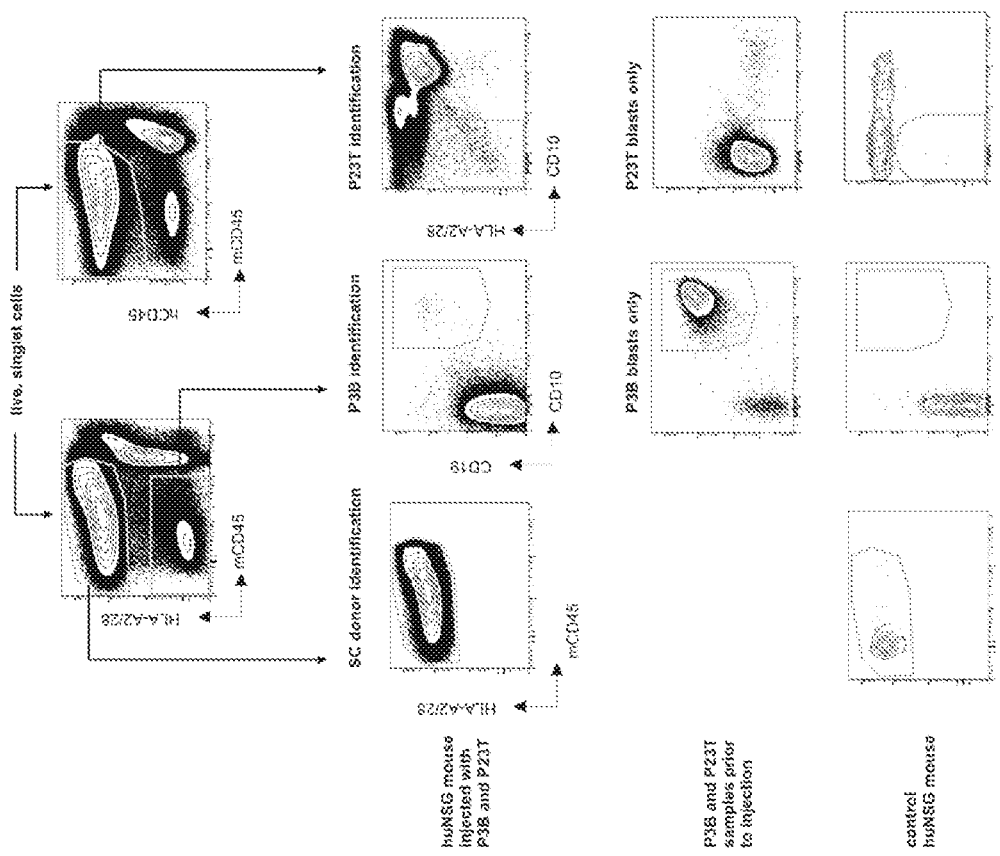
FIG. 9. Adapting the flow-cytometric detection of MRD to a humanized mouse model. A: Polychromatic flow-cytometry of huNSG mice injected with the two BCP-ALL samples P3B and P23T. The hierarchical gating strategy exemplifies the necessity of a pre-defined gating approach to exclude non-malignant human and murine background. Contour plots of mCD45$^-$HLA-A2/28$^+$ cells identify the human hematopoietic stem cell (HSC) donor, mCD45$^-$HLA-A2/28$^-$CD10$^+$CD19$^+$CD38$^+$ cells identify P3B and mCD45$^-$ hCD45$^+$HLA-A2/28$^{dim}$CD10$^-$CD19+ identify P23T. Leukemic cells were derived from NSG mice; thus, samples include non-hematopoetic murine cells like the CD10$^-$CD19$^-$ population in the P3B blast plot. B: The alloreactivity towards P3B but not P23T which is demonstrated in FIG. 8E is not a result of a "P3B-intrinsic" slower growth rate. An analogy to the experiment depicted in FIG. 8E, a pooled sample of equal numbers of P3B and P23T was injected into NSG mice humanized with donor SSC22J (HLA-A 03, HLA-B18/35, HLA-C 12/04) and the extent of leukemic burden was analyzed at 20 h post-injection. As the extent of KIR expression was virtually absent on huNSG-derived NK cells (data not shown), KIR-KIRL interactions in this experiment have probably been insignificant. The number of BM-residing vital blasts normalized to vital murine CD45$^+$ is given. Data are representative of one experiment with a total of 3 huNSG mice per group.

Individual donor-patient-pairs were selected that provided a mismatch or a match with respect to their KIR-KIRL repertoire. Mice were transplanted with HSCs of the respective donor and activated as described above at 12-20 weeks post-transplantation. To study NK cell-mediated cytotoxicity, 3×10$^6$ blasts were intravenously injected into huNSG and the extent of blasts was determined at 20 h post-injection in the BM using polychromatic (8-11) color flow-cytometry. In some experiments, a mixture of 3×10$^6$ NSG-derived blasts (total 6×10$^6$ blasts) of two patients with varying KIR-KIRL repertoires were injected into huNSG mice and leukemia was quantified using the hierarchical gating strategy depicted in FIG. 9A. In all experiments, the frequencies of patient-specific vital blasts were normalized to vital murine CD45$^+$ cells.

Statistics

Mean values and standard error of the mean (SEM) from experiments with 2 conditions were analyzed with the Student t test. The effect size Θ was calculated using the standardized mean difference between two populations: Θ=(μ1−μ2)/σ, where μ1 and μ2 represent the mean values of the two study groups and σ represents the SEM of the total study population.

Results

Figure 1B:
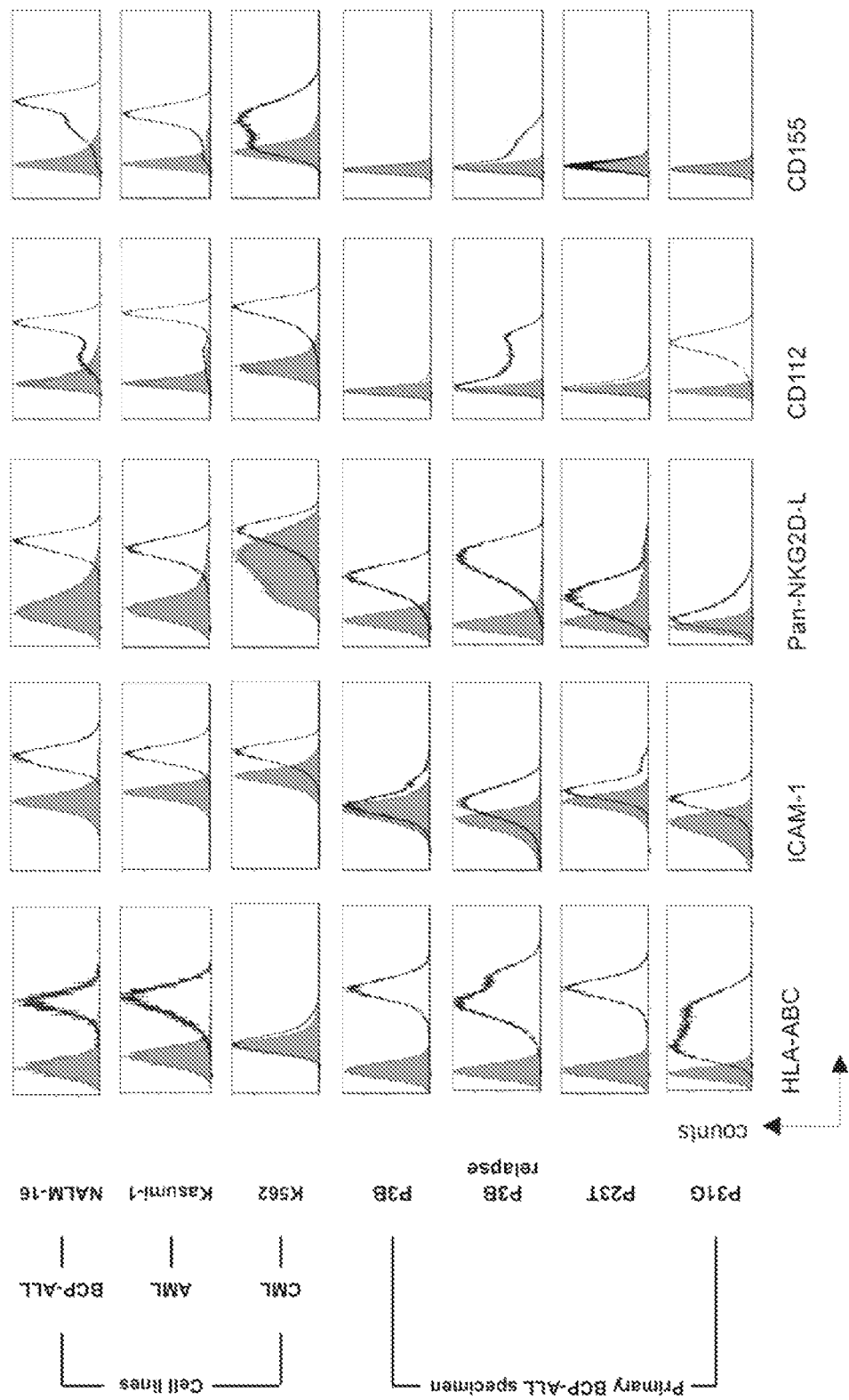
Figure 2B:
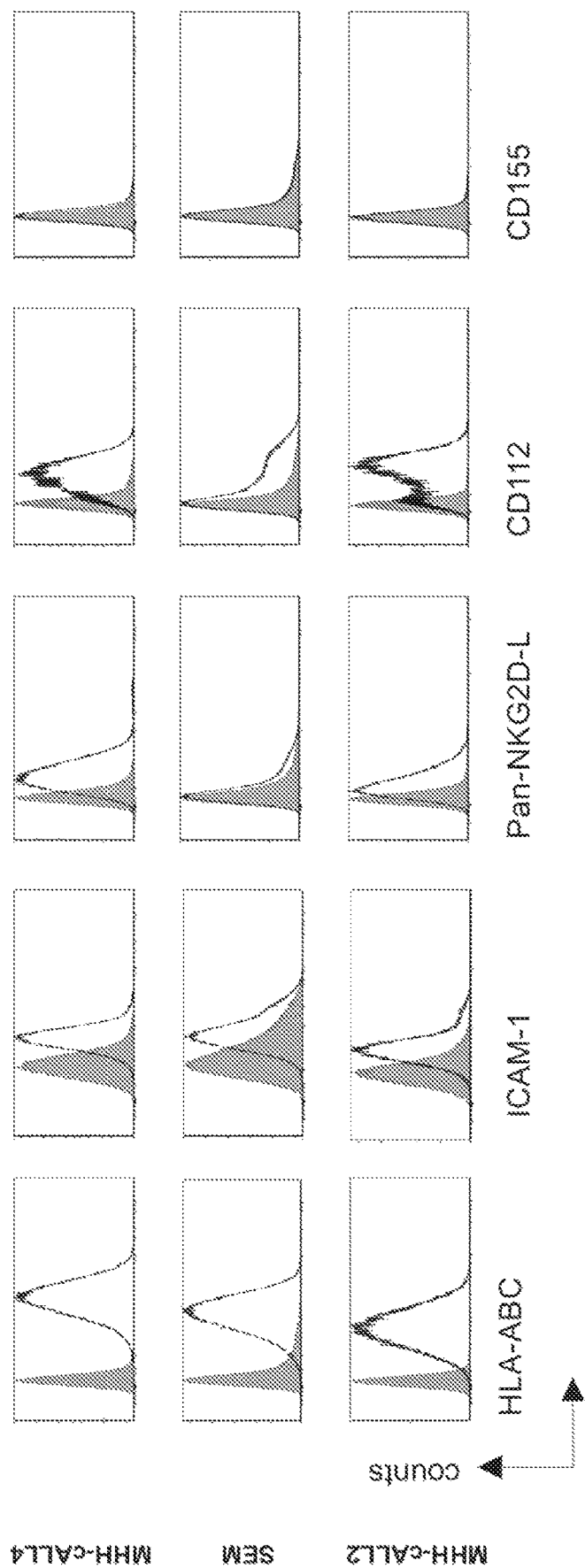
FIG. 2. NKAES cells target BCP-ALL in vitro. A: In vitro analysis of NKAES-mediated cytotoxicity towards NALM-16 cells. Data are representative of two independent experiments performed with donor SNK13B (KIR-KIRL mismatch) in triplicates (ratio of 2:1). The pediatric AML cell line Kasumi-1 was included as control. B: Phenotypic characterization of other NKG2DL$^{low}$ BCP-ALL cell lines. The flow-cytometric expression of HLA class I, ICAM-1, NKG2D or DNAM-1 ligands is shown. C: In vitro analysis of NKAES-mediated cytotoxicity towards NKG2DL$^{low}$ BCP-ALL cell lines. Data are representative of one experiment with donor SNK15B performed in triplicates (ratio of 20:1). K562 and Kasumi-1 cells were included as controls.
Figure 2C:
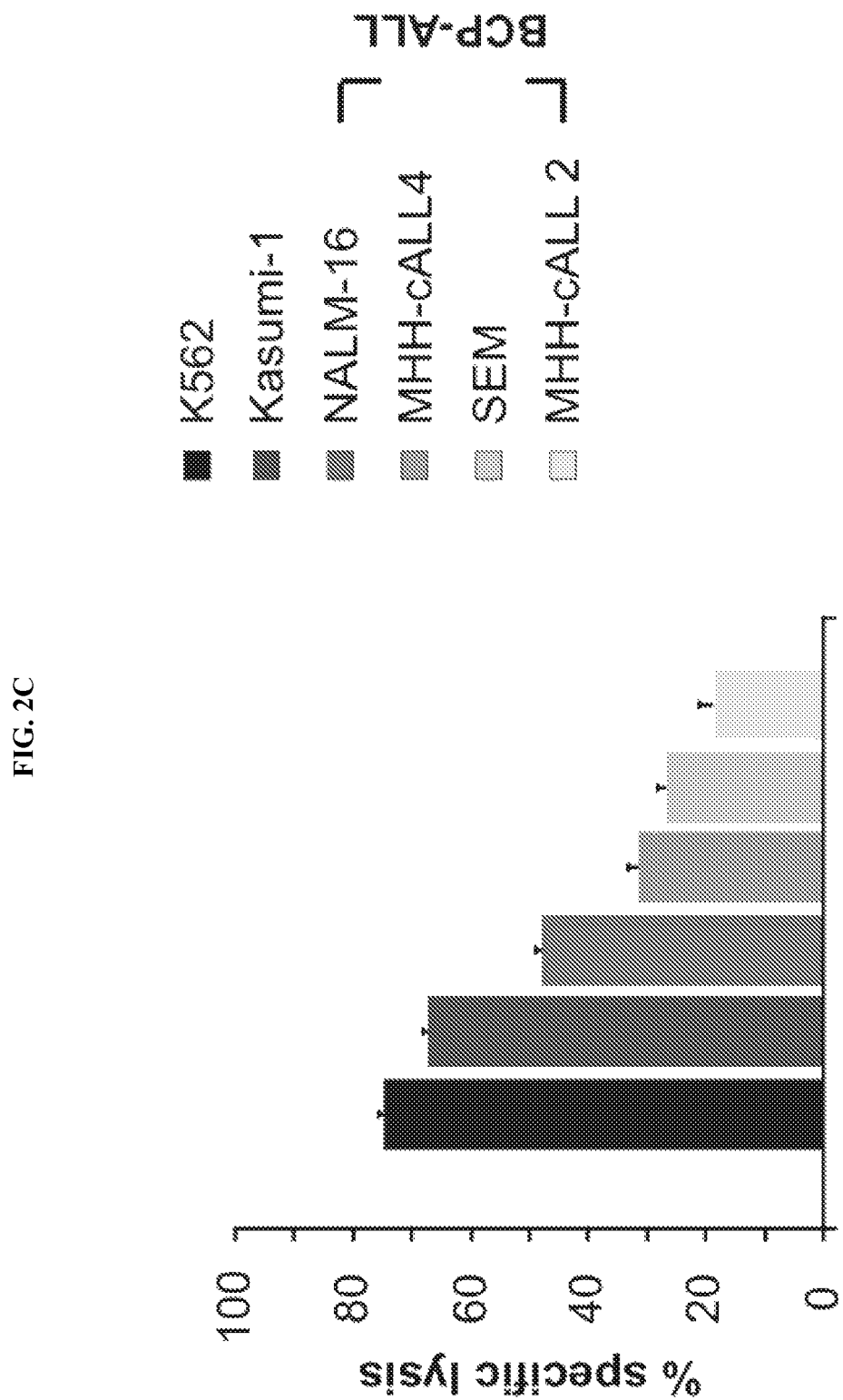
Figure 3A:
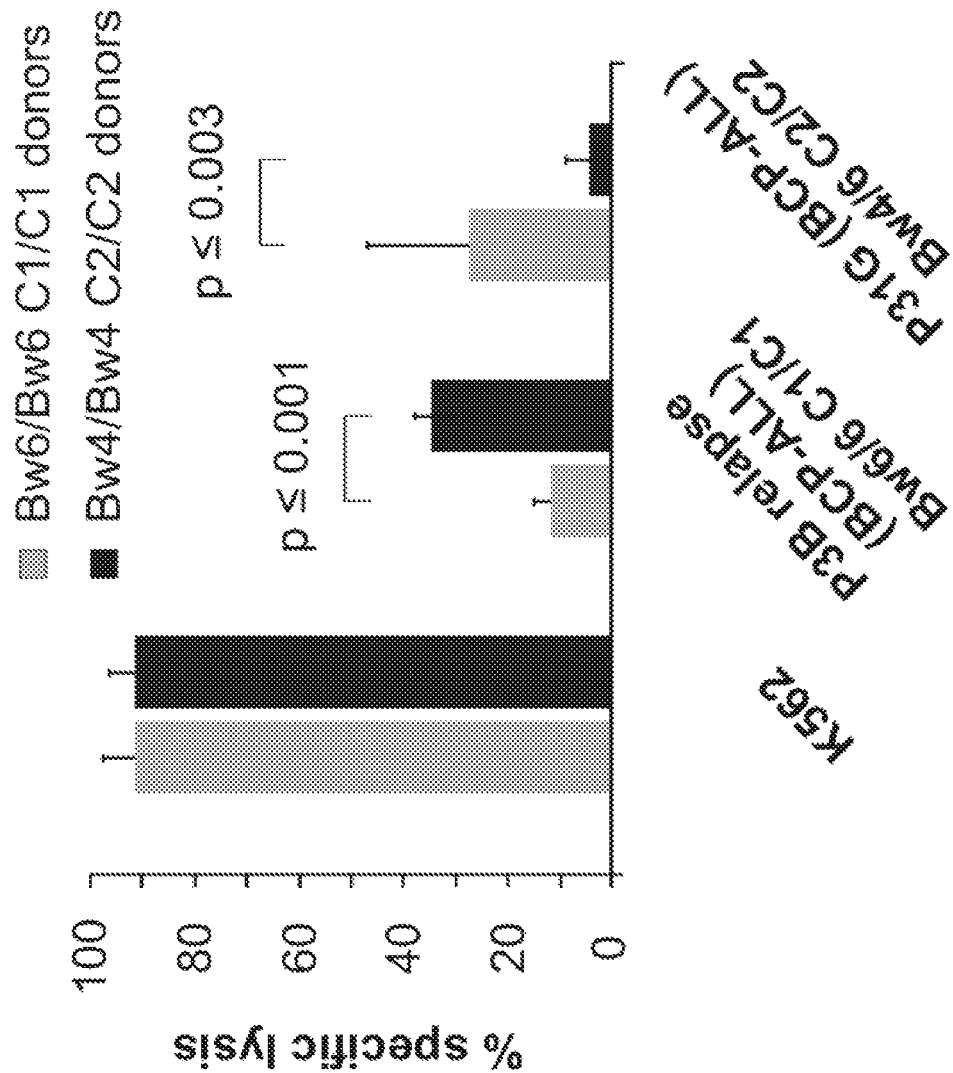
FIG. 3. KIR-KIRL mismatch constellations promote the alloreactivity of cytokine-matured NK cells towards pediatric BCP-ALL in vitro and in vivo. A: In vitro NK cell alloreactivity towards BCP-ALL is donor-dependent. The specific lysis of KIR-KIRL-mismatched or KIR-KIRL-matched donors towards the two chosen BCP-ALL samples P3B relapse and P31G (E:T ratio of 10:1) is shown. Cytotoxicity towards K562 cells is included as positive control. Data represent two independent experiments performed in triplicates. Donor/patient specific KIR-KIRL repertoire constellations of the 6 donors SNK9A, SNK10P, SNK21BC, SNK13-15B are depicted in the Table 3. B, C: Donor selection influences the in vivo alloreactivity of NKAES cells towards pediatric BCP-ALL. B: Experimental setup for part (C). C: Adoptively transferred NKAES cells of a KIR-KIRL-mismatched donor (SNK13B) exert higher in vivo alloreactivity towards P3B than control NKAES cells of a KIR-KIRL matched donor (SNK10P). Data are representative of one experiment performed with 11 mice.
Figure 3B:
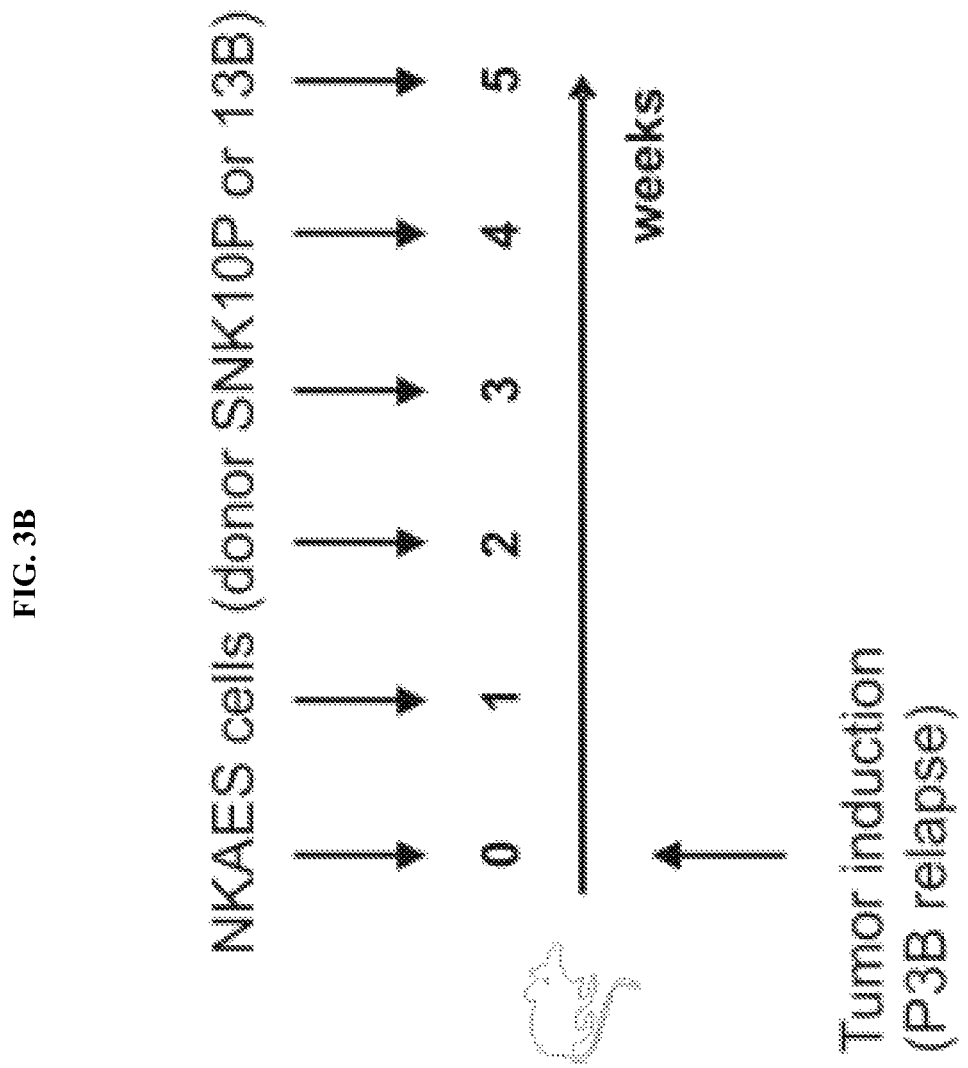
Figure 3C:
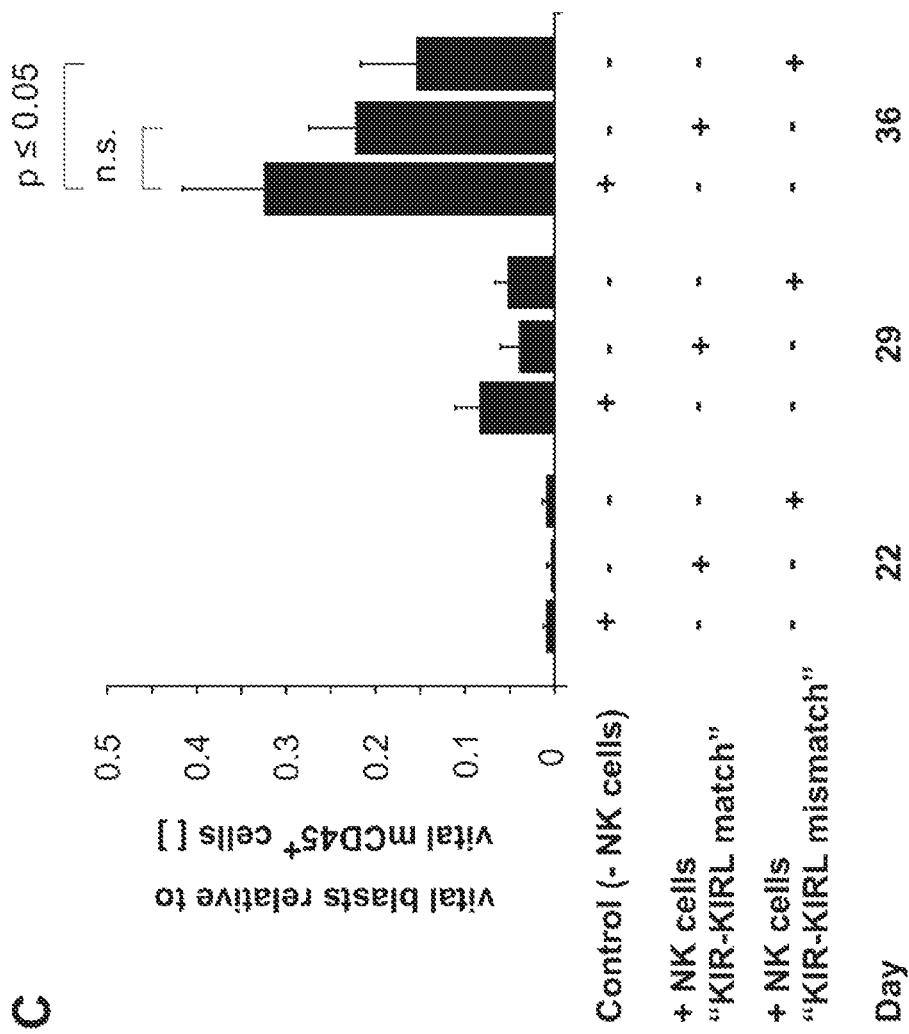

To characterize the alloreactivity of mature NK cells in various KIR-KIRL repertoire constellations, a previously described good manufacturing process (GMP)-guided NK cell activation and expansion system (NKAES) (Fujisaki et al., 2009) was used to generate large numbers of cytokine-matured NK cells of donors with defined HLA class I haplotypes (Table 1), KIR repertoires (Table 2) and NK cell surface phenotypes (FIG. 1A). A pediatric AML (Kasumi-1) and a BCP-ALL cell line (NALM-16) that express significant and comparable levels of important NK cell receptor ligands (FIG. 1B) were chosen to test whether KIR-KIRL-mismatched NK cells can target pediatric BCP-ALL. KIR-KIRL-mismatched NK cells were found to exert alloreactivity not only towards a pediatric AML but also a BCP-ALL cell line (FIG. 2A). Comparative analysis of in vitro cytotoxicity assays performed with other pediatric BCP-ALL cell lines showed that this alloreactivity was clearly dependent on the extent of NKG2DL expression (FIGS. 2B, C). To further describe the relevance of KIR-KIRL interactions that might provide functional NK cell competence in addition to the immanent NKG2D-restricted activation, cytotoxicity assays with donors that exhibited either a KIR-KIRL mismatch or a match towards two given BCP-ALL specimens (P3B relapse, P31G) (Table 3) were performed. These assays demonstrated that alloreactivity to BCP-ALL was better for those NK cells that were not subject to inhibition by self-HLA molecules (FIG. 3A). In addition, injection of NKAES cells from a KIR-KIRL-mismatched donor into P3B-engrafted NSG mice resulted in a higher reduction of tumor burden than transfer of the respective control NK cells (FIGS. 3B, C).

TABLE 1

HLA class I haplotype of donors and recipients.

|  | HLA-A allele | | KIR/KIR family | | HLA-B allele | | KIR/KIR family | | HLA-C allele | | KIR/KIR family | |
| --- | --- | --- | --- | --- | --- | --- | --- | --- | --- | --- | --- | --- |
| SNK9A | 01:01 | 33:03 | — | — | 15:25 | 55:01 | Bw6 | Bw6 | 03:03 | 07:01 | C1 | C1 |
| SNK10P | 01:01 | 02:01 | — | — | 08:01 | 40:01 | Bw6 | Bw6 | 07:01 | 03:04 | C1 | C1 |
| SNK21BC | 02:01 | 03:01 | — | 3DL2 | 07:02 | 08:01 | Bw6 | Bw6 | 07:02 | 07:01 | C1 | C1 |
| SNK13B | 02:01 | 24:02 | — | Bw4 | 27:05 | 44:02 | Bw4-80T | Bw4-80T | 02:02 | 05:01 | C2 | C2 |
| SNK14B | 02:01 | 32:02 | — | Bw4 | 27:02 | 44:02 | Bw4-80I | Bw4-80T | 02:02 | 05:01 | C2 | C2 |
| SNK15B | 02:01 | 31:01 | — | — | 27:05 | 44:02 | Bw4-80T | Bw4-80T | 02:02 | 05:01 | C2 | C2 |
| SNK20B | 02:01 | 03:01 | — | 3DL2 | 51:01 | 51:05 | Bw4-80I | Bw4-80I | 04:01 | 05:01 | C2 | C2 |
| SSC21D | 02 | 01 | — | — | 44 | 37 | Bw4 | Bw4 | 07 | 06 | C1* | C2* |
| SSC18U | 23 | 35 | Bw4 | — | 44 | 44 | Bw4-80T | Bw4-80T | 04 | 07 | C2 | C1 |
| P3B | 02:01 | 26:01 | — | — | 18:01 | 14:01 | Bw6 | Bw6 | 07:01 | 08:02 | C1 | C1 |
| P23T | 24:02 | — | Bw4 | — | 49:01 | 51:01 | Bw4-80I | Bw4-80I | 02:02 | 07:01 | C2 | C1 |
| P31G | 03x | 03x | 3DL2 | 3DL2 | 27x | 35x | Bw4-80T* | Bw6* | 02:02x | 04x | C2 | C2* |
| Nalm-16 | 30:01 | — | — | — | 44:02 | — | Bw4-80T | — | 07:04 | — | C1 | — |
| Kasumi-1 | 26:01 | 26:02 | — | — | 40:06 | 48:01 | Bw6 | Bw6 | 03:03 | 08:01 | C1 | C1 |

Specific information on the HLA-typing data and the resulting KIR family member grouping are tabulated.
HLA class I genotypes were determined at 4-digit resolution by SBT (sequence-based typing), except for P23T which was determined at 4-digit resolution by SSP (sequence-specific primer typing).
Only SSC21D was assessed by SSO (sequence specific oligonucleotide typing) in 2-digit resolution.

TABLE 2

KIR DNA genotype, RNA expression, B content score, haplotype and KIR3DL1 surface expression of donors and patients included in this study.

|  | B-content score | KIR Genotype | Cen | Tel | 2DL1 | | 2DL2 | | 2DL3 | | 2DL4 | | 2DL5 | | 3DL1 |
| --- | --- | --- | --- | --- | --- | --- | --- | --- | --- | --- | --- | --- | --- | --- | --- |
|  |  |  |  |  | * | ○ | * | ○ | * | ○ | * | ○ | * | ○ | # |
| SNK9A | 2 | B/x | A/B | A/B | = | = | = | = | = | = | = | = | = | = | + |
| SNK10P | 0 | A/A | A/A | A/A | = | = |  |  | = | = | = | = |  |  | + |
| SNK21BC | 1 | B/x | A/B | A/A | = | = | = | = | = | = | = | = | = | = | ++ |
| SNK13B | 2 | B/x | A/B | A/B | = | = | = | = | = | = | = | = | = | = | − |
| SNK14B | 1 | B/x | A/B | A/A | = | = | = | = | = | = | = | = | = | = | ++ |
| SNK15B | 0 | A/A | A/A | A/A | = | = |  |  | = | = | = | = |  |  | + |
| SNK20B | 1 | B/x | A/B | A/A | = | = | = | = | = | = | = | = |  |  | ++ |

TABLE 2-continued

| | | | | | | | | | | | | | | | | | |
|---|---|---|---|---|---|---|---|---|---|---|---|---|---|---|---|---|---|
| SSC21D | 1 | B/x | A/A | A/B | = | ND | | ND | = | ND | = | ND | = | ND | = | ND | ND |
| SSC18U | 0 | A/A | A/A | A/A | = | = | | | = | | = | | = | | = | = | (+) |

| | 3DL2 | | 3DL3 | | 2DS1 | | 2DS2 | | 2DS3 | | 2DS4 | | 2DS5 | | 3DS1 | |
|---|---|---|---|---|---|---|---|---|---|---|---|---|---|---|---|---|
| | * | ° | * | ° | * | ° | * | ° | * | ° | * | ° | * | ° | * | ° |
| SNK9A | = | = | = | = | = | = | = | = | | | = | = | = | = | = | = |
| SNK10P | = | = | = | = | | | | | | | = | = | | | | |
| SNK21BC | = | = | = | = | | | | | = | = | = | = | = | = | | |
| SNK13B | = | = | = | = | | | = | = | = | = | = | = | | | | |
| SNK14B | = | = | = | = | | | | | = | = | = | = | | | | |
| SNK15B | = | = | = | = | | | | | | | = | = | | | | |
| SNK20B | = | = | = | = | | | = | = | | | = | = | | | | |
| SSC21D | = | ND | = | ND | ≡ | ND | | ND | | ND | = | ND | = | ND | = | ND |
| SSC18U | = | = | = | = | | | | | | | = | = | | | | |

*-KIR DNA genotype (Q-PCR); °-KIR RNA expression (Q-PCR); and #-3DL1 protein expression (flow cytometry, clone DX9). ■ = present, □ = absent, ND = not determined. +: low, ++: positive, +++: strong and –: absent expression.

TABLE 3

KIR-KIRL repertoire constellations of donors and patients included in this study.

| | | Donor education of inhibitory KIRs | | KIR phenotype of alloreactive NK cell subset against | | | |
|---|---|---|---|---|---|---|---|
| | | | | P3B<br>A02:01/26:01 | P23T<br>A24:02/24:02 | P31G<br>A03:01/A03:01 | Nalm-16<br>A30:01 Bw4 |
| | | Educated | Uneducated | Bw6/Bw6 C1/C1 | Bw4/Bw4 C2/C1 | Bw4/Bw6 C2/C2 | C1* |
| Donor group "match" | SNK9A | 2DL2, 2DL3 | 2DL1, 3DL1, 3DL2 | / | N/A | 2DL2, 2DL3 | — |
| | SNK10P | 2DL2, 2DL3 | 2DL1, 3DL1, 3DL2 | / | N/A | 2DL2, 2DL3 | — |
| | SNK21BC | 2DL2, 2DL3, 3DL2 | 2DL1, 3DL1 | 3DL2 | N/A | 2DL2, 2DL3 | 3DL2 |
| Donor group "mismatch" | SNK13B | 2DL1, ** | 2DL2, 2DL3, 3DL2 | 2DL1, ** | N/A | / | 2DL1 |
| | SNK14B | 2DL1, 3DL1 | 2DL2, 2DL3, 3DL2 | 2DL1, 3DL1 | N/A | / | 2DL1 |
| | SNK15B | 2DL1, 3DL1 | 2DL2, 2DL3, 3DL2 | 2DL1, 3DL1 | N/A | / | 2DL1 |
| | SNK20B | 2DL1, 3DL1, 3DL2 | 2DL2, 2DL3 | 2DL1, 3DL1, 3DL2 | N/A | / | 2DL1, 3DL2 |
| | SSC21D | 2DL1, 2DL3, 3DL1***, **** | 3DL2 | 2DL1, 3DL1 | / | N/A | N/A |
| | SSC18U | 2DL1, 2DL3, 3DL1, *** | 3DL2 | 2DL1, 3DL1 | N/A | N/A | N/A |

The internal de-identification codes of the NK cell donors (SNK), stem cell donors (SSC), the donor-specific inhibitory KIR repertoire relevant for characterization of the alloreactive subset and the KIRL repertoire of the respective BCP-ALL are provided.
Note that KIR2DL1 and KIR2DL2/3 KIR family members recognize HLA-C alleles with Lys$^{80}$ (C2 epitope) or Asn$^{80}$ (C1 epitope) residues, respectively, whereas KIR3DL1 recognizes HLA-A and B alleles with a Bw4 supertypic specificity and KIR3DL2 recognizes HLA-A3 and HLA-A11 alleles.
For detailed KIR ligand status and KIR expression data see Tables 1 and 2.
*—Monoallelic data as the NALM-16 cell line has a near-haploid genome.
**—In contrast to theoretical assumptions, this donor does not express KIR3DL1 on the NK cell surface and does, therefore, lack a KIR3DL1 alloreactive NK cell subset.
***—The assumption of KIR3DL1 is based on genomic data as huNSG mice lacked inhibitory KIR expression.
****—Genomic expression of KIR 2DL2 is absent in this donor.
N/A = not applicable.

EXAMPLE 2

KIR+ NK Cell Subset of KIR-KIRL-Mismatched Donors Exerts Higher Cytotoxicity Towards BCP-ALL than Corresponding KIR− Subset Methods Determination of In Vitro Cytotoxicity In vitro cytotoxicity was assayed as described in Example 1. To determine the effect of KIR blockade, the cross-reactive, inhibitory KIR2DL1 and KIR2DL2/L3-blocking mAb, lirilumab, generously provided by Bristol-Myers Squibb, (Princeton, N.J.) was added to the NKAES cells 30 min prior to the addition of NALM-16 cells (final concentration of 15 µg/ml). Following staining with ARD-Ax350, cells were washed and analyzed.

Results

Figure 4A:
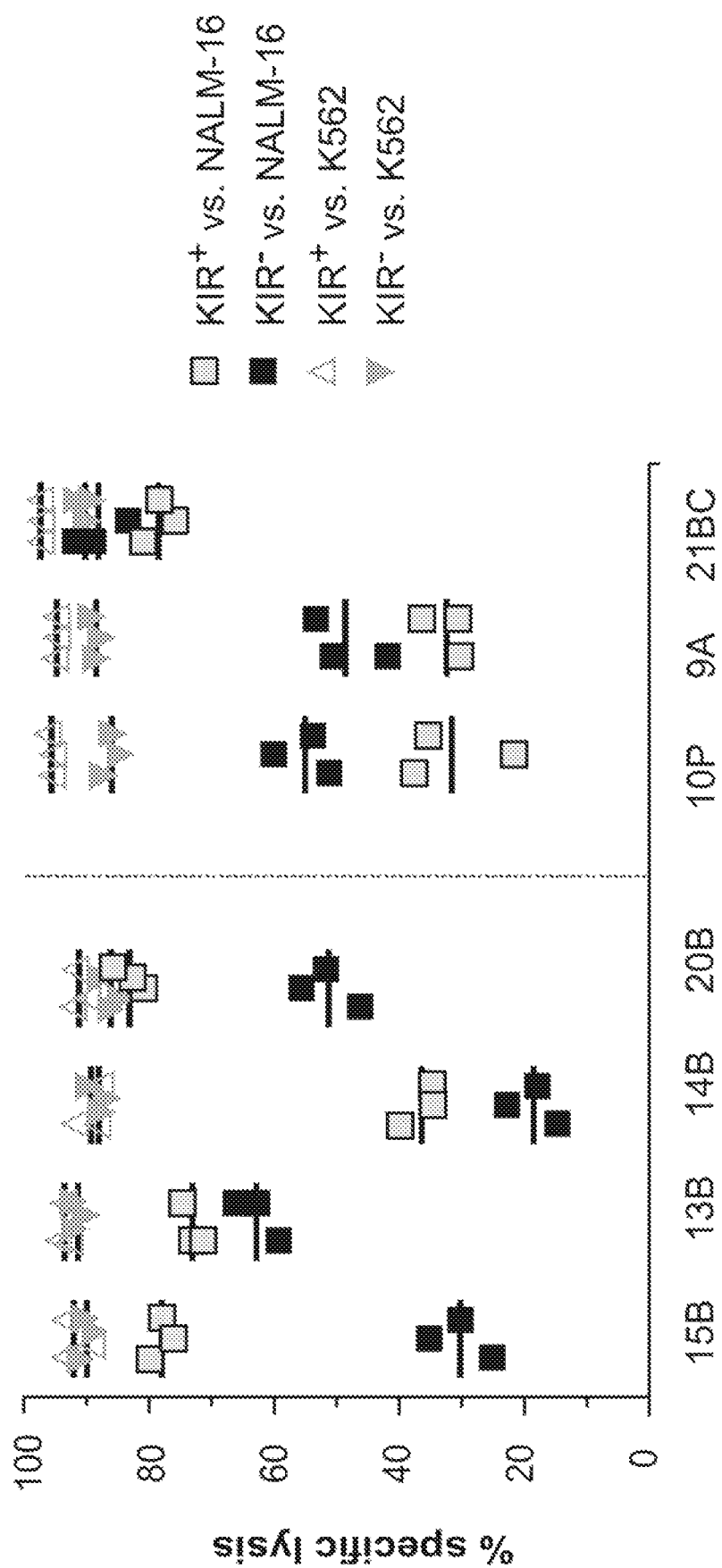
FIG. 4. The KIR$^+$ NK cell subset of KIR-KIRL-mismatched donors exerts higher cytotoxicity towards pediatric BCP-ALL than the corresponding KIR$^-$ subset. A: Sorted KIR$^+$ and KIR$^-$ NK cells of the 7 donors characterized in Table 3 were co-cultured with NALM-16 or K562 cells as a control to determine the extent of in vitro cytotoxicity (E:T ratio 5:1). B: Standardization of the data depicted in part (A). The specific lysis of the KIR$^+$ NK cell subset minus the corresponding KIR$^-$ NK cell subset is shown. Data represent six independent experiments with 7 donors performed in triplicates. C: Interactions of inhibitory KIRs with their cognate ligands determine the extent of NK alloreactivity towards pediatric BCP-ALL. Alloreactivity of sorted KIR$^+$ NKAES cells of the donors SNK14B, SNK15B, SNK20B, SNK10P and SNK21BC against NALM16 was determined by in vitro killing assays (E:T ratio 2:1) in the presence or absence of the common inhibitory KIR-blocking mAb IPH2102. Data represent five independent experiments performed in triplicates.
Figure 4B:
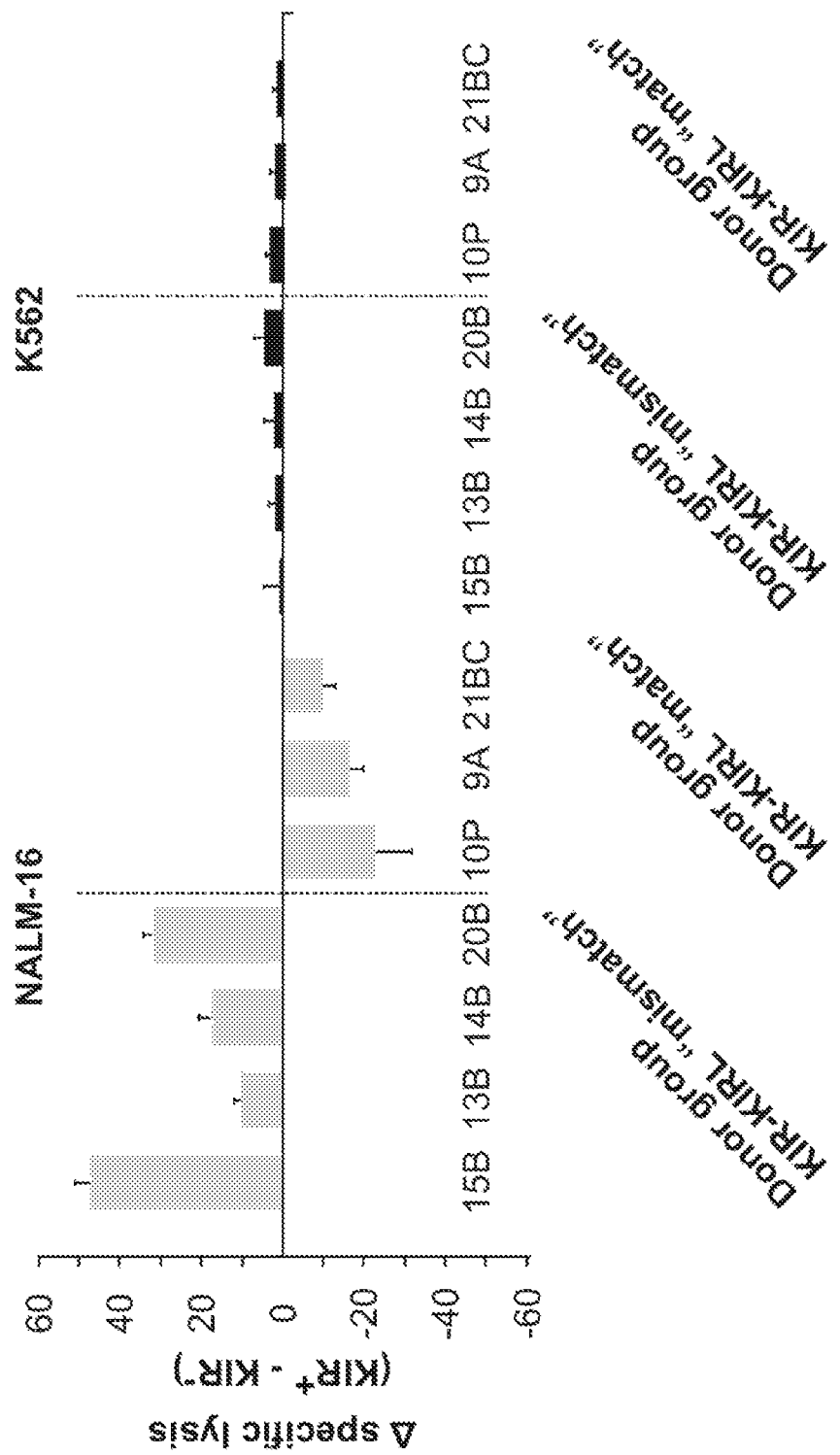
Figure 4C:
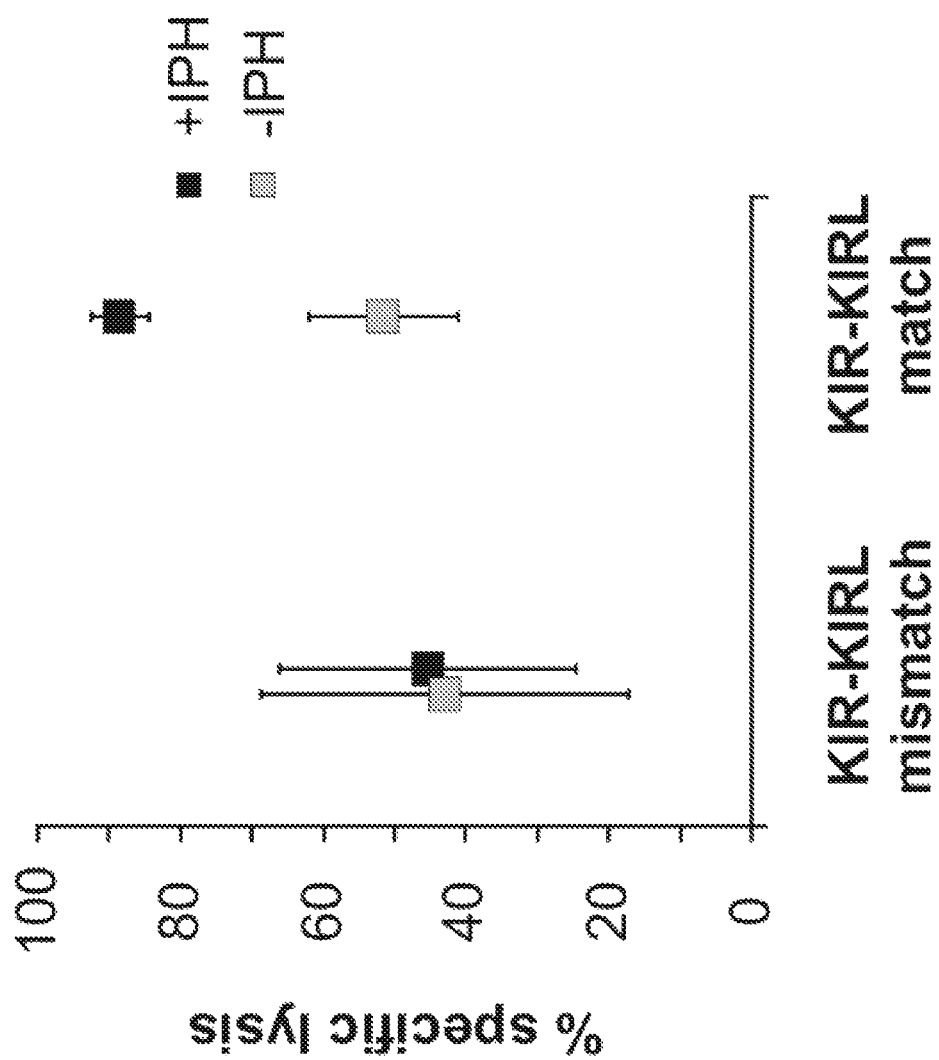

To further characterize the functional repertoire of NKAES cells with regard to potential KIR-KIRL mismatch constellations, KIR+ and KIR− NK cell subsets were sorted. The KIR+ NK cell subset of KIR-KIRL-mismatched donors uniformly demonstrated higher levels of cytotoxicity when compared to the respective KIR− controls (FIG. 4A), a phenomenon that became even more evident upon normalization (FIG. 4B). In contrast, the KIR+ NK cells of matched donors invariably exhibited impaired cytotoxicity, indicating that functionality might have been compromised in response to inhibitory KIR-KIRL interactions. Cytotoxicity assays were performed in the presence of lirilumab, a mAb that is cross-reactive with, and blocks, both the inhibitory KIR2DL1 and 2DL2/3 receptors. These assays revealed that the lytic activity of KIR+ NK cells of KIR-KIRL-matched, HLA-C1 homozygous donors must have been controlled by inhibitory interactions of educated KIR2DL2 and 2DL3 receptors with their respective HLA-C1 group ligands expressed on NALM-16 cells (FIG. 4C). In contrast, the KIR2DL2 and 2DL3+ NK cell subset of the KIR-KIRLmismatched, HLA-C2 homozygous donors is considered to be uneducated and, thus, did not respond to inhibitory KIR blockade.

EXAMPLE 3

Educated, Alloreactive KIR+ NK Cell Subset of KIR-KIRL-Mismatched Donors Exhibits a Superior Ability for Degranulation in Response to Pediatric BCP-ALL Methods Functional NK Cell Response Staining Sorted KIR+ and KIR− NKAES subsets (sorting KIR mAb: anti-CD158a (clone HP-3E4 recognizing KIR2DL1/S1/S4), anti-CD158b (clone GL183 recognizing KIR2DL2/L3/S2) and anti-CD158e (clone DX9 recognizing 3DL1)) were co-cultured for 6 h with NALM-16 or K562 cells (E:T ratio of 1:2) in the presence of CD107a-APC (H4A3) (BD Pharmingen). Subsequently, NK cells were stained with the indicated surface antibodies, permeabilized and co-stained with the respective intracellular antibodies (Perforin-PB (dG9) and TNF-bv605 (MAb11)) (Biolegend). For determination of IFN-γ, unsorted NKAES cells were co-cultured with the respective target cells, subsequently stained with surface antibodies (including the above-mentioned anti-KIR Ab cocktail), and finally stained with IFN-γ-BUV395 (B27) Ab (BD Horizon). Percentages of the respective NK cell subpopulation were then normalized to the baseline levels of NKAES cells cultured in control medium only. The specificity of the intracellular perforin staining was additionally verified by determining the perforin concentration in the co-culture supernatants using the Diaclone Perforin ELISA KIT (ACTIVE BIOSCIENCE, Germany).

Alloreactive NK Cell Subset Analysis

Unsorted NKAES cells were co-cultured with the respective target cells in the presence of CD107a-bv421 (H4A3) and subsequently stained with the following mAbs: KIR3DL1 (DX9, BD Pharmingen), KIR2DL2/L3/S2 (GL183, Beckman Coulter), KIR3DL1/S1 (Z27.3.7, Beckman Coulter) and KIR2DL1/S1/S4 (HP-3E4, BD Pharmingen). The selective combination of anti-KIR mAbs with different or identical fluorochromes allowed the discrimination KIR− and non-alloreactive or alloreactive KIR+ NK cell subsets in the context of Bw4/C1 target cell recognition.

Figure 5A:
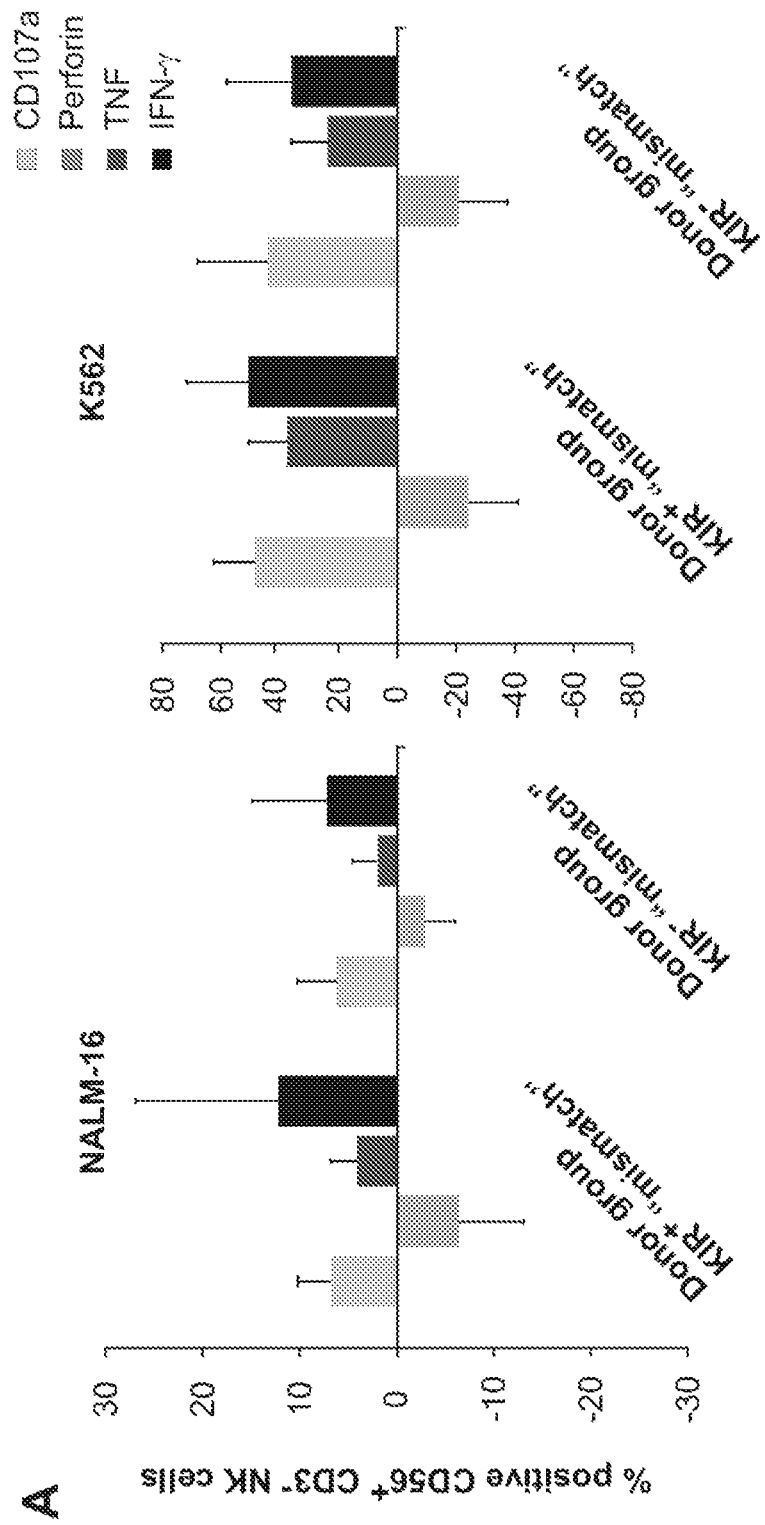
FIG. 5. The educated, alloreactive KIR$^+$ NK cell subset of KIR-KIRL-mismatched donors exhibits a superior ability for degranulation in response to pediatric BCP-ALL. A: Sorted KIR$^+$ and KIR$^-$ NK cells of the 4 donors SNK13-15B and SNK20B (donor group "mismatch") were co-cultured with NALM-16 or K562 cells as a control to determine the functional response in terms of degranulation and cytokine synthesis. Pooled data of the intracellular staining showing mean±SEM. Given are the percentages of the respective CD107a$^+$, Perforin$^+$, TNF$^+$ and IFN-γ$^+$ NK cell subpopulation normalized to the corresponding baseline levels of NKAES cells cultured in control medium only. Due to the genuinely higher response the y-axis is differently scaled in K562 experiments. The negative bars indicate the decline in perforin levels that is accompanied by NK cell degranulation. B-E: NKAES cells of KIR-KIRL-mismatched or -matched donors, respectively, were co-cultured with NALM-16 or K562 cells. The percentage CD107a$^+$ CD56$^+$ population in various alloreactive or non-alloreactive NK cell subsets is shown. B: Exemplified gating strategy for the identification of NK cells subsets. In relation to NALM-16 cells (Bw4/C1), the potentially alloreactive NK cell population (upper left quadrant) is represented by the cells expressing KIR 2DL1/S1/S4 and/or KIR 3DS1 (y-axis) but not KIR 2DL2/L3/S2 or KIR 3DL1 (x-axis). (Note, that the combined staining with a KIR3DL1/S1 and a KIR3DL1 Ab enables the identification of the KIR3DL1$^-$S1+ cell population that belongs to the alloreactive subset). C, D: Representative original histogram data obtained from a KIR-KIRL-mismatched (SNK15B) and a matched donor (SNK10P). Data in (C) show staining with the indicated antigen-specific mAb in unstimulated (light grey, open) and NALM-16-stimulated NKAES cells (black, open) or the corresponding isotype controls (filled). Data in (D) show the respective staining in K562-stimulated NKAES cells (black, open) or the respective isotype controls (grey, filled). E: Percentage CD107a$^+$ CD56$^+$ cells in the indicated NK cells subsets of KIR-KIRL-mismatched (SNK14B, SNK15B and SNK20B) or -matched donors (SNK9A, SNK10P and SNK21BC). The increase in CD107a expression of NALM-16 co-cultured KIR$^+$ NK cell subsets, normalized to the CD107a expression of the corresponding KIR$^-$ NK cell subset, is shown. The KIR$^+$ alloreactive subset in KIR-KIRL-mismatched donors is considered to be educated (●) while the corresponding NK cell subset in matched donors is per definition uneducated (○). The KIR$^+$ non-alloreactive NK cell subset is denoted with ■. Data represent one experiment performed with 6 donors.
Figure 5B:
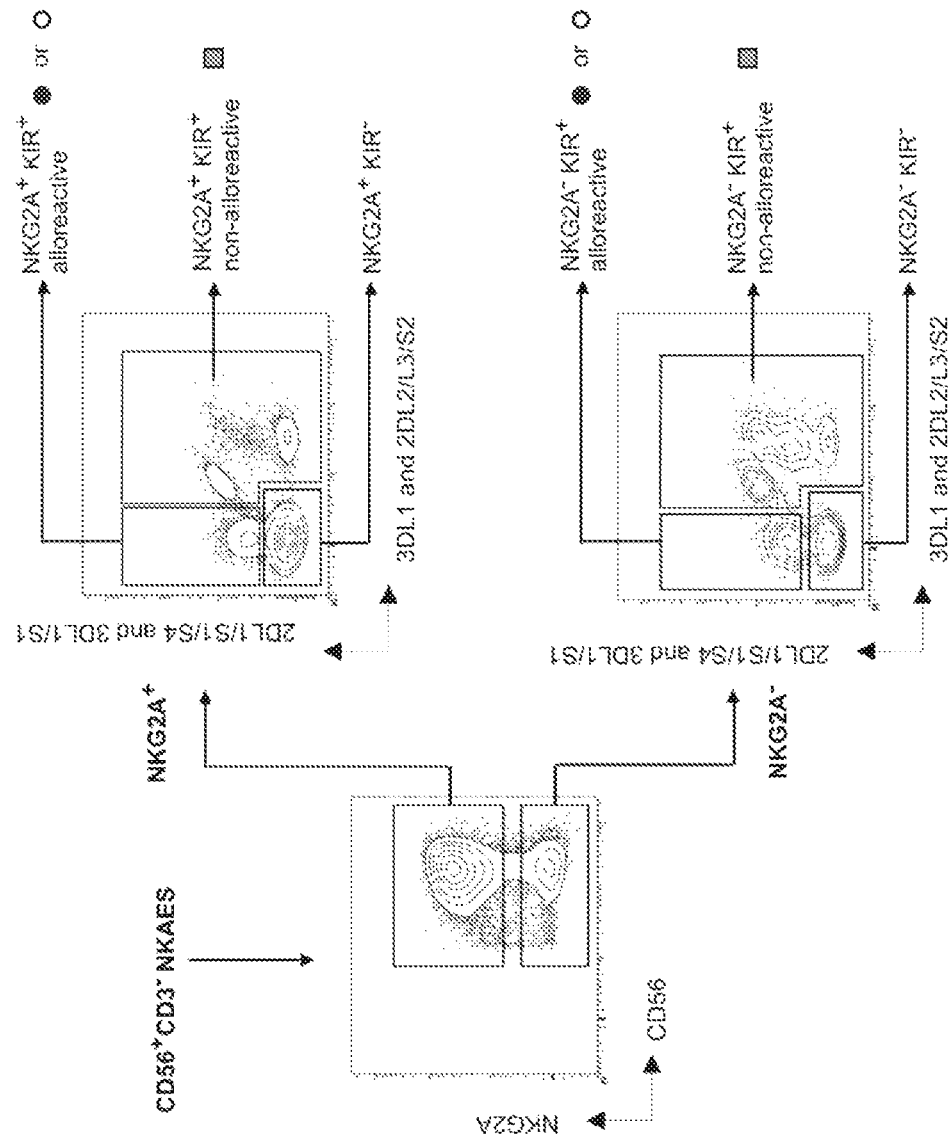
Figure 5C:
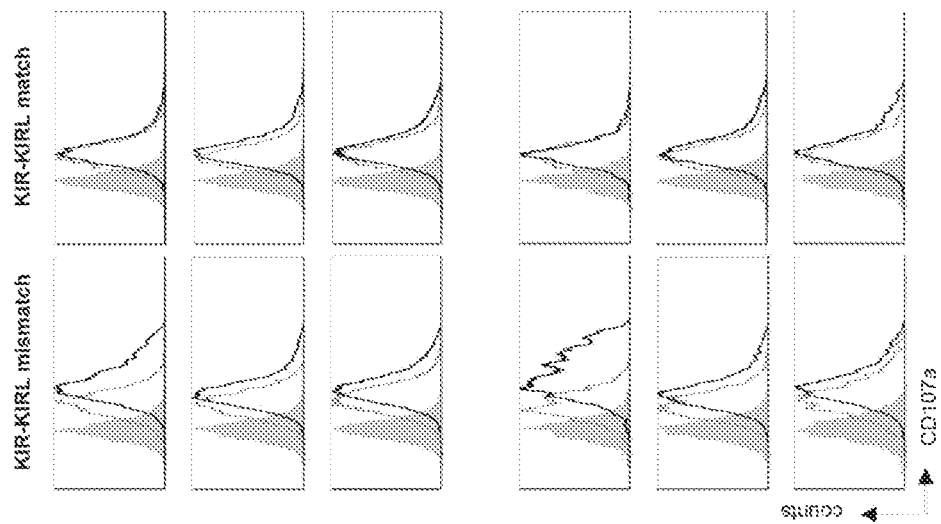
Figure 5D:
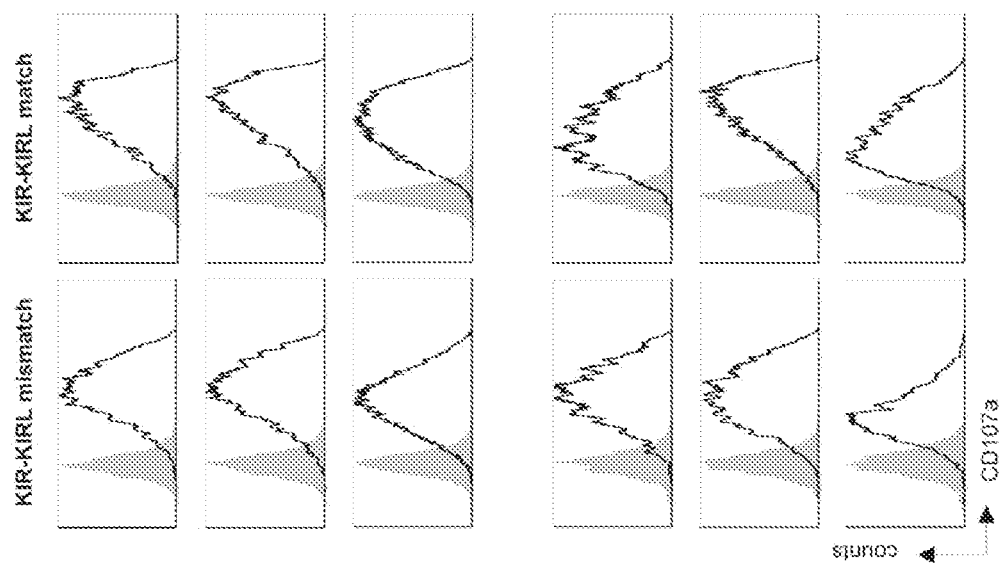
Figure 5E:
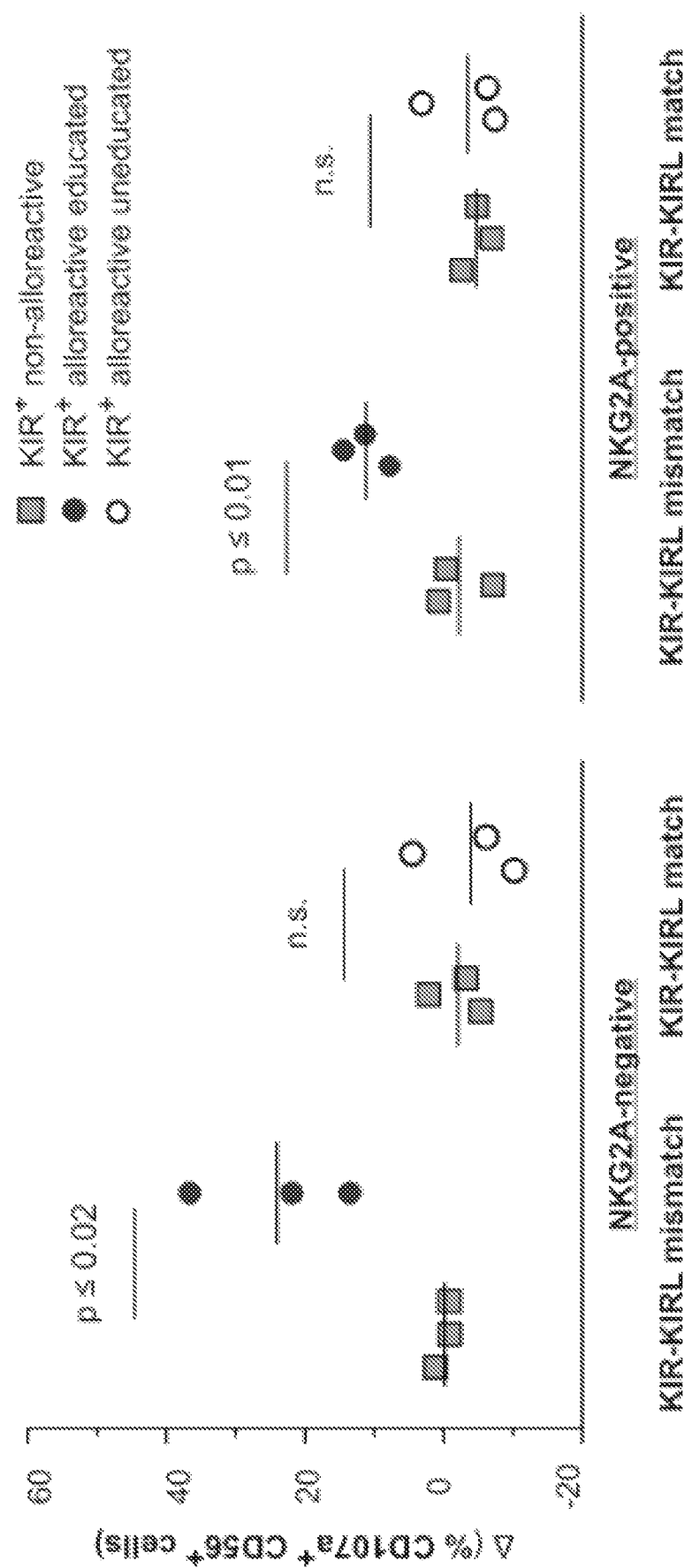
Figure 6:
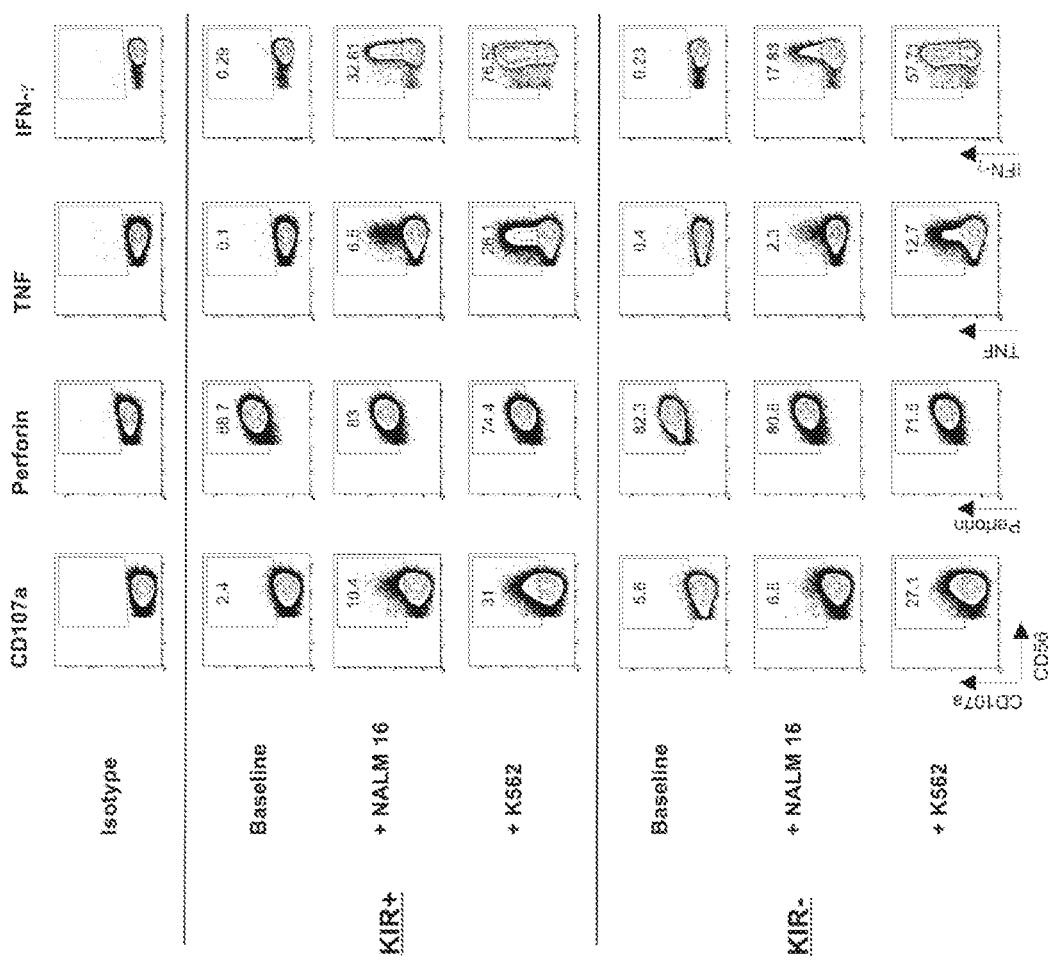
FIG. 6. Phenotypical appearance of KIR$^+$ and KIR$^-$ NK cell subsets in the functional response analysis. Original dot plot data of the KIR-KIRL-mismatched donor SNK15B.
Figure 7:
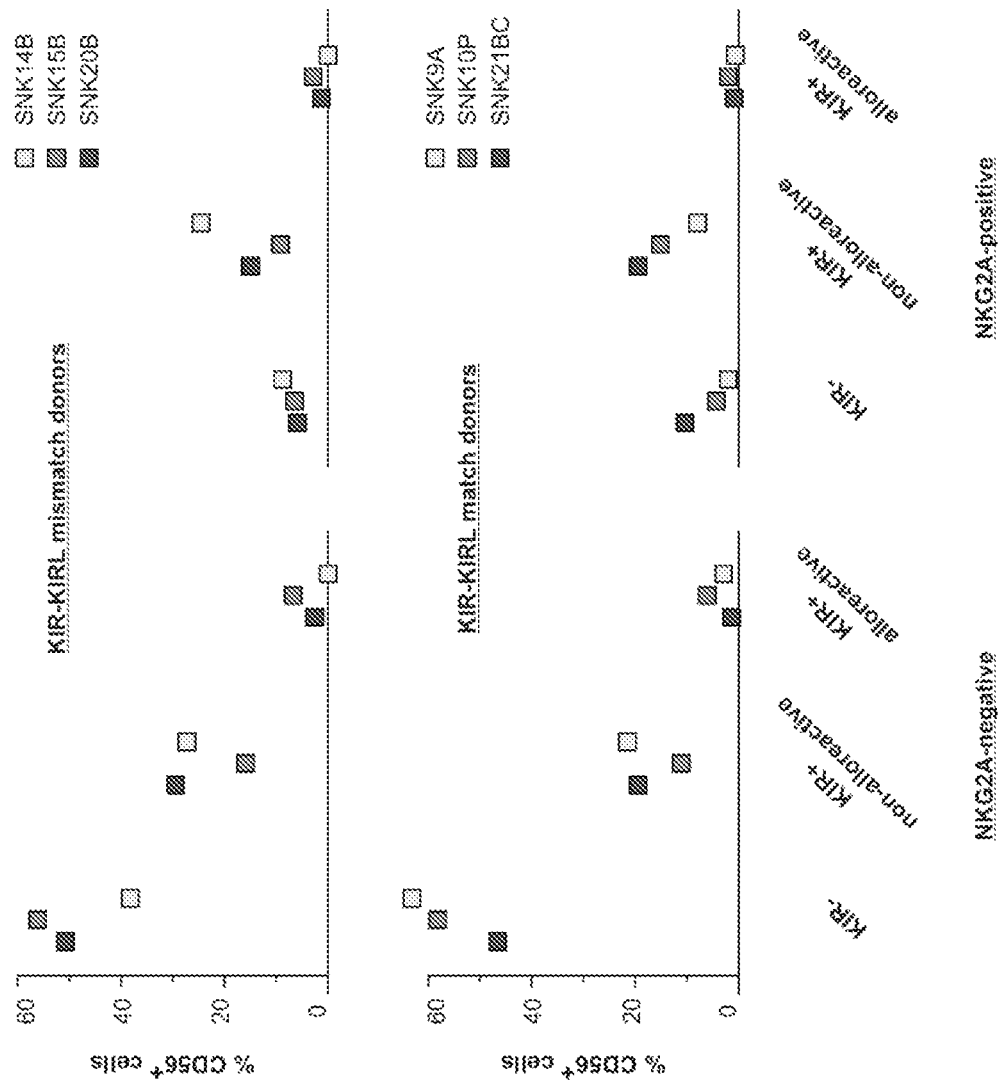
FIG. 7. Characterization of the pool size of various NK cell subsets: Quantification of various NK cell subsets. The percentage CD56$^+$ cells in the indicated NK cells subsets of KIR-KIRL-mismatched (SNK14B, 15B and 20B) or KIR-KIRL-matched donors (SNK9A, 10P and 21BC) is shown.

Facing this high cytotoxic activity of KIR+ NK cells towards KIRL-negative BCP-ALL target cells, significant differences in assays quantifying the ability for cytokine secretion or degranulation would be expected. Indeed, KIR-KIRL mismatch constellations boosted to some extent the ability of KIR+ NK cells to exhibit both cytokine secretion and degranulation (FIGS. 5A and 6); however, these data did not reach statistical significance. Therefore, to further dissect the extent of anti-tumor responses of KIR+ NK cells, the capacity for degranulation in the alloreactive and non-alloreactive NK cell subset was analyzed (FIG. 5B). In line with the assumption that the acquisition of NK cell effector functions is determined by the HLA milieu, educated and alloreactive KIR+ NK cells from mismatched donors revealed a superior capacity for degranulation in comparison to uneducated, alloreactive KIR+ NK cells from matched donors (FIGS. 5C-E). This was the case for the KIR+ NKG2A− NK cell subset but, to some extent, also for the cytokine-activated and thus expanded KIR+NKG2A+ subset. Interestingly, the KIR-KIRL-mismatched donor SNK14B had very little alloreactive, educated KIR+ NK cells (FIG. 7), explaining the comparatively poor killing ability depicted in FIG. 4A. It was therefore concluded that cytokine-matured NK cells of KIR-KIRL-mismatched donors can exert a substantial cytotoxicity towards pediatric BCP-ALL cells which is, above all, conferred by vivid degranulation of educated, alloreactive KIR+ NK cells.

EXAMPLE 4

Immature, KIR− NK Cells Exert Alloreactivity Towards Pediatric BCP-ALL

Figure 8A:
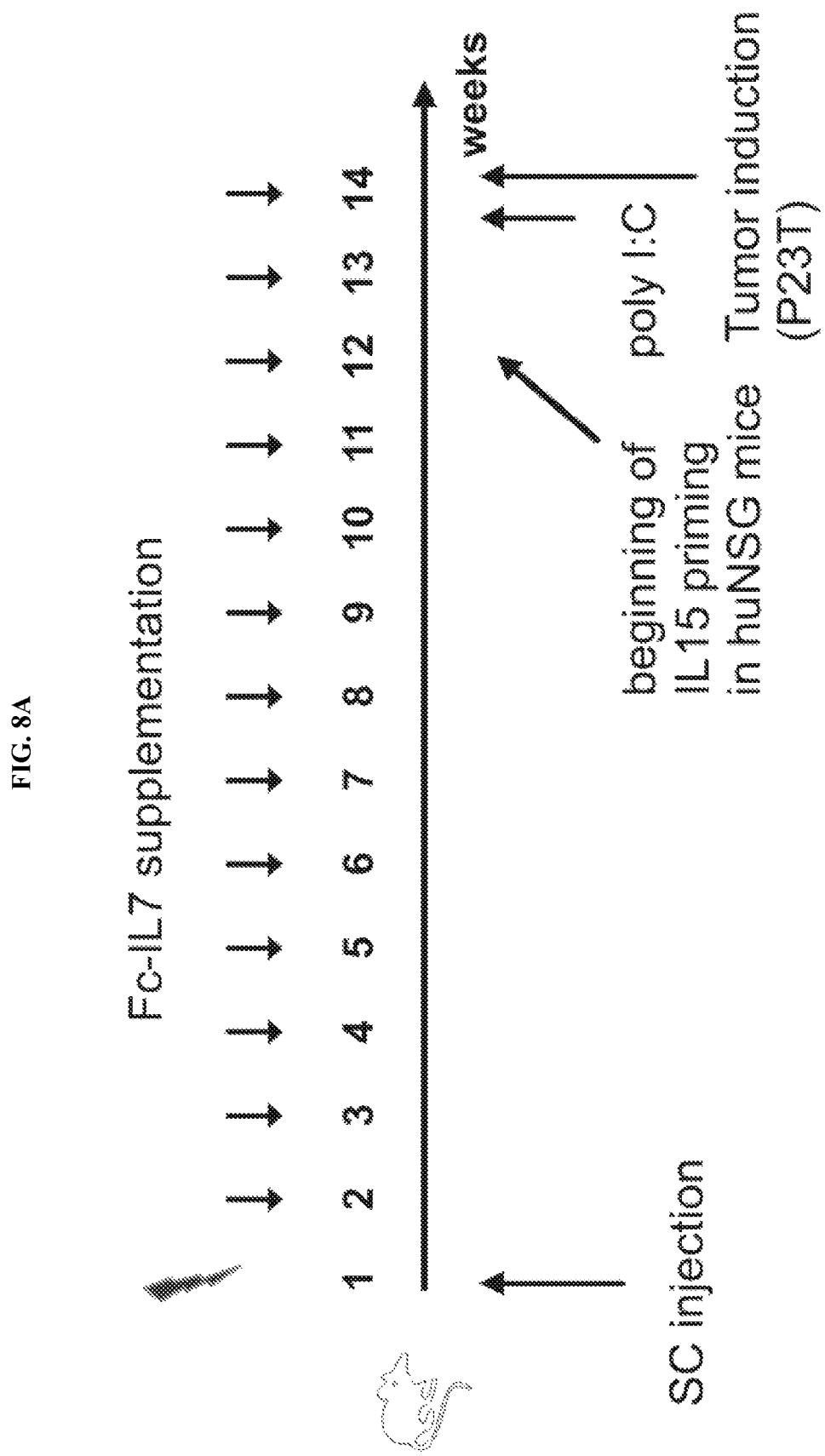
FIG. 8. Immature, KIR$^-$ NK cells exert alloreactivity towards pediatric BCP-ALL in vivo. A: Experimental setup for humanization of NSG mice. B: NSG mice transplanted with human hematopoietic stem cells (huNSG mice) exhibit alloreactivity towards pediatric BCP-ALL in vivo. P23T was injected into huNSG or non-humanized control mice and leukemic burden was quantified 20 h later in the bone marrow (BM). The number of vital blasts normalized to vital murine CD45$^+$ cells is given. The figure represents pooled data of two independent experiments obtained on a total of 7 huNSG and 3 control mice. C: Experimental setup for parts (D) and (E). D: Expression of common inhibitory KIRs (KIR2DL1, 2DL2/3) on BM-derived CD56$^+$ NK cells of huNSG mice. E: HuNSG-derived NK cells from SSC21D exert significantly higher in vivo alloreactivity against P3B than towards P23T. The number of BM-residing vital blasts, normalized to vital murine CD45$^+$, is given. Data are representative of two independent experiments with a total of 4 huNSG mice.
Figure 8B:
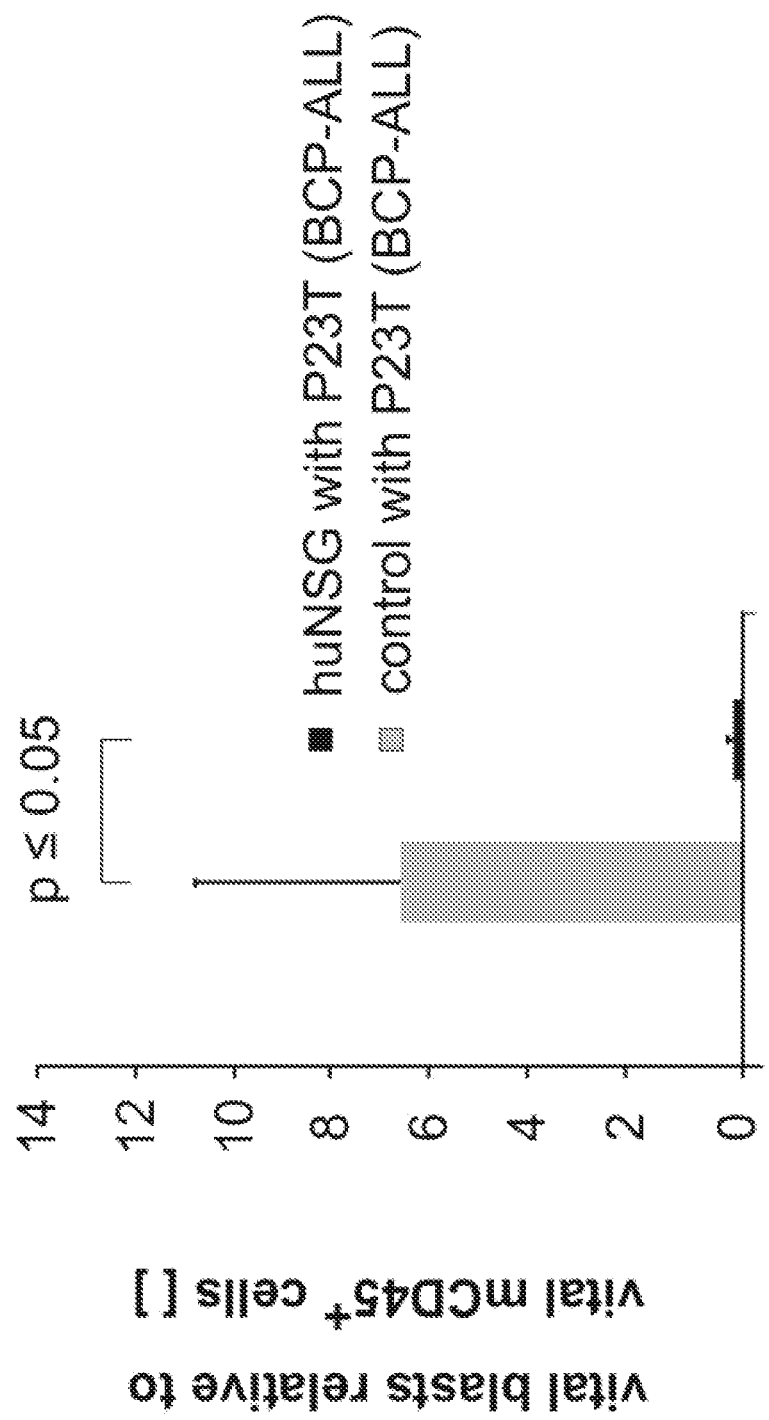
Figure 8C:
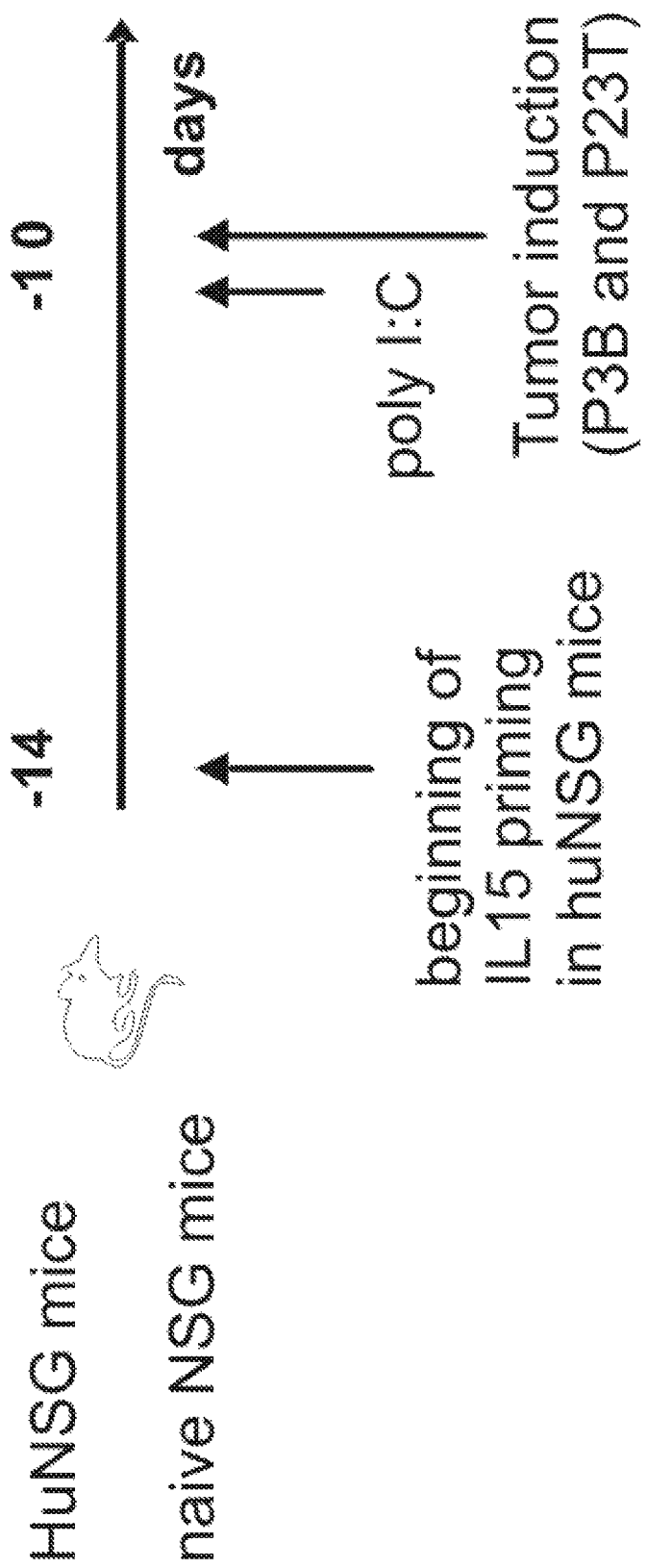
Figure 8D:
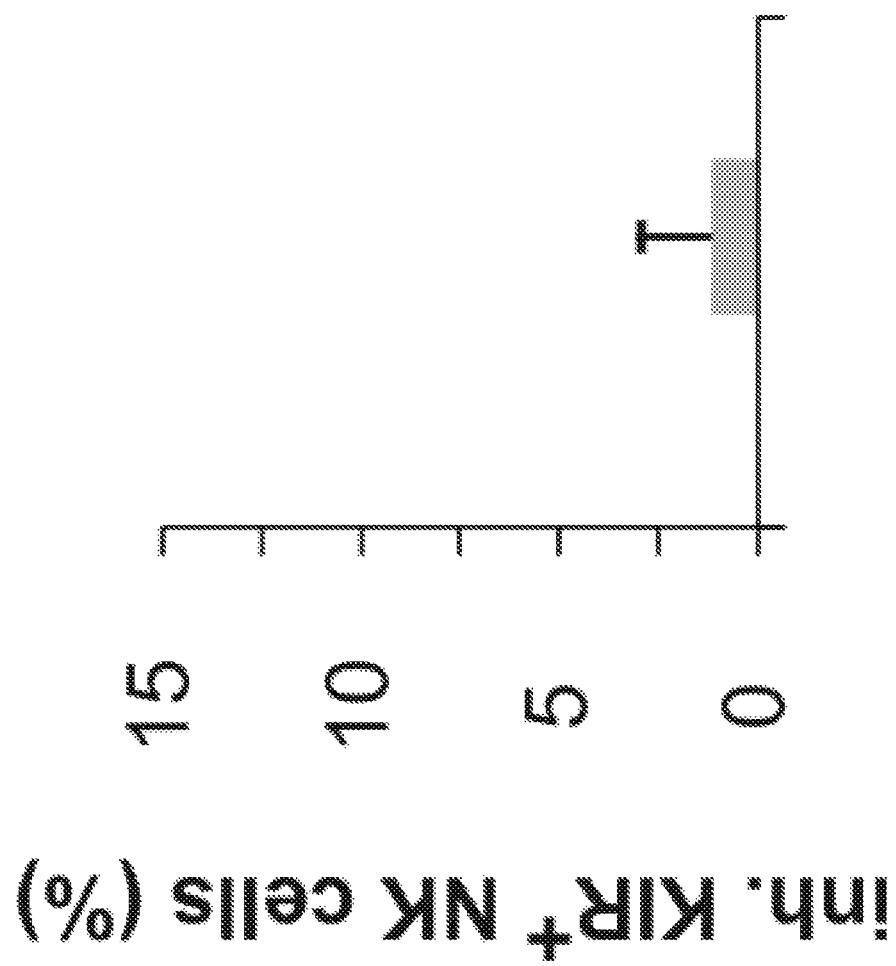
Figure 8E:
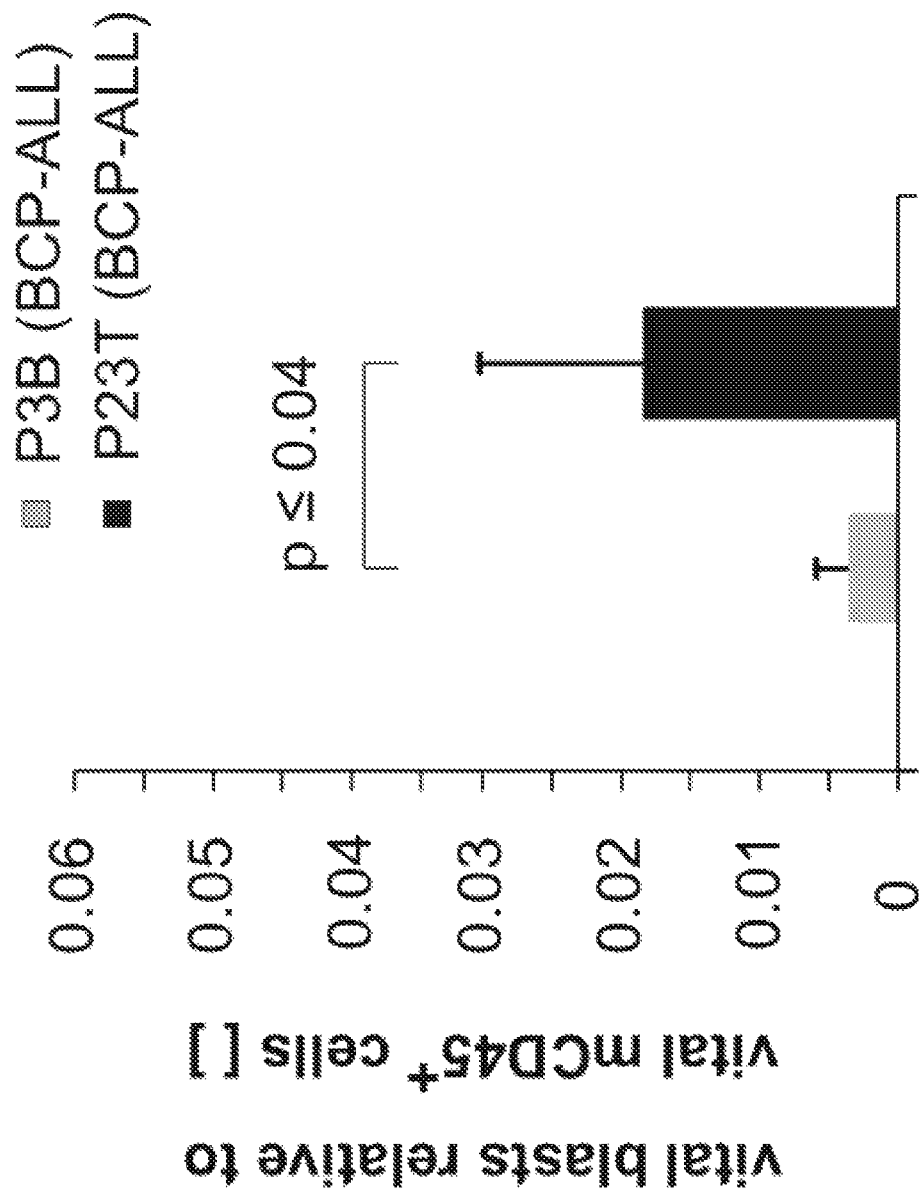
Figure 9B:
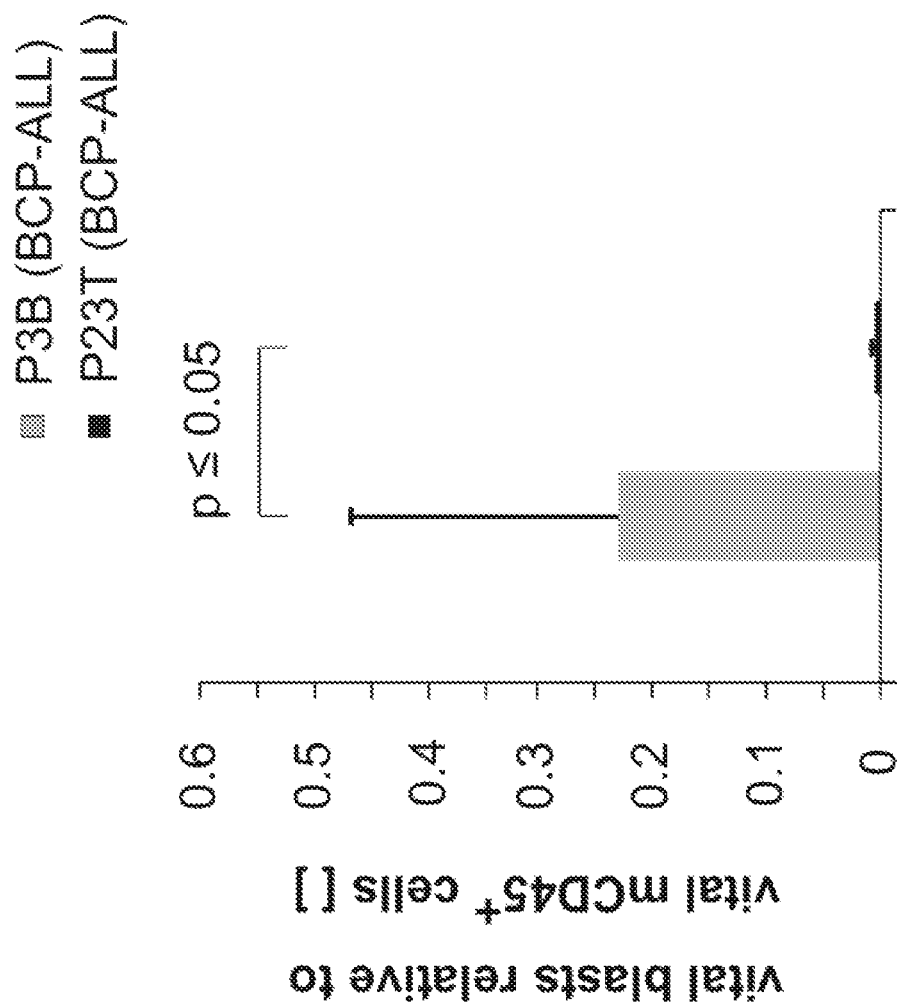

Since humans first reconstitute a large pool of immature KIR− NK cells early post transplantation (Pende et al., 2009; Nguyen et al., 2005; Vago et al., 2008), it was next investigated whether these NK cells might also exert effector functions against pediatric BCP-ALL. As KIR acquisition in NSG mice transplanted with human HSCs (huNSG) occurs only in a minor fraction of huNSG-derived NK cells (unpublished data), this NSG xenotransplantation model was chosen as a surrogate model for the generation of "pseudo-mature lytic NK cells" (Colucci et al., 2003) arising in the early post transplantation period in humans (FIG. 8A). The injection of a primary BCP-ALL specimen (P23T) into huNSG mice pre-stimulated with IL15/IL15Rα and poly I:C resulted in a substantial reduction of P23T tumor burden compared to control mice (FIG. 8B). Since these results suggested that huNSG-derived NK cells may in principle be functionally active, a pooled sample of equal numbers of two primary BCP-ALL samples (P3B and P23T) with different KIRL repertoires was next injected into huNSG mice (FIG. 8C). Applying the sequential gating strategy depicted in FIG. 9A and verifying that the huNSG-derived NK cells were indeed to a large extent negative for common inhibitory KIRs (FIG. 8D), the KIR-KIRL-mismatched sample P3B was found to be killed to a significantly greater extent than the matched sample P23T (FIG. 8E). Notably, the huNSG mice were deliberately euthanized 20 h post-injection of leukemia cells to exclude for T cell-mediated responses as a major cause of leukemia reduction. As the alloreactivity towards P3B and P23T was reversible in experiments performed with a different HSC donor (FIG. 9B), it was concluded that the alloreactivity towards P3B depicted in FIG. 8E was not a result of a P3B-intrinsic slower growth rate. Given that HLA class I, ICAM-1, NKG2D and DNAM-1 ligands (FIG. 1B) were expressed to a comparable extent by P3B and P23T, it was assumed that either KIR-KIRL interactions other than the one analyzed (KIR2DL1/S1/S4, KIR2DL2/S2/L3 and 3DL1) or modest differences, i.e., in the expression of NKG2DL, must have contributed to this phenomenon.

EXAMPLE 5

"Bridging" Therapy with 5-aza-Cytidine Supports NK Cell Alloreactivity Towards Pediatric BCP-ALL in the Early Post Transplantation Period Methods In Vivo Treatment of huNSG Mice with 5-Aza-Cytidine On Day 39 post-transplantation, huNSG mice were randomly assigned to treatment or control group and therapy with 5-aza-cytidine (0.025 mg/mouse/dose intraperitoneally, twice a week for a total of 4 weeks) or PBS as control was initiated. Four weeks later, $3 \times 10^6$ blasts were intravenously injected into 5-aza-cytidine or sham-treated animals. Twenty hours later, mice were sacrificed and subjected to analysis of NK cell phenotype and for quantification of leukemic burden.

Results

Figure 10A:
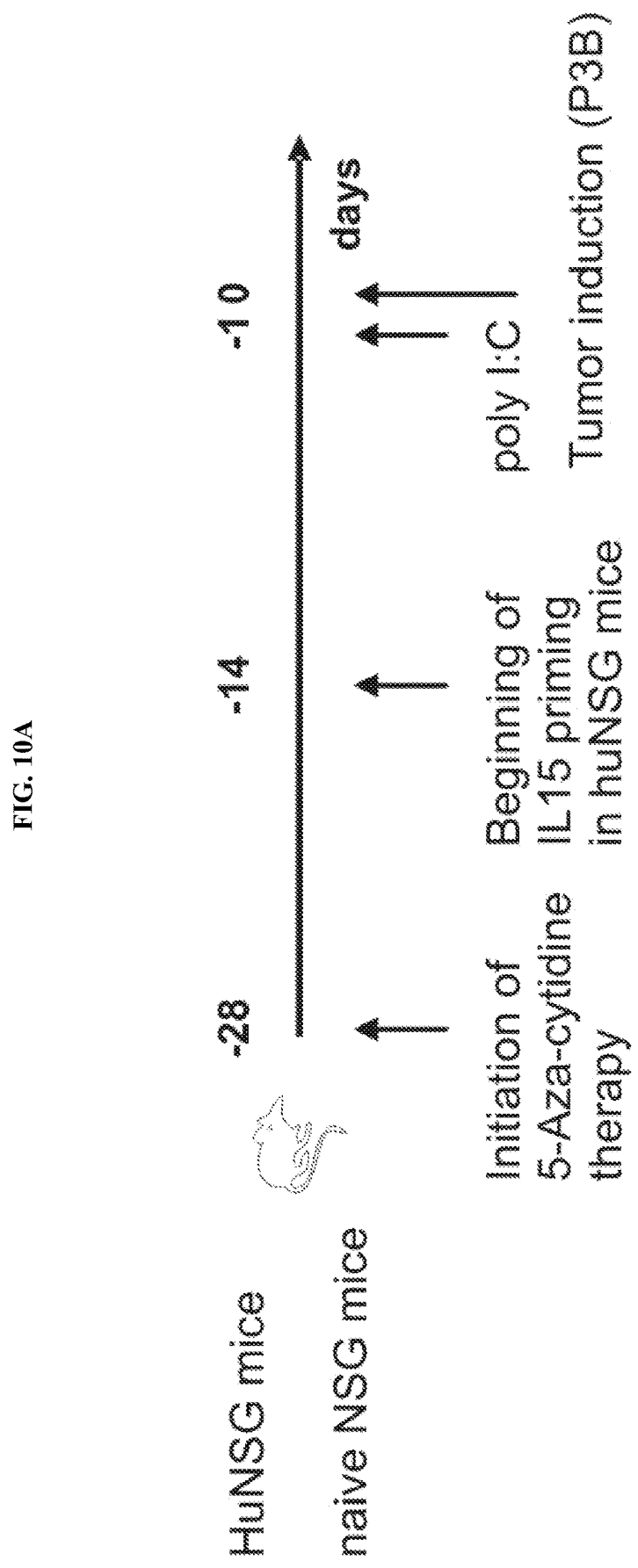
FIG. 10. "Bridging" therapy with 5-aza-cytidine supports NK cell alloreactivity towards pediatric BCP-ALL in the early post transplantation period. A: Experimental setup. B, C: Low-dose and long-term 5-aza-cytidine treatment does not exert statistically relevant BM cytotoxicity. The number of human (B) or murine (C) CD45$^+$ cells, normalized to total live cells, is given. Data depicted in part (B) were obtained in 5-aza-cytidine-treated huNSG mice. Data depicted in part (C) were obtained in 5-aza-cytidine-treated non-humanized control mice. D: Treatment with 5-aza-cytidine significantly reduces BCP-ALL tumor load in huNSG mice. E: Low-dose 5-aza-cytidine treatment regimen does not exert relevant direct cytotoxic effects on pediatric BCP-ALL. The number of vital blasts in the BM, normalized to murine CD45$^+$ cells in non-humanized control NSG mice, is given. F: Calculated effect size of in vivo 5-aza-cytidine treatment on pediatric BCP-ALL burden. "Exp. I and II" denote the two different experiments in huNSG mice, and "control I and II" denote the effect in the respective control groups. Data are representative of two independent experiments with a total of 11 huNSG mice and 14 control NSG mice.
Figure 10B:
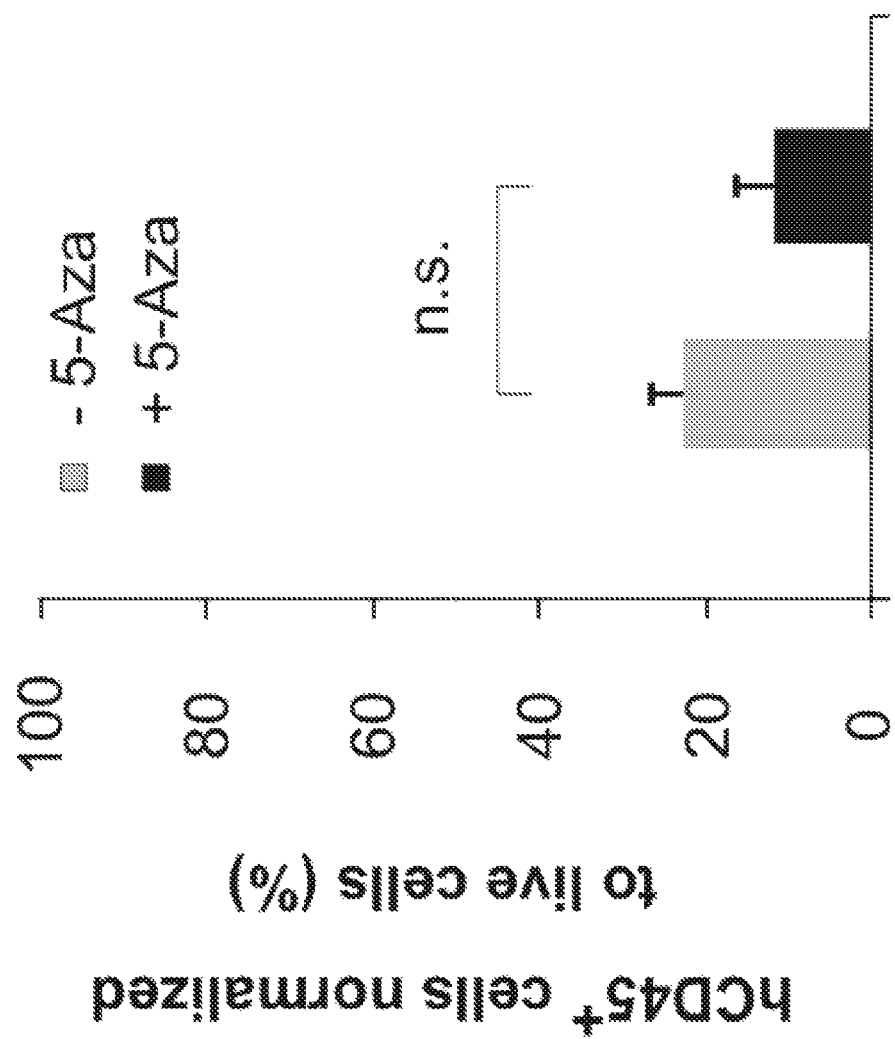
Figure 10C:
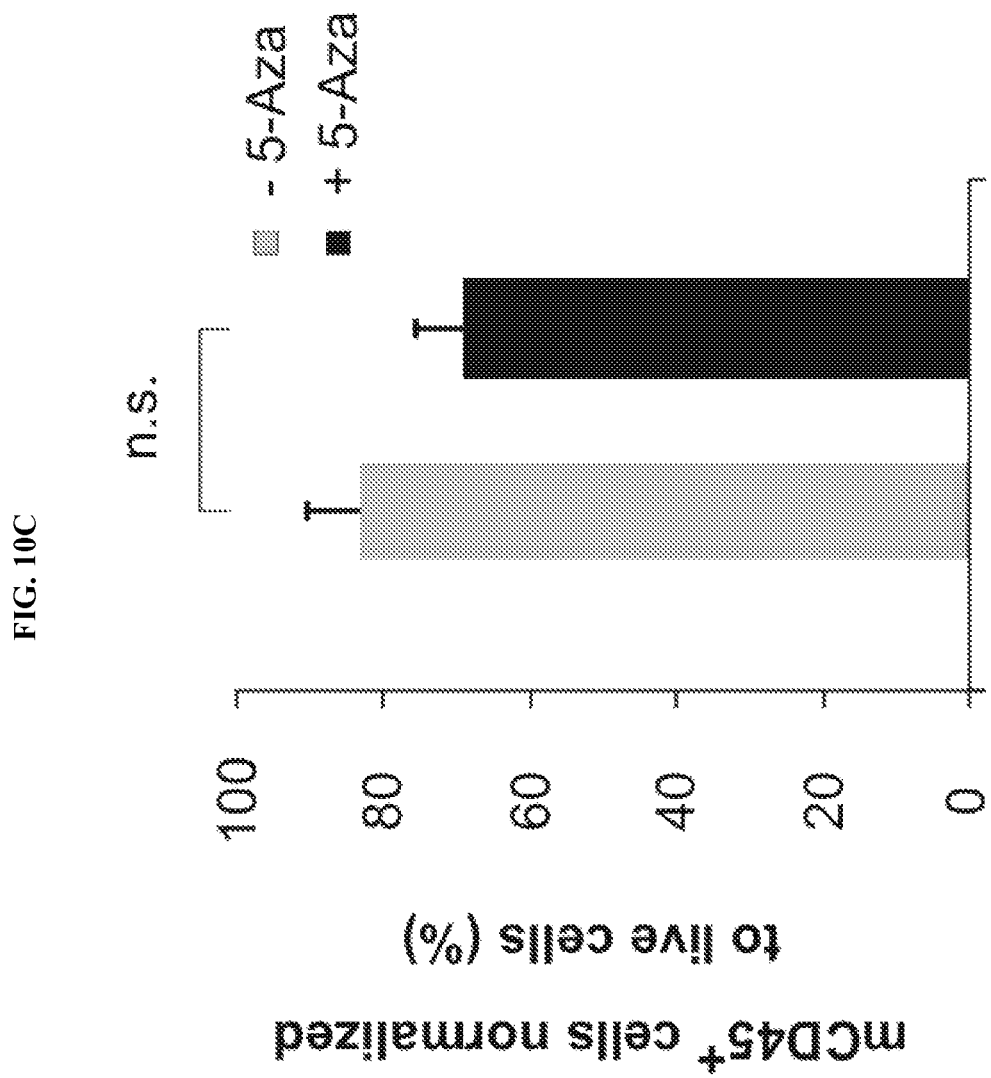
Figure 10D:
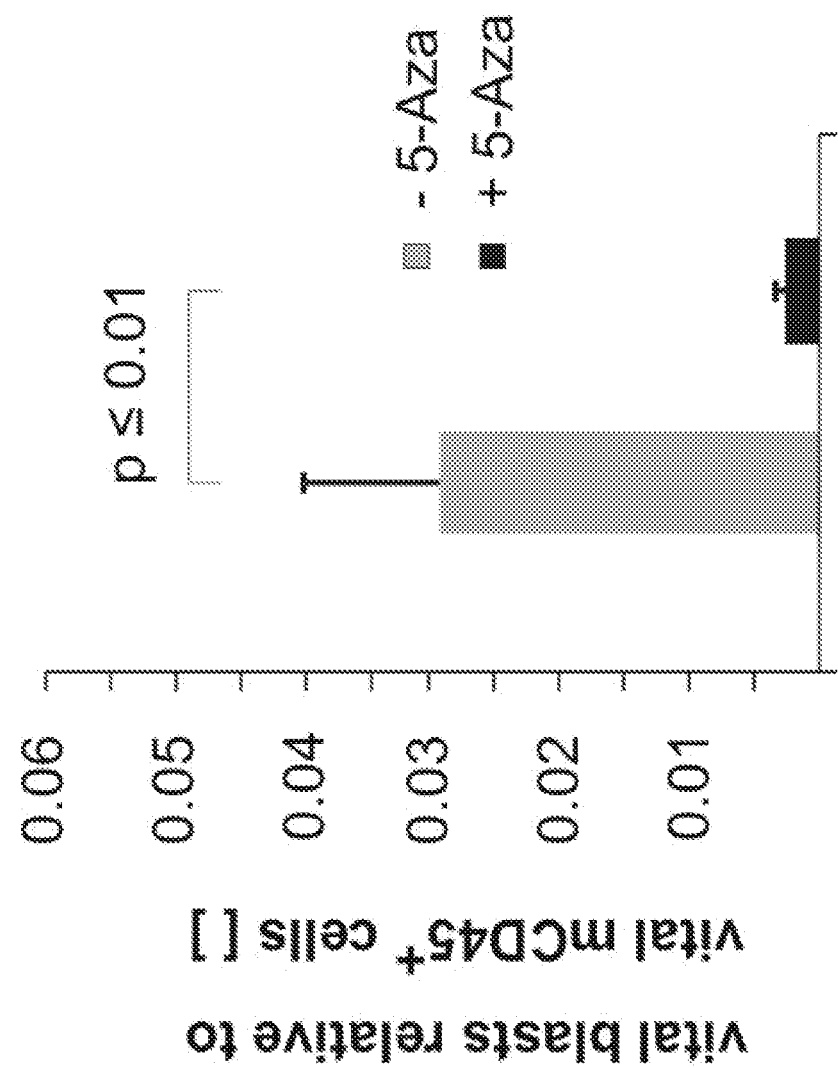
Figure 10E:
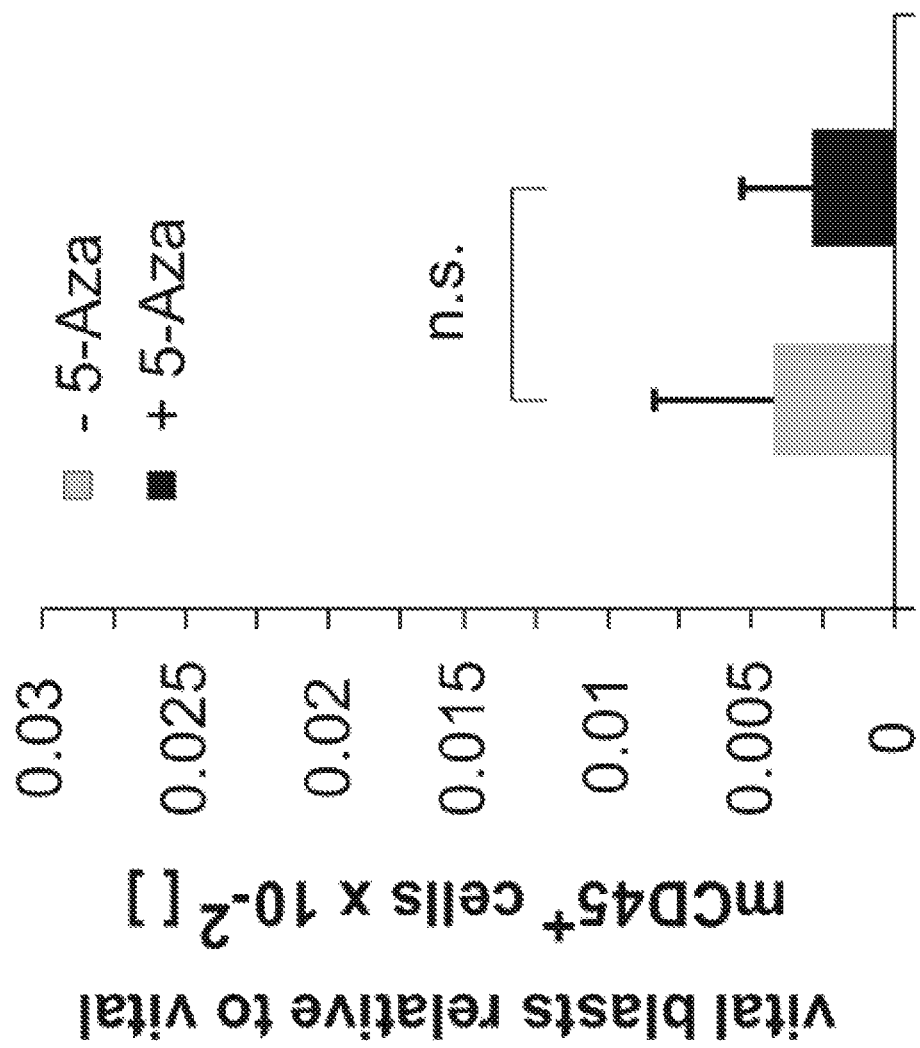
Figure 10F:
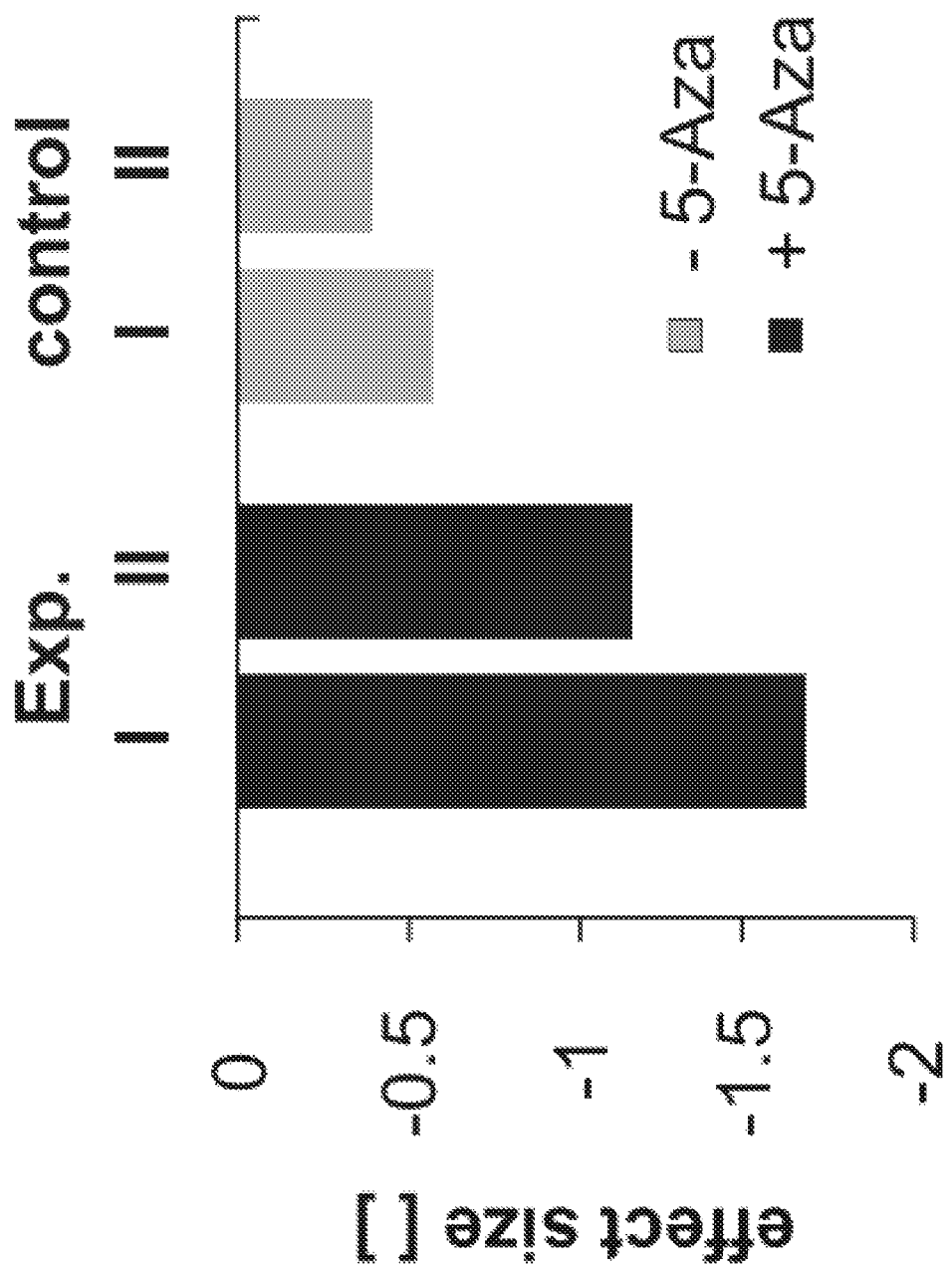

To elaborate the full potential of the immature NK cell pool arising early post-transplantation, existing in vitro data indicating that 5-aza-cytidine modulates NK cell function by inducing KIR promoter activity (Chan et al., 2003) and expression (Santourlidis et al., 2002) in a xenotransplantation model was recapitulated in the context of pediatric BCP-ALL disease. As the therapeutic efficacy of DNA methyltransferase (DNMT) inhibitors may range from the induction of DNA-demethylating effects at low doses to the induction of direct cytotoxic effects at higher doses, a low-dose treatment regimen was applied for an extended period to potentially enable long-term epigenetic modulation of NK cells (FIG. 10A). This treatment regimen resulted in a statistically insignificant reduction of both human and murine $CD45^+$ cells, reflecting to some extent a drug-induced BM cytotoxicity (FIG. 10B, C). Interestingly, contrary to previously published in vitro data reporting a 5-aza-cytidine induced functional inhibition of mature NK cells (Schmiedel et al., 2011), a clearly reduced BCP-ALL burden in 5-aza-cytidine-treated huNSG mice was observed (FIG. 10D, F). Notably, 5-aza-cytidine therapy had been stopped 3 days before the injection of leukemia and the half-life of the drug is described to be less than 4 h (Troetel et al., 1972). Together with data obtained in non-humanized controls (FIG. 10E), a drug-induced, direct cytotoxic effect that might have reduced the tumor load can, therefore, be largely excluded.

EXAMPLE 6

Low-Dose and Long-Term Exposure to 5-Aza-Cytidine Promotes NK Cell Ontogeny

Figure 11C:
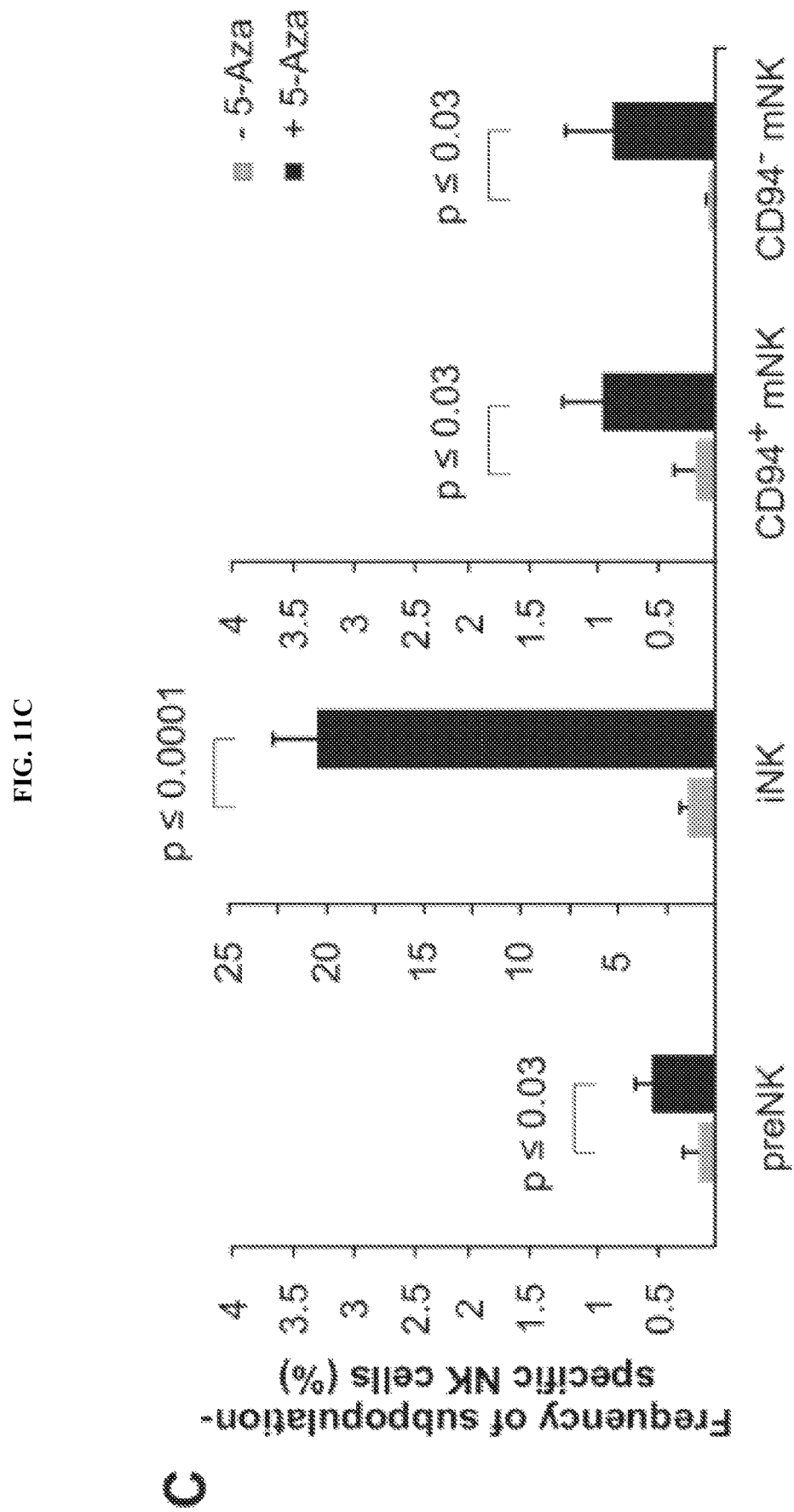
FIG. 11. Low-dose and long-term exposure to 5-aza-cytidine promotes NK cell ontogeny. A, B: 5-aza-cytidine does not significantly alter the expression of KIR2DL1 and 2DL2/3 (A) or other inhibitory or activating NK cell receptors (B) on BM-derived NK cells of huNSG mice. C: 5-aza-cytidine induces the expression of BM-residing NK cell precursors. Frequencies of the indicated NK cell subpopulations in the BM of 5-aza-cytidine-treated or control huNSG mice (as defined by Freud et al., 2006): preNK: CD34$^+$CD117$^+$, iNK: CD34$^-$CD117$^{low}$CD94$^-$, CD94$^+$ mNK cells: CD34$^-$CD117$^-$ CD94$^+$NKp46$^+$, CD94$^-$ mNK cells: CD34$^-$CD117$^-$CD94$^-$NKp46$^+$. Data represent two independent experiments with a total of 11 huNSG mice and 14 control NSG mice.

NK cell receptor analysis of huNSG mice revealed that 5-aza-cytidine did not significantly modulate the expression of either inhibitory (KIRs, NKG2A) or activating (NKp44, NKG2D) NK cell receptors at the low doses applied (FIGS. 11A, B). However, the analysis of NK cell subsets interestingly showed that 5-aza-cytidine-treated huNSG mice had clearly higher numbers of both immature ($CD34^+CD117^+$ and $CD34^-$ $CD117^{low}CD94^-$) NK cell precursors and mature ($CD34^-CD117^-CD94^+NKp46^+$ and $CD34^-CD117^-CD94^-NKp46^+$) NK cell subsets (Freud et al., 2006) (FIG. 11C), indicating that 5-aza-cytidine might have facilitated NK cell ontogeny itself.

EXAMPLE 7

Effect of Lirilumab on Levels of Inhibitory KIRs and Tumor Burden in huNSG Mice

Figure 13A:
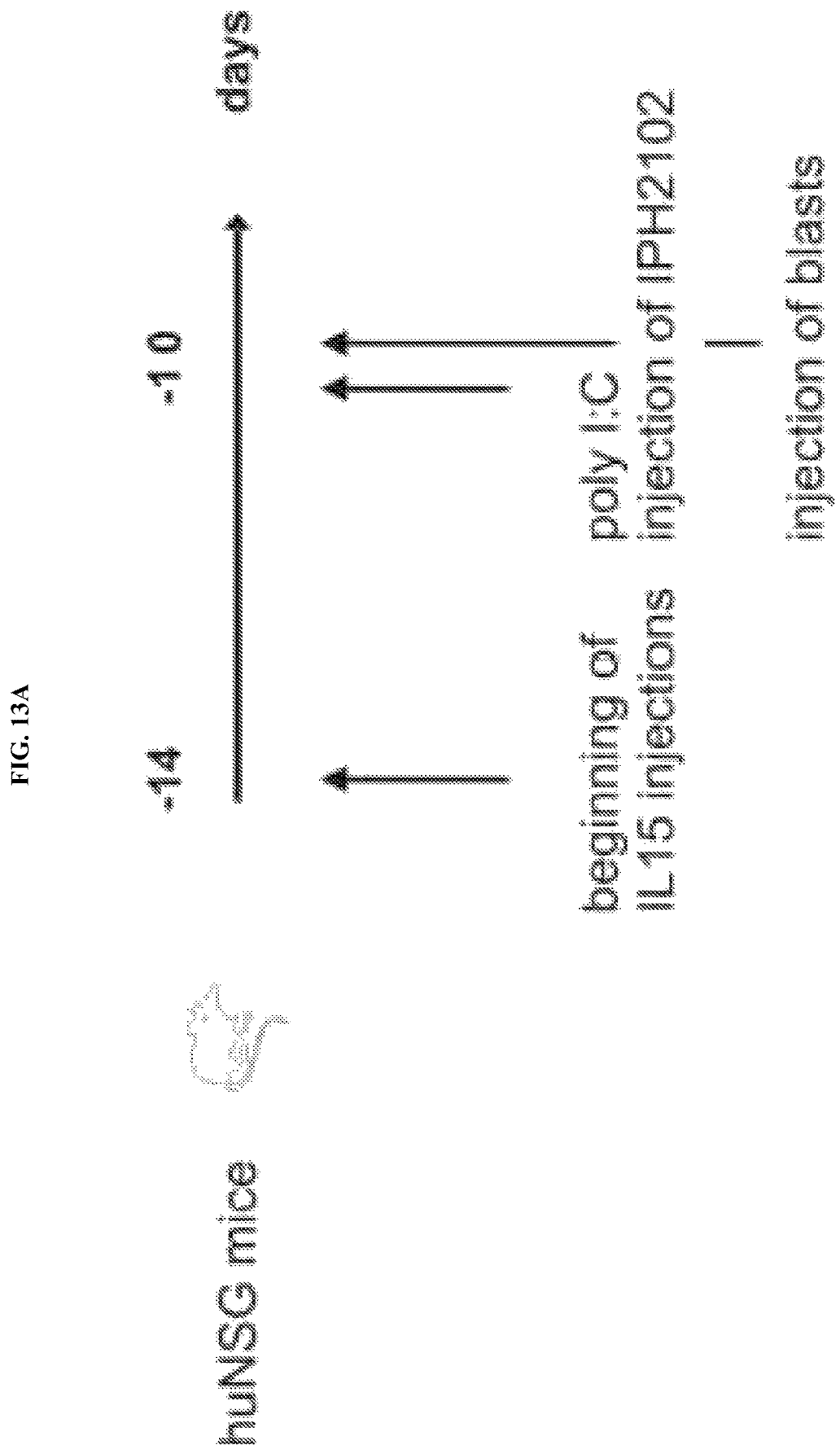
FIG. 13. Effect of lirilumab on inhibitory KIR expression and tumor burden in huNSG Mice. A: Experimental setup for lirilumab treatment of huNSG mice. B: Inhibitory KIR expression is negligible in lirilumab (IPH2102)-treated mice. C: Experimental setup for lirilumab treatment of adoptively NK cell transferred NSG mice. D: IPH2102 induces a significant reduction of tumor burden in the treated animal.

The experimental setup for treatment of huNSG mice with lirilumab (IPH2102) is shown in FIG. 13A. HuNSG mice were treated 14 days before the injection of leukemia cells with a complex of IL15/IL15Ra. One day prior to blasts injection, NK cells were additionally activated by intravenous injection of polyI:C and IPH2102. On the following day blasts were injected, and after 24 h the extent of tumor burden was quantified using 8-11 color flow cytometry. Lirilumab at a dose of 250 μg/mouse was shown to reduce the levels of inhibitory KIR expression to barely detectable levels (FIG. 13B).

Figure 13C:
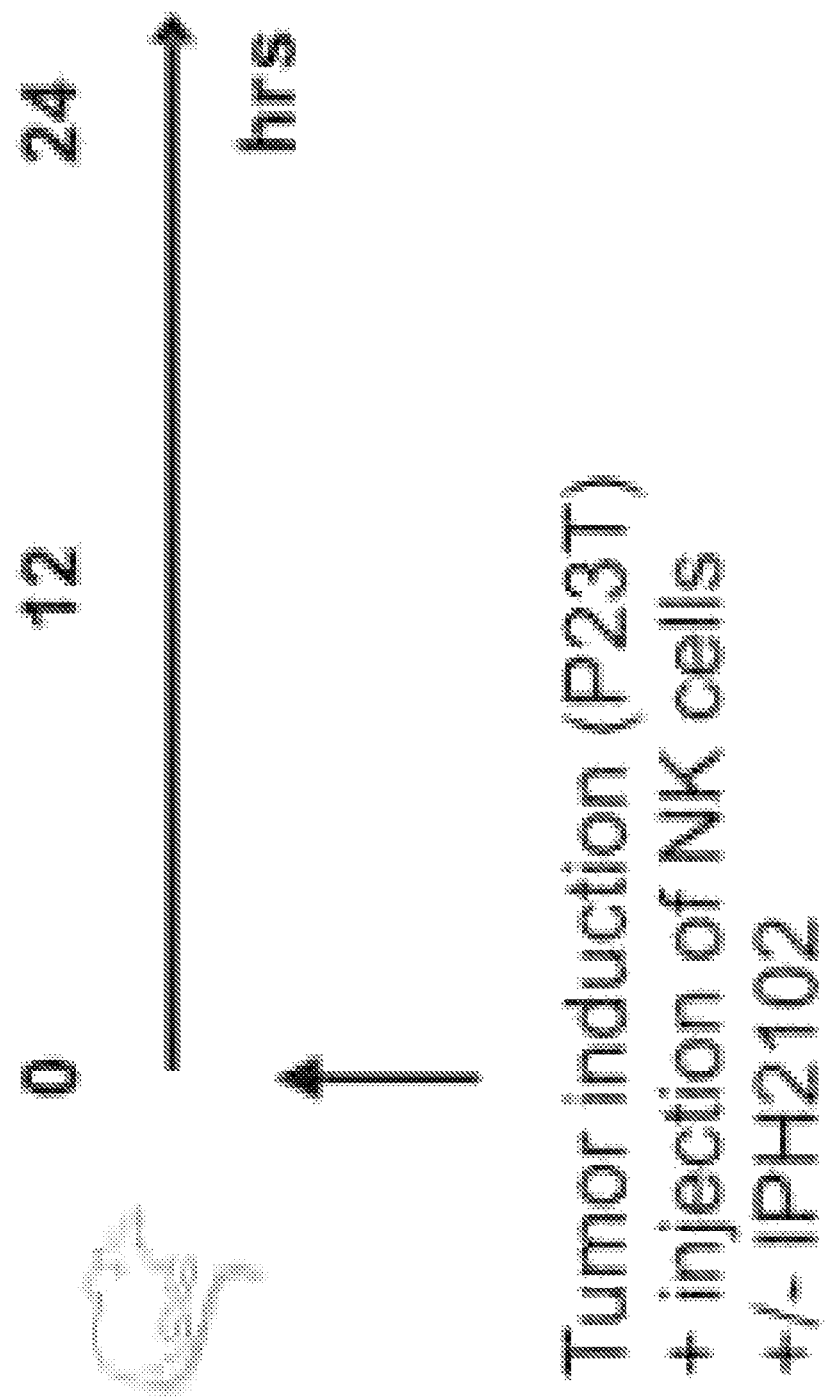

The experimental setup for investigating the effect of lirilumab (IPH2102) on pediatric BCP-ALL tumor burden in NSG mice pretreated by adoptively transferred KIR-KIRL-matched NK cells is shown in FIG. 13C. Naïve NSG mice were injected with blasts, followed by the injection of activated NK cells and subsequent intravenous injection of IPH2102 (2250 μg/mouse). Mice were euthanized after 24 h to quantify tumor burden. Notably, the NK cell donor and the respective BCP-ALL sample P23T display a KIR-KIRL match constellation. As shown in FIG. 13D, lirilumab induces a significant reduction of tumor burden in treated mice. Data depicted in FIGS. 13B and D represent preliminary data performed in a small number of mice. The data provided in Examples 1-4 support the concept that NK cell immune-therapy, ideally performed with KIR-KIRL-mismatched donors, should have a role in the treatment of pediatric BCP-ALL disease. The present preliminary data demonstrate that therapy with an anti-inhibitory KIR Ab such as lirilumab offers a valuable, additional therapeutic option to selected BCP-ALL patients who lack a KIR-KIRL-mismatched donor.

EXAMPLE 8

Effect of Lirilumab on Adoptive Transfer of NK Cells into huNSG Mice

Experiments are conducted to evaluate the effect of lirilumab on five different KIR-KIRL-matched donor/patient constellations in the context of pediatric BCP-ALL. Preparative arrangements (donor/patient HLA high resolution typing, expansion of parental NK cells and characterization of the respective NK cell receptor repertoire, characterization of NK cell receptor ligand repertoire on leukemic cells) are made prior to in vivo experiments that include the adoptive transfer of cytokine-matured donor-derived NK cells (described below) or experiments in huNSG mice that represent the early post-transplantation period (see Example 9).

Figure 14:
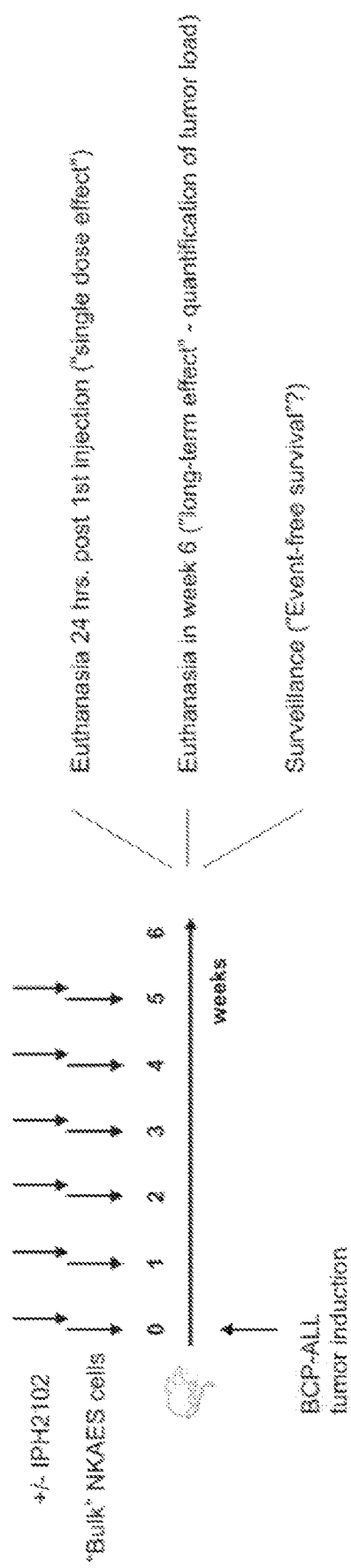
FIG. 14. Effect of lirilumab on the efficacy of adoptive transfer of NK cells into huNSG mice for treating BCP-ALL. The experimental setup for testing the effect of lirilumab on adoptive transfer of cytokine-matured, donor-derived NK cells in huNSG mice is depicted.

The experimental setup for the adoptive NK cell transfer experiments in huNSG mice, designed to be comparable to studies in humans, is shown in FIG. 14. Expanded NK cells are injected once a week for 5 weeks into NSG mice that are co-injected with patient-specific leukemia. Lirilumab is injected intravenously into half of the mice at a dose of 250 μg/mouse on the day following injection with the NK and leukemia cells. Depending on the pre-defined endpoint of analysis, three different readout modalities exist that include the characterization of (a) the single dose effect, (b) the long-term effect of multiple NK/IPH2102 injections, and (c) the documentation of a Kaplan-Maier survival curve. The data show how lirilumab affects the efficacy of adoptive NK cell transfer in reducing the tumor burden.

EXAMPLE 9

Effect of Lirilumab on Tumor Burden in Humanized Neonatal NSG Mice

Figure 15:
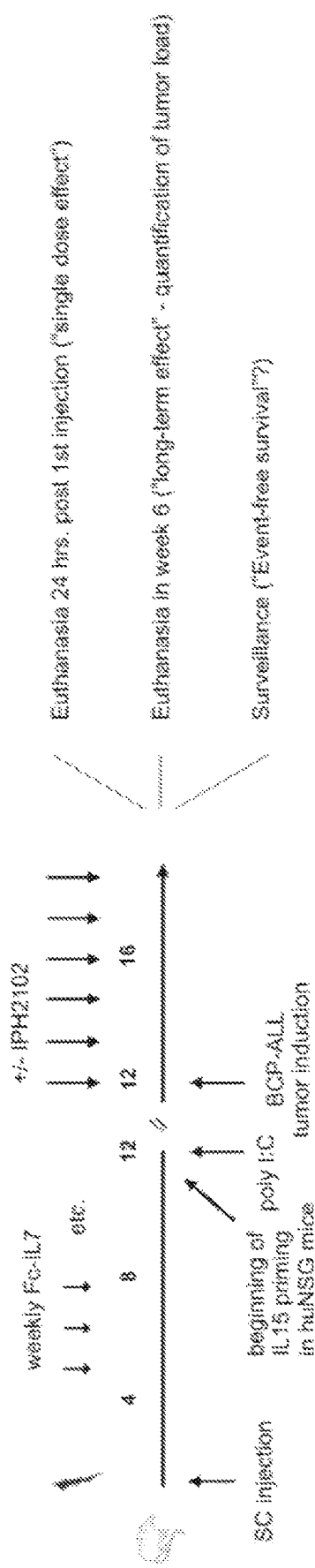
FIG. 15. Effect of lirilumab on tumor burden in humanized neonatal NSG mice. The setup for testing the effect of lirilumab on BCP-ALL tumor burden in humanized NSG mice that represent the early post-translation period is depicted.

The setup for the experiments in humanized NSG mice is depicted in FIG. 15. Donor-derived stem cells are used to humanize sublethally irradiated neonatal NSG mice. All mice are supported by weekly Fc-IL7 injections at the earliest time that is technically feasible (around week 5). KIR expression and NK cell functionality are induced with injections of IL15/IL15Rα complex and the Toll-like receptor agonist, poly I:C. In week 12, huNSG mice receive patient-specific leukemia and repetitive injections of lirilumab at a dose of 250 µg/mouse. As readout, the extent of GvL effects of early arising immature NK cells in the presence or absence of lirilumab is quantified. These data, together with the data obtained in Example 8, demonstrate the clinical relevance that anti-KIR therapy has for KIR-KIRL matched donor/patient pairs in the setting of pediatric BCP-ALL disease.

SEQUENCE LISTING SUMMARY

| SEQ ID NO: | Description |
| --- | --- |
| 1 | $V_H$ amino acid sequence of lirilumab |
| 2 | $V_L$ amino acid sequence of lirilumab |
| 3 | Amino acid sequence of 1-7F9 H chain |
| 4 | Amino acid sequence of lirilumab H chain |
| 5 | Amino acid sequence of lirilumab L chain |
| 6 | H chain CDR1 sequence of lirilumab |
| 7 | H chain CDR2 sequence of lirilumab |
| 8 | H chain CDR3 sequence of lirilumab |
| 9 | L chain CDR1 sequence of lirilumab |
| 10 | L chain CDR2 sequence of lirilumab |
| 11 | L chain CDR1 sequence of lirilumab |

REFERENCES

Altschul S F, Gish W, Miller W, et al. (1990) Basic local alignment search tool. *J Mol Biol* 215(3):403-10.

Altschul S F, Madden T L, Schäffer A A, et al. (1997) Gapped BLAST and PSI-BLAST: a new generation of protein database search programs. *Nucl Acids Res* 25(17): 3389-402.

Alves L G, Rajalingam R, Canavez F (2009) A novel real-time PCR method for KIR genotyping. *Tissue Antigens* 73(2):188-91.

André M C, Erbacher A, Gille C, et al. (2010) Long-term human CD34+ stem cell-engrafted nonobese diabetic/SCID/IL2Rγ$^{null}$ mice show impaired CD8+ T cell maintenance and a functional arrest of immature NK cells. *J Immunol* 185(5):2710-20.

Angal S, King D J, Bodmer M W, et al. (1993) A single amino acid substitution abolishes the heterogeneity of chimeric mouse/human (IgG4) antibody. *Mol Immunol* 30(1):105-8.

Beiboer S H, Reurs A, Roovers R C, et al. (2000) Guided selection of a pan carcinoma specific antibody reveals similar binding characteristics yet structural divergence between the original murine antibody and its human equivalent. *J Mol Biol* 296(3):833-49.

Benson D M Jr., Hofmeister C C, Padmanabhan S et al. (2012) A phase 1 trial of the anti-KIR antibody IPH2101 in patients with relapsed/refractory multiple myeloma. *Blood* 120(22):4324-33.

Campbell K S and Purdy A K (2011) Structure/function of human killer cell immunoglobulin-like receptors: lessons from polymorphisms, evolution, crystal structures and mutations. *Immunol* 132(3):315-25.

Chan H W, Kurago Z B, Stewart C A, et al. (2003) DNA methylation maintains allele-specific KIR gene expression in human natural killer cells. *J Exp Med* 197(2):245-55.

Colucci F, Acligiuri M A, Di Santo J P (2003) What does it take to make an natural killer cell? *Nat Rev Immunol* 3(5):413-25.

Colucci F, Samson S I, DeKoter R P, et al. (2001) Differential requirement for the transcription factor PU.1 in the generation of natural killer cells versus B and T cells. *Blood* 97(9):2625-32.

Cooley S, Weisdorf D J, Guethlein L A, et al. (2010) Donor selection for natural killer cell receptor genes leads to superior survival after unrelated transplantation for acute myelogenous leukemia. *Blood* 116(14):2411-9.

Curik N, Burda P, Vargova K, et al. (2012) 5-azacitidine in aggressive myelodysplastic syndromes regulates chromatin structure at PU.1 gene and cell differentiation capacity. *Leukemia* 26(8):1804-11.

de Lima M, Giralt S, Thall P F, et al. (2010) Maintenance therapy with low-dose azacitidine after allogeneic hematopoietic stem cell transplantation for recurrent acute myelogenous leukemia or myelodysplastic syndrome: a dose and schedule finding study. *Cancer* 116(23):5420-31.

Ditzel H J, Itoh K, Burton D R (1996) Determinants of polyreactivity in a large panel of recombinant human antibodies from HIV-1 infection. *J Immunol* 157(2):739-49.

Farag S S, Fehniger T A, Ruggeri L, et al. (2002) Natural killer cell receptors: new biology and insights into the graft-versus-leukemia effect. *Blood* 100(6):1935-47.

Fernandez N C, Treiner E, Vance R E, et al. (2005) A subset of natural killer cells achieves self-tolerance without expressing inhibitory receptors specific for self-MHC molecules. *Blood* 105(11):4416-23.

Ferrini S, Cambiaggi A, Meazza R, et al. (1994) T cell clones expressing the natural killer cell-related p58 receptor molecule display heterogeneity in phenotypic properties and p58 function. *Eur J Immunol* 24(10):2294-8.

Feuchtinger T, Pfeiffer M, Pfaffle A, et al. (2009) Cytolytic activity of NK cell clones against acute childhood precursor-B-cell leukaemia is influenced by HLA class I expression on blasts and the differential KIR phenotype of NK clones. *Bone Marrow Transplant* 43(11):875-81.

Freud A G, Yokohama A, Becknell B, et al. (2006) Evidence for discrete stages of human natural killer cell differentiation in vivo. *J Exp Med* 203(4):1033-43.

Frikeche J, Clavert A, Delaunay J, et al. (2011) Impact of the hypomethylating agent 5-azacytidine on dendritic cells function. *Exp Hematol* 39(11):1056-63.

Fujisaki H, Kakuda H, Shimasaki N, et al. (2009) Expansion of highly cytotoxic human natural killer cells for cancer cell therapy. *Cancer Res* 69(9):4010-7.

Gao X N, Lin J, Wang L L, Yu L (2009) Demethylating treatment suppresses natural killer cell cytolytic activity. *Mol Immunol* 46(10):2064-70.

Hagemann S, Heil O, Lyko F, Brueckner B (2011) Azacytidine and decitabine induce gene-specific and non-random DNA demethylation in human cancer cell lines. *PLoS One* 6(3):e17388.

Hollinger P and Hudson P J (2005) Engineered antibody fragments and the rise of single domains. *Nature Biotech* 23(9):1126-36.

Howlader N, Noone A M, Krapcho M, et al. (eds) (2015) SEER Cancer Statistics Review, 1975-2012, National Cancer Institute: Bethesda, Md., seer.cancer.gov/csr/1975_2012/, based on November 2014 SEER data submission, posted to the SEER web site, April 2015 (last accessed Oct. 27, 2015).

Hunger S P, Lu X, Devidas M, et al. (2012) Improved survival for children and adolescents with acute lymphoblastic leukemia between 1990 and 2005: a report from the Children's Oncology Group. *J Clin Oncol* 30(14):1663-9.

Huntington N D, Legrand N, Alves N L, et al. (2009) IL-15 trans-presentation promotes human NK cell development and differentiation in vivo. *J Exp Med* 206:25-34.

Jabbour E, Giralt S, Kantarjian H, et al. (2009) Low-dose azacitidine after allogeneic stem cell transplantation for acute leukemia. *Cancer* 115(9):1899-905.

Kim S, Poursine-Laurent J, Truscott S M, et al. (2005) Licensing of natural killer cells by host major histocompatibility complex class I molecules. *Nature* 436(7051):709-13.

Kübler A, Woiterski J, Witte K E, et al. (2014). Both mature KIR+ and immature KIR- NK cells control pediatric acute B cell precursor leukemia in NOD.Cg-Prkdc$^{scid}$ IL2rg$^{tmWjl}$/Sz mice. *Blood* 124(26):3914-23.

Leung W, Iyengar R, Turner V, et al. (2004) Determinants of antileukemia effects of allogeneic NK cells. *J Immunol* 172(1):644-50.

Lübbert M, Bertz H, Wäsch R, et al. (2010) Efficacy of a 3-day, low-dose treatment with 5-azacytidine followed by donor lymphocyte infusions in older patients with acute myeloid leukemia or chronic myelomonocytic leukemia relapsed after allografting. *Bone Marrow Transplant* 45(4):627-32.

Melero I, Salmerón A, Balboa M A, et al. (1994) Tyrosine kinase-dependent activation of human NK cell functions upon stimulation through a 58-kDa surface antigen selectively expressed on discrete subsets of NK cells and T lymphocytes. *J Immunol* 152(4):1662-73.

Mengarelli A, Zarcone D, Caruso R, et al. (2001) Adhesion molecule expression, clinical features and therapy outcome in childhood acute lymphoblastic leukemia. *Leuk Lymphoma* 40(5-6):625-30.

Miller J S, Soignier Y, Panoskaltsis-Mortari A, et al. (2005) Successful adoptive transfer and in vivo expansion of human haploidentical NK cells in patients with cancer. *Blood* 105(8):3051-7.

Moretta A, Bottino C, Pende D, et al. (1990) Identification of four subsets of human CD3-CD16+ natural killer (NK) cells by the expression of clonally distributed functional surface molecules: correlation between subset assignment of NK clones and ability to mediate specific alloantigen recognition. *J Exp Med* 172(6):1589-98.

Moretta L, Locatelli F, Pende D, et al. (2011) Killer Ig-like receptor-mediated control of natural killer cell alloreactivity in haploidentical hematopoietic stem cell transplantation. *Blood* 117(3):764-71.

Nguyen S, Dhedin N, Vernant J P, et al. (2005) NK-cell reconstitution after haploidentical hematopoietic stem-cell transplantations: immaturity of NK cells and inhibitory effect of NKG2A override GvL effect. *Blood* 105(10):4135-42.

Olafsen T and Wu A M (2010) Antibody vectors for imaging. *Semin Nucl Med* 40(3):167-81.

Orr M T, Murphy W J, Lanier L L (2011) 'Unlicensed" natural killer cells dominate the response to cytomegalovirus infection. *Nat Immunol* 11(4):321-7.

PCT Publication No. WO 2005/003168, published Jan. 13, 2005 by Novo Nordisk A/S et al.

PCT Publication No. WO 2006/003179, published Jan. 1, 2006 by Novo Nordisk A/S et al.

PCT Publication No. WO 2008/084106, published Jul. 17, 2008 by Novo Nordisk A/S.

Pende D, Marcenaro S, Falco M, et al. (2009) Anti-leukemia activity of alloreactive NK cells in KIR ligand-mismatched haploidentical HSCT for pediatric patients: evaluation of the functional role of activating KIR and redefinition of inhibitory KIR specificity. *Blood* 113(13):3119-29.

Pende D, Spaggiari G M, Marcenaro S, et al. (2005) Analysis of the receptor-ligand interactions in the natural killer-mediated lysis of freshly isolated myeloid or lymphoblastic leukemias: evidence for the involvement of the Poliovirus receptor (CD155) and Nectin-2 (CD112). *Blood* 105(5):2066-73.

Pfeiffer M, Schumm M, Feuchtinger T, et al. (2007) Intensity of HLA class I expression and KIR-mismatch determine NK-cell mediated lysis of leukaemic blasts from children with acute lymphatic leukaemia. *Br J Haematol* 138:97-100.

Pfeiffer M M, Schumm M, Müller I, et al. (2012) IL-15-stimulated CD3/CD19-depleted stem-cell boosts in relapsed pediatric patients after haploidentical SCT. *Leukemia* 26(11):2435-9.

Pui C H, Campana D, Pei D, et al. (2009) Treating childhood acute lymphoblastic leukemia without cranial irradiation. *N Engl J Med* 360(26):2730-41.

Rubnitz J E, Inaba H, Ribeiro R C, et al. (2010) NKAML: a pilot study to determine the safety and feasibility of haploidentical natural killer cell transplantation in childhood acute myeloid leukemia. *J Clin Oncol* 28(6):955-9.

Rudikoff S, Giusti A M, Cook W D, et al. (1982) Single amino acid substitution altering antigen-binding specificity. *Proc Natl Acad Sci USA* 79(6):1979-83.

Ruggeri L, Capanni M, Casucci M, et al. (1999) Role of natural killer cell alloreactivity in HLA-mismatched hematopoietic stem cell transplantation. *Blood* 94(1):333-9.

Ruggeri L, Capanni M, Urbani E, et al. (2002) Effectiveness of donor natural killer cell alloreactivity in mismatched hematopoietic transplants. *Science* 295(5562):2097-100.

Santourlidis S, Trompeter H I, Weinhold S, et al. (2002) Crucial role of DNA methylation in determination of clonally distributed killer cell Ig-like receptor expression patterns in NK cells. *J Immunol* 169(8):4253-61.

Schmiedel B J, Arélin V, Gruenebach F, et al. (2011) Azacytidine impairs NK cell reactivity while decitabine augments NK cell responsiveness toward stimulation. *Int J Cancer* 128(12):2911-22.

Shin J S, Shin E C, Kim J, et al. (1999) Monoclonal antibodies with various reactivity to p58 killer inhibitory receptors. *Hybridoma* 18(6):521-7.

Spaggiari G M, Contini P, Carosio R, et al. (2002a) Soluble HLA class I molecules induce natural killer cell apoptosis through the engagement of CD8: evidence for a negative regulation exerted by members of the inhibitory receptor superfamily. *Blood* 99(5):1706-14.

Spaggiari G M, Contini P, Dondero A, et al. (2002b) Soluble HLA class I induces NK cell apoptosis upon the engagement of killer-activating HLA class I receptors through FasL-Fas interaction. *Blood* 100(12):4098-107.

Statement on Nonproprietary Name Adopted by the USAN Council for lirilumab, Oct. 31, 2012, download.ama-assn.org/resources/doc/usan/x-pub/lirilumab.pdf (last accessed Oct. 27, 2015).

Strowig T, Chijioke O, Carrega P, et al. (2010) Human NK cells of mice with reconstituted human immune system components require pre-activation to acquire functional competence. *Blood* 116(20):4158-67.

Troetel W M, Weiss A J, Stambaugh J E, et al. (1972) Absorption, distribution, and excretion of 5-azacytidine (NSC-102816) in man. *Cancer Chemother Rep* 56(3):405-11.

Vago L, Forno B, Sormani M P, et al. (2008) Temporal, quantitative, and functional characteristics of single-KIR-positive alloreactive natural killer cell recovery account for impaired graft-versus-leukemia activity after haploidentical hematopoietic stem cell transplantation. *Blood* 112(8):3488-99.

Vey N, Bourhis J H, Boissel N, et al. (2012) A phase 1 trial of the anti-inhibitory KIR mAb IPH2101 for AML in complete remission. Blood 120(22):4317-23.

Vilches C, Castaño J, Gómez-Lozano N, Estefania E (2007) Facilitation of KIR genotyping by a PCR-SSP method that amplifies short DNA fragments. *Tissue Antigens* 70(5): 415-22.

Watzl C, Peterson M, Long E O et al. (2000) Homogenous expression of killer cell immunoglobulin-like receptors (KIR) on polyclonal natural killer cells detected by a monoclonal antibody to KIR2D. *Tissue Antigens* 56(3): 240-7.

Welte S A, Sinzger C, Lutz S Z, et al. (2003) Selective intracellular retention of virally induced NKG2D ligands by the human cytomegalovirus UL16 glykoprotein. *Eur J Immunol* 33(1):194-203.

Woiterski J, Ebinger M, Witte K E, et al. (2013) Engraftment of low numbers of pediatric acute lymphoid and myeloid leukemias into NOD/SCID/IL2Rγnull mice reflects individual leukemogenecity and highly correlates with clinical outcome. *Int J Cancer* 133(7):1547-56.

Yawata M, Yawata N, Draghi M, et al. (2008) MHC class I-specific inhibitory receptors and their ligands structure diverse human NK-cell repertoires toward a balance of missing self-response. *Blood* 112(6):2369-80.

What is claimed is:

1. A method for treating a pediatric subject afflicted with acute B cell precursor leukemia (BCP-ALL) comprising administering to the subject as monotherapy an anti-killer cell immunoglobulin-like receptor (KIR) monoclonal antibody or an antigen-binding portion thereof, wherein the monoclonal antibody and the antigen-binding portion thereof:
   (a) bind specifically to KIR2DL1 and/or KIR2DL2/3 and blocks KIR2DL1 and/or KIR2DL2/3 activity, thereby potentiating NK cell lytic activity; and
   (b) comprise a heavy chain CDR1 domain comprising consecutively linked amino acids having the sequence set forth in SEQ ID NO:6; a heavy chain CDR2 domain comprising consecutively linked amino acids having the sequence set forth in SEQ ID NO:7; a heavy chain CDR3 domain comprising consecutively linked amino acids having the sequence set forth in SEQ ID NO:8; a light chain CDR1 domain comprising consecutively linked amino acids having the sequence set forth in SEQ ID NO:9; a light chain CDR2 domain comprising consecutively linked amino acids having the sequence set forth in SEQ ID NO:10; and a light chain CDR3 domain comprising consecutively linked amino acids having the sequence set forth in SEQ ID NO:11.

2. The method of claim 1, wherein the anti-KIR antibody or antigen-binding portion thereof:
   (a) is cross-reactive with and blocks the activity of KIR2DL1 and KIR2DL2/3 but does not bind to KIR2DS4; or
   (b) is cross-reactive with and blocks the activity of KIR2DL1 and KIR2DL2/3, does not bind to KIR2DS4, and further does not bind to KIR2DS3.

3. The method of claim 1, wherein the anti-KIR antibody or antigen-binding portion thereof binds to:
   (a) KIR2DL1 with a dissociation constant ($K_D$) of $4.5 \times 10^{-10}$ M; and/or
   (b) KIR2DL2/3 with a dissociation constant ($K_D$) of $2.5 \times 10^{-11}$ M.

4. The method of claim 1, wherein the anti-KIR antibody or antigen-binding portion thereof is a chimeric, humanized or human antibody, or an antigen-binding portion of any of said chimeric, humanized or human antibody.

5. The method of claim 1, wherein the anti-KIR antibody or antigen-binding portion thereof comprises a heavy chain constant region which is of a human IgG4 isotype.

6. The method of claim 5, wherein the anti-KIR antibody or antigen-binding portion thereof comprises a heavy chain constant region which is of a human IgG4 isotype containing an S241P mutation, wherein the serine at position 241 is numbered according to the Kabat system.

7. The method of claim 1, wherein the anti-KIR antibody or antigen-binding portion thereof comprises a human heavy chain comprising consecutively linked amino acids having the sequence set forth in SEQ ID NO:4 and a human light chain comprising consecutively linked amino acids having the sequence set forth in SEQ ID NO:5.

8. The method of claim 1, wherein the anti-KIR antibody or antigen-binding portion thereof is lirilumab or an antigen-binding portion thereof.

9. The method of claim 1, wherein the anti-KIR antibody or antigen-binding portion thereof is administered at a dose ranging from 0.01 to 10 mg/kg body weight once every 2, 3 or 4 weeks.

10. The method of claim 9, wherein the anti-KIR antibody or antigen-binding portion thereof is administered at a dose ranging from 0.1 to 1 mg/kg body weight once every 2, 3 or 4 weeks.

11. The method of claim 1, wherein the anti-KIR antibody is formulated for intravenous administration.

12. The method of claim 1, wherein the KIR on NK cells to which the monoclonal antibody or antigen-binding portion thereof binds is a KIR that matches a KIR ligand (KIRL) on the patient's BCP-ALL cells.

13. The method of claim 12, wherein the subject is a pediatric patient who is under 1 year of age.

14. A kit for treating a subject afflicted with acute pediatric BCP-ALL, the kit comprising:
   (a) a dosage ranging from 0.01 to 10 mg/kg body weight of an anti-KIR antibody or an antigen-binding portion thereof that specifically binds to an inhibitory KIR and blocks inhibitory KIR activity; and
   (b) instructions for using the anti-KIR antibody or an antigen-binding portion thereof in the method of claim 1.

15. The method of claim 1, wherein the anti-KIR antibody or antigen-binding portion thereof comprises a human heavy chain variable region comprising consecutively linked amino acids having the sequence set forth in SEQ ID NO:1 and a human light chain variable region comprising consecutively linked amino acids having the sequence set forth in SEQ ID NO:2.

* * * * *

SEQUENCE LISTING

```
<160> NUMBER OF SEQ ID NOS: 11

<210> SEQ ID NO 1
<211> LENGTH: 123
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
            20                  25                  30

Ala Ile Ser Trp Val Arg Gln Ala Pro Gly Gln Gly Leu Glu Trp Met
        35                  40                  45

Gly Gly Phe Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser
        115                 120

<210> SEQ ID NO 2
<211> LENGTH: 109
<212> TYPE: PRT
<213> ORGANISM: Homo sapiens

<400> SEQUENCE: 2

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95
```

```
Thr Phe Gly Gln Gly Thr Lys Leu Glu Ile Lys Arg Thr
                100                 105
```

<210> SEQ ID NO 3
<211> LENGTH: 450
<212> TYPE: PRT
<213> ORGANISM: Homo sapiens

<400> SEQUENCE: 3

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Phe Tyr
             20                  25                  30

Ala Ile Ser Trp Val Arg Gln Ala Pro Gly Gln Gly Leu Glu Trp Met
         35                  40                  45

Gly Gly Phe Ile Pro Ile Phe Gly Ala Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Ile Pro Ser Gly Ser Tyr Tyr Tyr Asp Tyr Asp Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365
```

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
450

<210> SEQ ID NO 4
<211> LENGTH: 450
<212> TYPE: PRT
<213> ORGANISM: Homo sapiens

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
                20                  25                  30

Ala Ile Ser Trp Val Arg Gln Ala Pro Gly Gln Gly Leu Glu Trp Met
                35                  40                  45

Gly Gly Phe Ile Pro Ile Phe Gly Ala Ala Asn Tyr Ala Gln Lys Phe
                50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Ile Pro Ser Gly Ser Tyr Tyr Tyr Asp Tyr Asp Met Asp Val
                100                 105                 110

Trp Gly Gln Gly Thr Thr Val Thr Val Ser Ser Ala Ser Thr Lys Gly
                115                 120                 125

Pro Ser Val Phe Pro Leu Ala Pro Cys Ser Arg Ser Thr Ser Glu Ser
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Lys Thr Tyr Thr Cys Asn Val
                195                 200                 205

Asp His Lys Pro Ser Asn Thr Lys Val Asp Lys Arg Val Glu Ser Lys
                210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

-continued

```
Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 5
<211> LENGTH: 214
<212> TYPE: PRT
<213> ORGANISM: homo sapiens

<400> SEQUENCE: 5

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 5
<212> TYPE: PRT
<213> ORGANISM: Homo sapiens

<400> SEQUENCE: 6

Phe Tyr Ala Ile Ser
1               5

<210> SEQ ID NO 7
<211> LENGTH: 16
<212> TYPE: PRT
<213> ORGANISM: Homo sapiens

<400> SEQUENCE: 7

Gly Phe Ile Pro Ile Phe Gly Ala Ala Asn Tyr Ala Gln Lys Phe Gln
1               5                   10                  15

<210> SEQ ID NO 8
<211> LENGTH: 14
<212> TYPE: PRT
<213> ORGANISM: Homo sapiens

<400> SEQUENCE: 8

Ile Pro Ser Gly Ser Tyr Tyr Tyr Asp Tyr Asp Met Asp Val
1               5                   10

<210> SEQ ID NO 9
<211> LENGTH: 11
<212> TYPE: PRT
<213> ORGANISM: Homo sapiens

<400> SEQUENCE: 9

Arg Ala Ser Gln Ser Val Ser Ser Tyr Leu Ala
1               5                   10

<210> SEQ ID NO 10
<211> LENGTH: 7
<212> TYPE: PRT
<213> ORGANISM: Homo sapiens

<400> SEQUENCE: 10

Asp Ala Ser Asn Arg Ala Thr
1               5

<210> SEQ ID NO 11
<211> LENGTH: 9
<212> TYPE: PRT
<213> ORGANISM: Homo sapiens

<400> SEQUENCE: 11

Gln Gln Arg Ser Asn Trp Met Tyr Thr
1               5